(12) United States Patent
Dropinski et al.

(10) Patent No.: US 7,807,692 B2
(45) Date of Patent: Oct. 5, 2010

(54) ANTIDIABETIC OXAZOLIDINEDIONES AND THIAZOLIDINEDIONES

(75) Inventors: James F. Dropinski, Colts Neck, NJ (US); Peter T. Meinke, Scotch Plains, NJ (US); Guo Q. Shi, Monmouth Junction, NJ (US); Yong Zhang, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 441 days.

(21) Appl. No.: 11/922,628

(22) PCT Filed: Jun. 30, 2006

(86) PCT No.: PCT/US2006/026047
§ 371 (c)(1),
(2), (4) Date: Dec. 20, 2007

(87) PCT Pub. No.: WO2007/008501
PCT Pub. Date: Jan. 18, 2007

(65) Prior Publication Data
US 2010/0168164 A1 Jul. 1, 2010

Related U.S. Application Data

(60) Provisional application No. 60/697,039, filed on Jul. 6, 2005.

(51) Int. Cl.
*A61K 31/47* (2006.01)
*A61K 31/42* (2006.01)
*A61K 31/44* (2006.01)
*C07D 413/00* (2006.01)
*C07D 215/02* (2006.01)
*C07D 263/00* (2006.01)

(52) U.S. Cl. ............... 514/307; 514/314; 514/376; 514/340; 546/271.4; 546/166; 548/227

(58) Field of Classification Search .............. 548/227; 514/376, 340, 307, 314; 546/271.4, 166
See application file for complete search history.

(56) References Cited

U.S. PATENT DOCUMENTS 6,784,184 B2 8/2004 Epstein et al.
2007/0173434 A1 7/2007 Shi et al.

FOREIGN PATENT DOCUMENTS

| EP | 1 709 014 B1 | 10/2006 |
| WO | 99/32465 A1 | 7/1999 |
| WO | WO 01/30343 A1 | 5/2001 |
| WO | WO 02/08188 A1 | 1/2002 |
| WO | WO 2005/007095 A2 | 1/2005 |

OTHER PUBLICATIONS

Hcaplus Abstract 138:221580, "Preparation of arylsulfonylthiazolidinediones as inhibitors of farnesyl-protein transferase", Salaski et. al., 2003.*
H. K. Rami et al., "Synthetic ligands for PPAR gamma—review of patent literature 1994-1999", Expert Opinion on Therapeutic Patents, vol. 10, No. 5, pp. 623-634 (2000).

* cited by examiner

*Primary Examiner*—Janet L Andres
*Assistant Examiner*—Binta M Robinson
(74) *Attorney, Agent, or Firm*—Janet E. Fair; John C. Todaro

(57) ABSTRACT

Phenoxyphenyl and phenoxybenzyl oxazolidine-2,4-diones and thiazolidine-2,4-diones are agonists or partial agonists of PPAR gamma and are useful in the treatment and control of hyperglycemia that is symptomatic of type II diabetes, as well as dyslipidemia, hyperlipidemia, hypercholesterolemia, hypertriglyceridemia, and obesity that are often associated with type 2 diabetes.

21 Claims, No Drawings

ANTIDIABETIC OXAZOLIDINEDIONES AND THIAZOLIDINEDIONES

CROSS-REFERENCE TO RELATED APPLICATIONS

This application is a U.S. National Phase application under 35 U.S.C. §371 of PCT Application No. PCT/US2006/026047, file Jun. 30, 2006, which published as WO 2007/008501 A on Jan. 18, 2007, and claims priority under 35 U.S.C. §119 from U.S. Provisional Application No. 60/697,039, filed Jul. 6, 2005.

FIELD OF THE INVENTION

The instant invention is concerned with phenoxyphenyl and phenoxybenzyl oxazolidine-2,4-diones and thiazolidine-2,4-diones, including pharmaceutically acceptable salts and prodrugs thereof, which are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes often have hyperinsulinemia (elevated plasma insulin levels); however, these patients have insulin resistance, which means that they have a resistance to the effect of insulin in stimulating glucose and lipid metabolism in the main insulin-sensitive tissues, which are muscle, liver and adipose tissues. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle and inadequate insulin-mediated repression of lipolysis in adipose tissue and of glucose production and secretion in the liver. Patients who are insulin resistant but not diabetic compensate for the insulin resistance by secreting more insulin, so that plasma glucose levels may be elevated but are not elevated enough to meet the criteria of Type 2 diabetes, which are based on fasting plasma glucose.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that are listed above that occur with type 2 diabetes, such as atherosclerosis and coronary heart disease.

There are several available treatments for type 2 diabetes, each of which has its own limitations and potential risks. Physical exercise and a reduction in dietary intake of calories often dramatically improve the diabetic condition and are the best first line treatment of type 2 diabetes. Compliance with this treatment is very poor because of well-entrenched sedentary lifestyles and excess food consumption, especially of foods containing high amounts of fat. A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. They are often used alone or as a first-line drug treatment for Type 2 diabetes, but they may also be used in combination with other drugs that are prescribed for type 2 diabetes. When administration of a sulfonylurea or meglitinide becomes ineffective, the amount of insulin in the body can be supplemented by the injection of insulin so that insulin concentrations are high enough to stimulate even the very insulin-resistant tissues. However, dangerously low levels of plasma glucose can result from administration of insulin and/or insulin secretagogues, and an increased level of insulin resistance due to the even higher plasma insulin levels can eventually occur.

The biguanides are another class of drugs that are widely used to treat type 2 diabetes. The two best known biguanides, phenformin and metformin, cause some correction of hyperglycemia. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones. New PPAR agonists are being developed for the treatment of Type 2 diabetes and/or dyslipidemia. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism.

Currently marketed PPAR agonists, which are glitazones, have exhibited shortcomings. Troglitazone was the first marketed glitazone, but it was eventually withdrawn from the marketplace because of hepatotoxicity. Another weakness in the currently marketed PPAR agonists is that monotherapy for type 2 diabetes produces only modest efficacy—a reduction in average plasma glucose of ≈20% and a decline from ≈9.0% to ≈8.0% in HemoglobinA1C. The current compounds also do not greatly improve lipid metabolism, and may actually have a negative effect on the lipid profile. These shortcomings have provided an incentive to develop better insulin sensitizers for Type 2 diabetes which function via similar mechanism(s) of action.

Recently, there have been reports of compounds that are PPAR gamma antagonists or PPAR partial agonists. WO01/30343 describes a specific compound that is a PPAR partial agonist/antagonist that is useful for the treatment of obesity and Type 2 diabetes. WO02/08188 discloses a class of PPAR agonists and partial agonists that are indole derivatives and that are useful in the treatment of Type 2 diabetes, with reduced side effects relating to body and heart weight gain. The PPAR partial gamma agonists are often referred to as selective PPAR modulators (SPPARM's).

SUMMARY OF THE INVENTION

The class of compounds described herein is a new class of potent PPAR ligands that in vitro are generally PPARγ agonists or partial agonists. The compounds may also be PPARγ antagonists. Some compounds may also have PPARα and/or PPARδ activity in addition to PPARγ activity. The compounds are useful in the treatment of PPAR modulated diseases, including type 2 diabetes, hyperglycemia, and insulin resistance.

The compounds may also be useful in the treatment of one or more lipid disorders, including mixed or diabetic dyslipidemia, isolated hypercholesterolemia, which may be manifested by elevations in LDL-C and/or non-HDL-C, hyper-apoBliproteinemia, hypertriglyceridemia, an increase in triglyceride-rich-lipoproteins, and low HDL cholesterol concentrations. They may also be useful in the treatment or amelioration of obesity. They may also be useful in treating or ameliorating atherosclerosis, vascular restenosis, inflammatory conditions, psoriasis, and polycystic ovary syndrome. They may also have utility in treating other PPAR mediated diseases, disorders and conditions.

The present invention is directed to compounds of formula I:

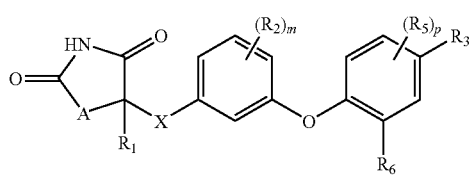

and pharmaceutically acceptable salts and prodrugs thereof.

In the compounds of Formula I:

A is O or S;

X is a bond or —C($R^7$)2—;

$R^1$ is selected from the group consisting of H and $C_1$-$C_3$ alkyl, wherein $C_1$-$C_3$ alkyl is optionally substituted with 1-3 halogens;

Each R2 is independently selected from the group consisting of halogen, $C_1$-$C_3$ alkyl, and —O$C_1$-$C_3$ alkyl, wherein $C_1$-$C_3$ alkyl and —O$C_1$-$C_3$ alkyl are optionally substituted with 1-3 halogens;

$R^3$ is selected from the group consisting of

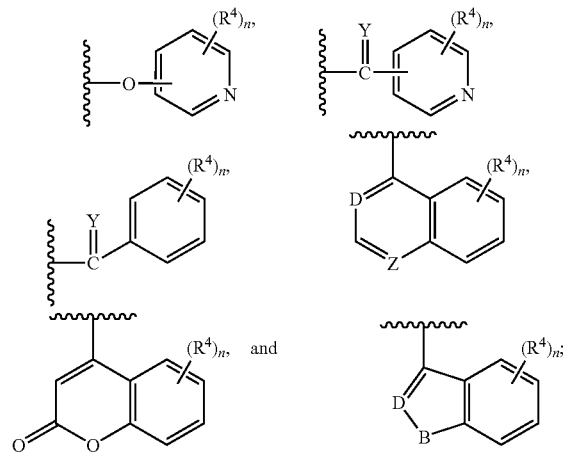

Y is selected from the group consisting of =O and =N—OH;

D and Z are each independently selected from the group consisting of =C($R^7$)— and =N—;

B is selected from the group consisting of —N($R^7$)—, —O— and —S—;

Each $R^4$ is independently selected from the group consisting of halogen, —OH, $C_1$-$C_3$ alkyl, —O$C_1$-$C_3$ alkyl, —OC(=O)$C_1$-$C_3$ alkyl, and —S(O)$_q$$C_1$-$C_3$ alkyl, wherein $C_1$-$C_3$ alkyl, —O$C_1$-$C_3$ alkyl, —OC(=O)$C_1$-$C_3$ alkyl, and —S(O)$_q$$C_1$-$C_3$ alkyl are optionally substituted with 1-5 halogens;

Each $R_5$ is independently selected from the group consisting of halogen, $C_1$-$C_3$ alkyl, and —O$C_1$-$C_3$ alkyl, wherein $C_1$-$C_3$ alkyl and —O$C_1$-$C_3$ alkyl are optionally substituted with 1-3 halogens;

$R_6$ is selected from the group consisting of $C_2$-$C_5$ alkyl, —$CH_2$Cyclopropyl, $C_3$-$C_6$ cycloalkyl, —O$C_2$-$C_5$ alkyl and —C(=O)$C_1$-$C_3$ alkyl, wherein said $R_6$ substituent is optionally substituted with 1-3 halogens;

Each $R^7$ is independently selected from the group consisting of H and $C_1$-$C_3$ alkyl, wherein $C_1$-$C_3$ alkyl is optionally substituted with 1-3 F;

m is an integer from 0-4;

n is an integer from 0-5;

p is an integer from 0-3; and q is an integer from 0-2.

In the above definitions and subsequent definitions, alkyl groups may be either linear or branched, unless otherwise specified.

These compounds are expected to be effective in lowering glucose, lipids, and insulin in diabetic patients and in non-diabetic patients that have impaired glucose tolerance and/or are in a pre-diabetic condition. The compounds are expected to be efficacious in the treatment of non-insulin dependent diabetes mellitus (NIDDM) in human and other mammalian patients, and specifically in the treatment of hyperglycemia and in the treatment of conditions associated with NIDDM, including hyperlipidemia, dyslipidemia, obesity, hypercholesterolemia, hypertriglyceridemia, atherosclerosis, vascular restenosis, inflammatory conditions, and other PPAR mediated diseases, disorders and conditions.

DETAILED DESCRIPTION OF THE INVENTION

The invention has numerous embodiments, summarized below. These embodiments include the compounds, pharmaceutically acceptable salts of these compounds, and pharmaceutical compositions comprising these compounds and a pharmaceutically acceptable carrier. These embodiments have especially useful properties in treating insulin resistance, type 2 diabetes, and dyslipidemia that is associated with type 2 diabetes and insulin resistance.

One embodiment of the invention comprises compounds of Formula I in which:

X is a bond or $CH_2$;

$R^1$ is selected from the group consisting of H and $C_1$-$C_3$ alkyl, wherein $C_1$-$C_3$ alkyl is optionally substituted with 1-3 F;

Each $R^2$ is independently selected from the group consisting of F, Cl, $CH_3$, $CF_3$, —$OCH_3$, and —$OCF_3$;

Each $R^4$ is independently selected from the group consisting of halogen, —OH, $C_1$-$C_3$ alkyl, —$OC_1$-$C_3$ alkyl, —$OC(=O)C_1$-$C_3$ alkyl, and —$S(O)_qC_1$-$C_3$ alkyl, wherein $C_1$-$C_3$ alkyl, —$OC_1$-$C_3$ alkyl, —$OC(=O)C_1$-$C_3$ alkyl, and —$S(O)_qC_1$-$C_3$ alkyl are optionally substituted with 1-3 F;

Each $R_5$ is independently selected from the group consisting of F, Cl, $CH_3$, —$OCH_3$, $CF_3$, and —$OCF_3$;

$R_6$ is selected from the group consisting of $C_2$-$C_5$ alkyl, —$CH_2$Cyclopropyl, and —$C(=O)C_1$-$C_3$ alkyl, wherein any alkyl or cycloalkyl groups of said $R_6$ substituent is optionally substituted with 1-3 F;

$R^7$ is selected from the group consisting of H and $C_1$-$C_3$ alkyl;

m is an integer selected from 0 and 1;

n is an integer from 0-3; and p is an integer from 0-2.

In another embodiment of the invention, compounds of Formula I have the following groups, where other groups are as defined previously:

A is O;

X is a bond or $CH_2$;

$R^1$ is $CH_3$;

Each $R^4$ is independently selected from the group consisting of F, Cl, —OH, $CH_3$, $CF_3$, —$OCH_3$, —$OCF_3$, —$OCH_2CH_3$, —$OC(=O)CH_3$, —$OCHF_2$, and —$S(O)_qCH_3$;

$R^5$ is Cl or F;

$R^6$ is selected from the group consisting of n-$C_3H_7$, —$CH_2$Cyclopropyl, and —$C(=O)C_2H_5$;

$R^7$ is selected from H and $CH_3$;

m is 0;

n is an integer from 1-2;

p is 0 or 1; and q is an integer from 0-2.

In other embodiments of compounds of Formula I, $R^1$ is H or $CH_3$, and other groups are as defined above. In preferred embodiments, $R^1$ is $CH_3$.

In many preferred embodiments, A is O. Other groups are as defined above.

In other preferred embodiments, A is S.

Another embodiment of the invention comprises compounds of Formula I in which $R^4$ is F, Cl, —OH, $CH_3$, $CF_3$, —$OCH_3$, —$OCF_3$, —$OCHF_2$, —$OC_2H_5$, —$OC(=O)CH_3$, or —$S(O)_qCH_3$, where q is 0, 1 or 2, and n is 1 or 2. Other groups are as defined above.

In many compounds of the invention as defined above, X is a bond.

In many compounds of the invention as defined above, X is $CH_2$.

Useful sub-groups of compounds as defined previously have $R^2$ groups that are selected from F, Cl, $CH_3$, $CF_3$, —$OCH_3$, and —$OCF_3$; where m is 0 or 1.

In preferred embodiments of compounds as defined previously, $R^6$ is selected from n-$C_3H_7$, —$CH_2$Cyclopropyl, and —$C(=O)_2H_5$. In many preferred compounds and groups of compounds, $R^6$ is n-$C_3H_7$.

Preferred $R^5$ substituents are selected from F, Cl, $CH_3$, —$OCH_3$, $CF_3$, and —$OCF_3$; where p is an integer from 0 to 2. Other preferred values of p are selected from 0 and 1.

Both enantiomers (i.e. R and S) at the 5-position of the oxazolidinedione and thiazolidinedione ring are active PPAR gamma agonists and partial agonists and are compounds of the invention. The R enantiomers are in general more active.

Structures of specific compounds and synthetic methods for making the compounds are disclosed in the Examples. Structures of specific examples of the invention are disclosed in Table 1 below, including pharmaceutically acceptable salts of the compounds.

TABLE 1

Table of Compounds

| Example | Structure |
| --- | --- |
| 1 | 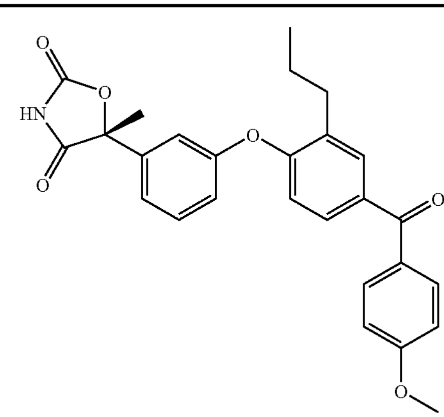 |

TABLE 1-continued

Table of Compounds

| Example | Structure |
|---------|-----------|
| 2 | 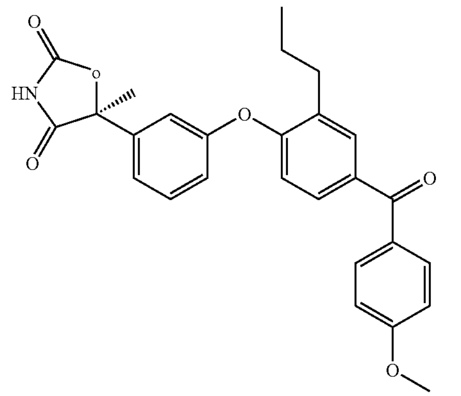 |
| 3 | 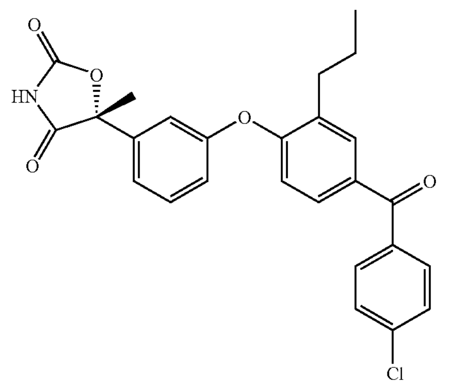 |
| 4 | 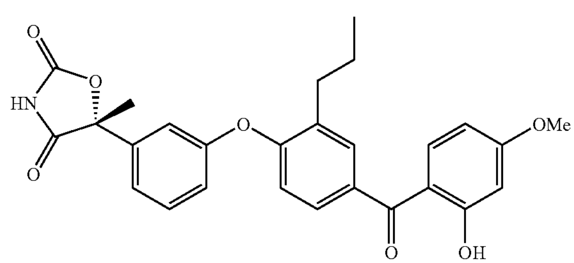 |
| 5 | 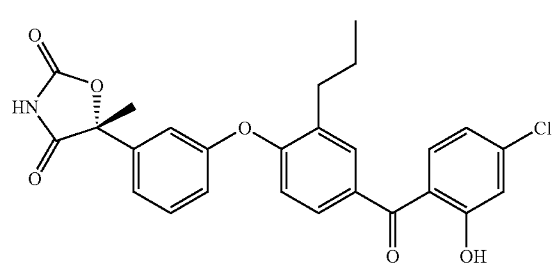 |

TABLE 1-continued
Table of Compounds
| Example | Structure |
|---|---|
| 6 | 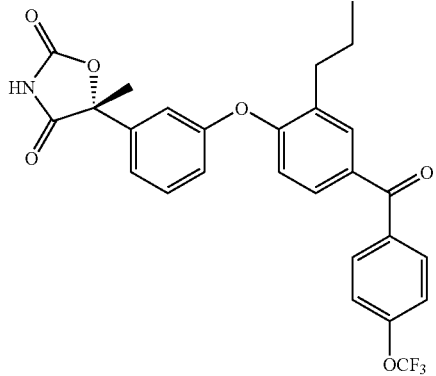 |
| 7 | 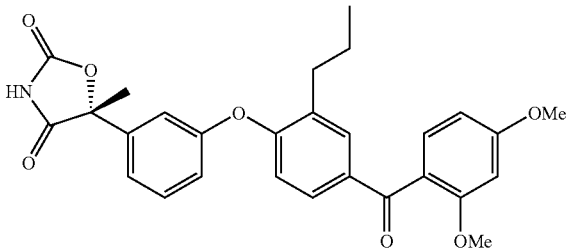 |
| 8 | 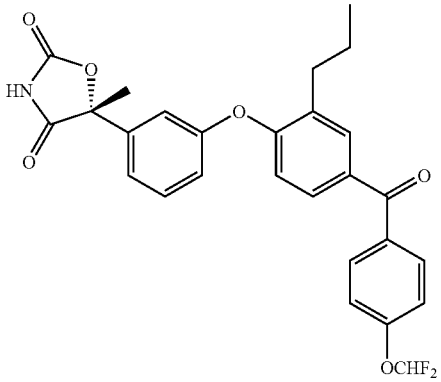 |
| 9 | 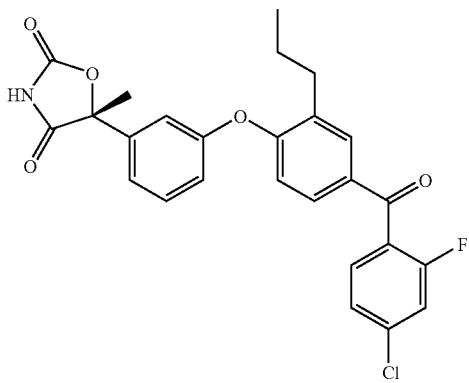 |

TABLE 1-continued

Table of Compounds

| Example | Structure |
|---|---|
| 10 | 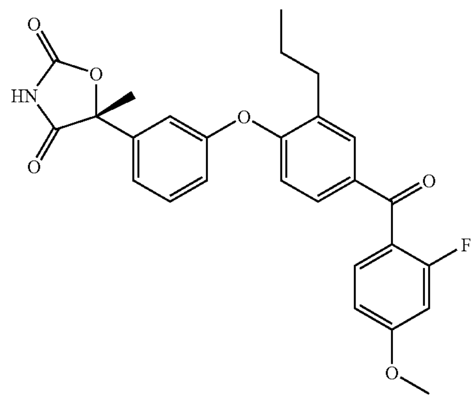 |
| 11 | 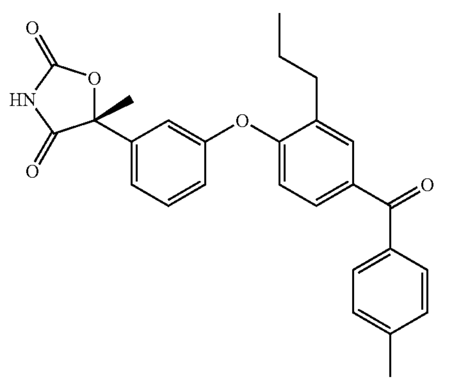 |
| 12 | 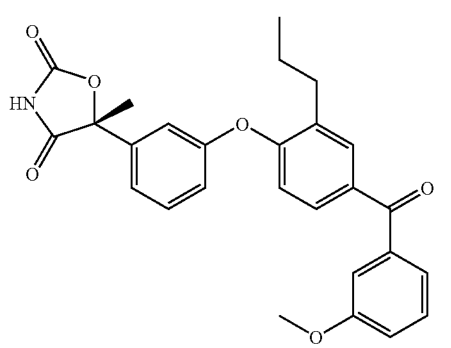 |
| 13 | 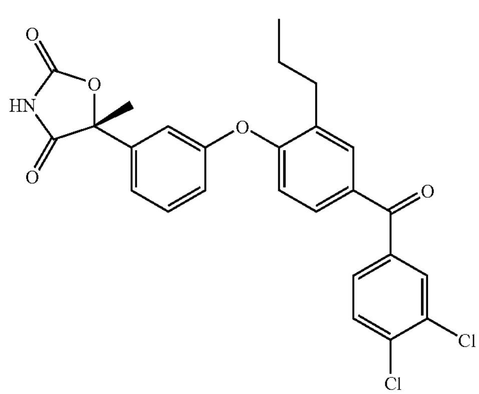 |

TABLE 1-continued

Table of Compounds

| Example | Structure |
|---|---|
| 14 | 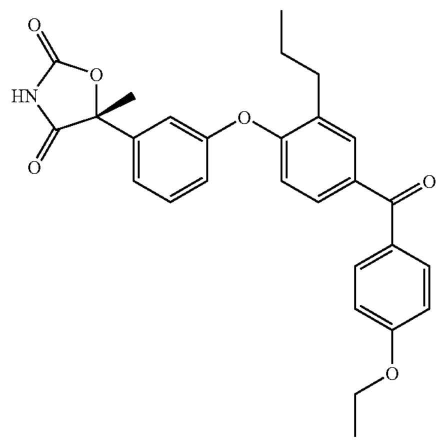 |
| 15 | 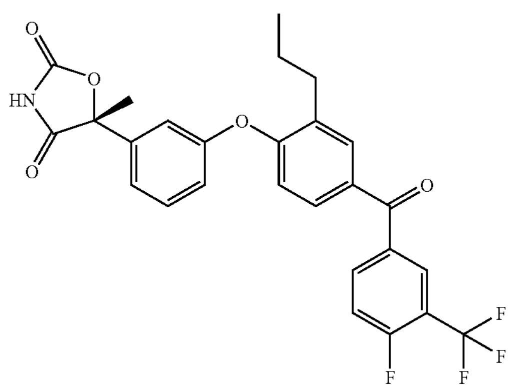 |
| 16 | 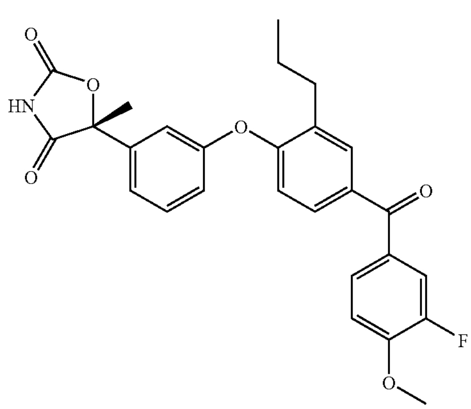 |

TABLE 1-continued
Table of Compounds
| Example | Structure |
|---|---|
| 17 | 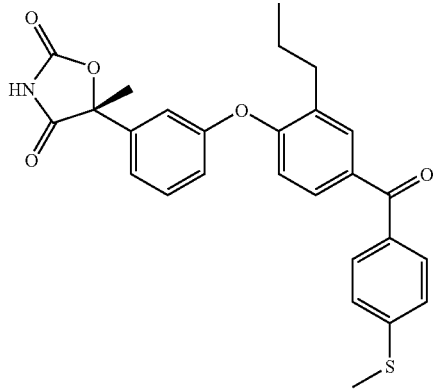 |
| 18 | 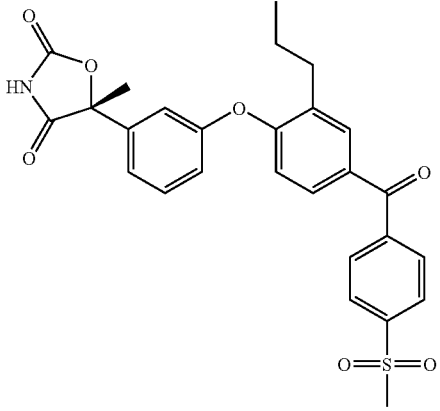 |
| 19 | 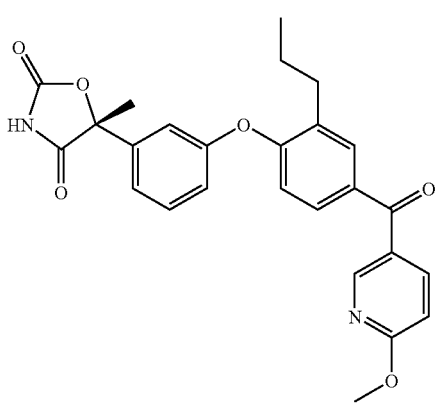 |

TABLE 1-continued

Table of Compounds

| Example | Structure |
|---|---|
| 20 | 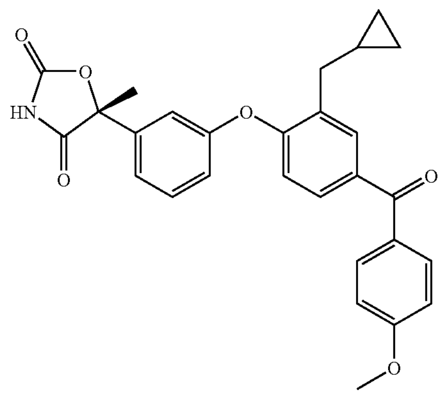 |
| 21 | 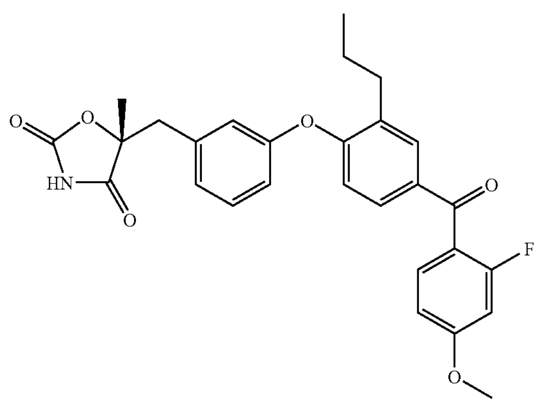 |
| 22 | 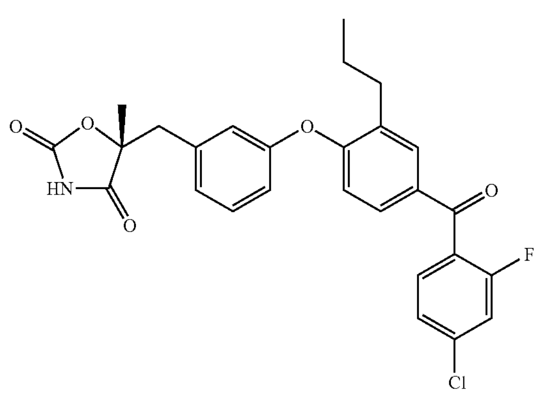 |

TABLE 1-continued
Table of Compounds
| Example | Structure |
|---|---|
| 23 | 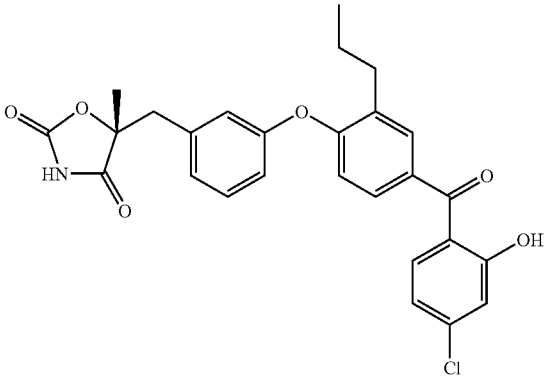 |
| 24 | 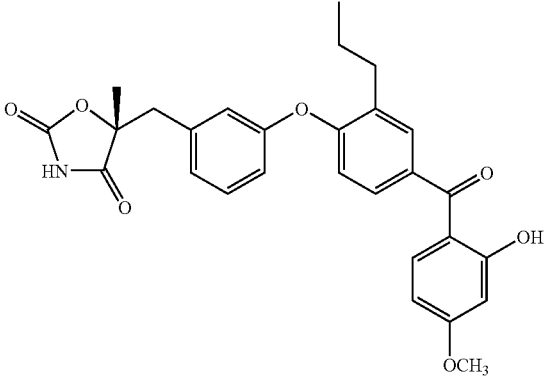 |
| 25 | 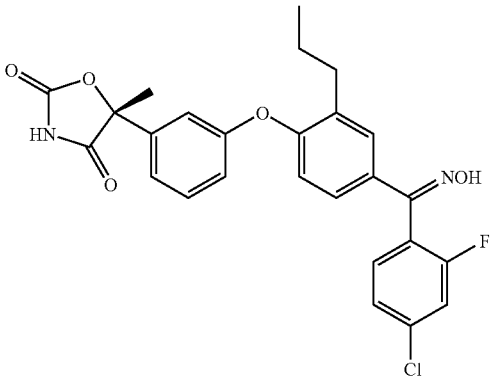 |
| 26 | 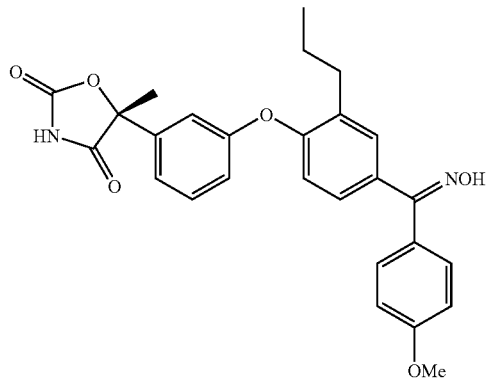 |

TABLE 1-continued

Table of Compounds

| Example | Structure |
|---------|-----------|
| 27 | 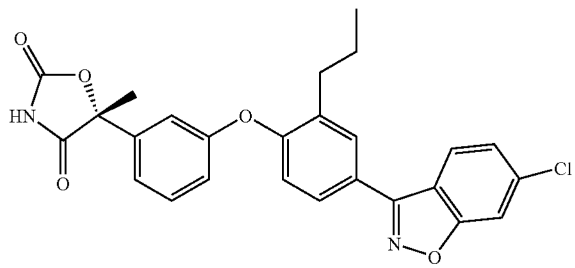 |
| 28 | 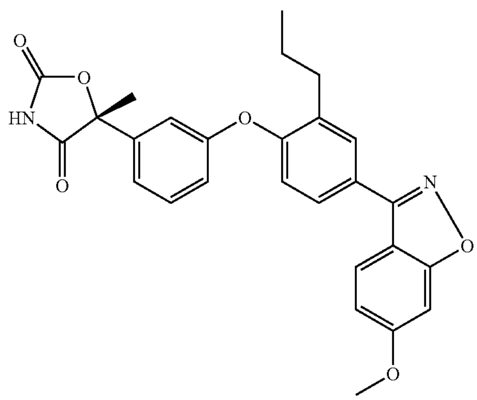 |
| 29 | 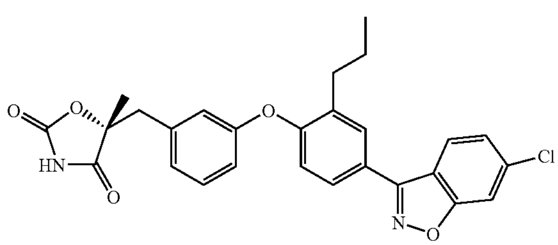 |
| 30 | 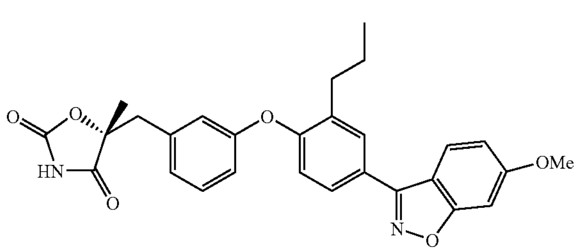 |

TABLE 1-continued
Table of Compounds
| Example | Structure |
|---|---|
| 31 | 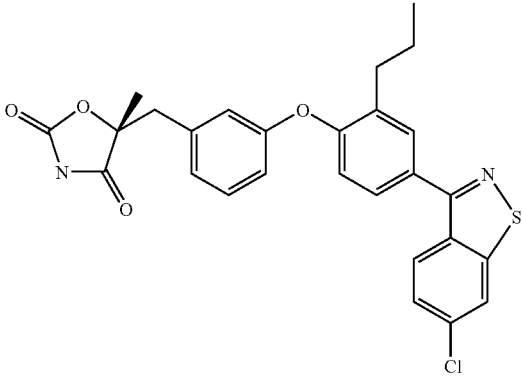 |
| 32 | 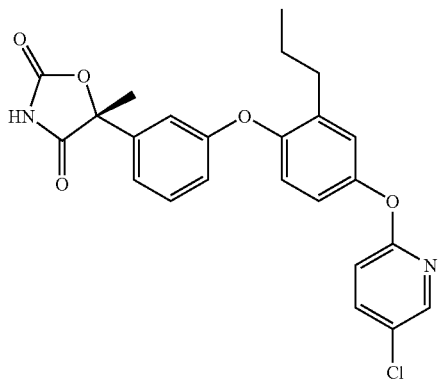 |
| 33 | 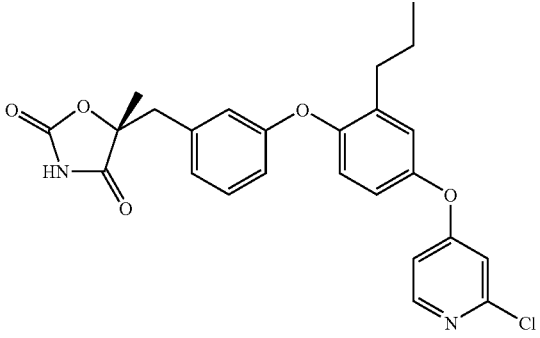 |
| 34 | 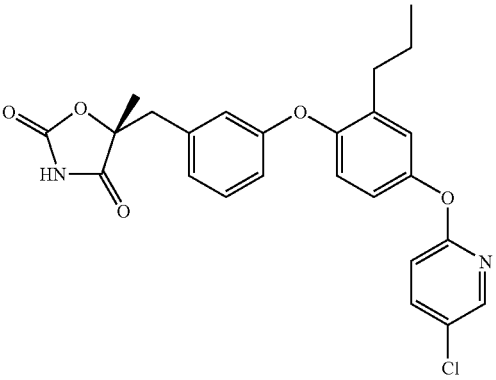 |

TABLE 1-continued
Table of Compounds
| Example | Structure |
|---------|-----------|
| 35 | 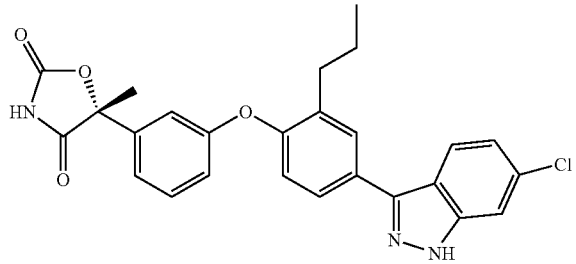 |
| 36 | 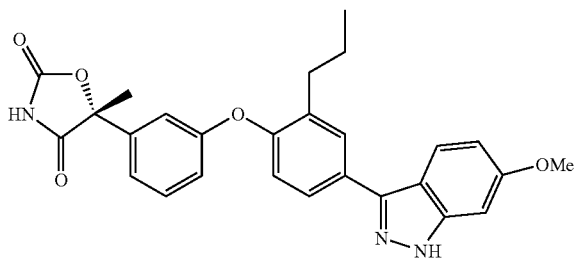 |
| 37 | 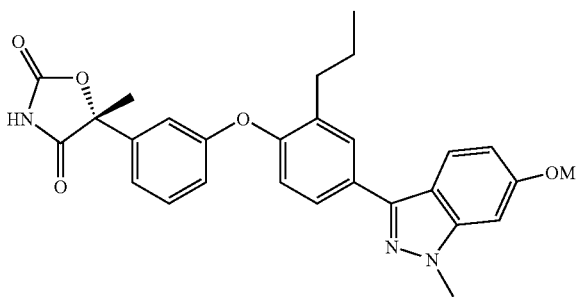 |
| 38 | 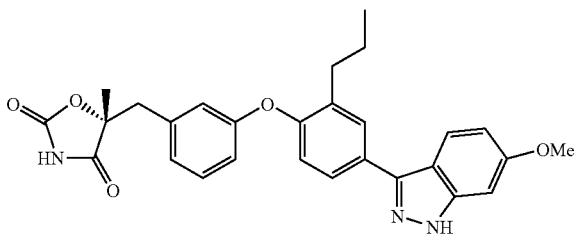 |
| 39 | 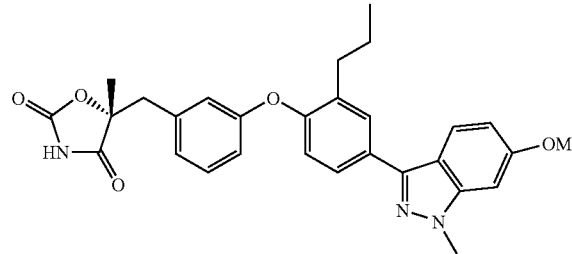 |

TABLE 1-continued

Table of Compounds

| Example | Structure |
|---|---|
| 40 | 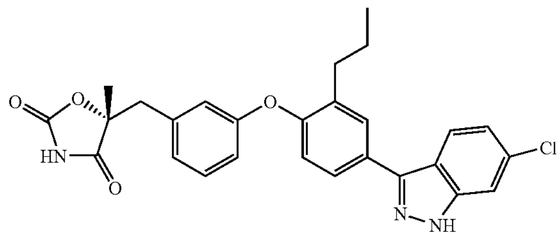 |
| 41 | 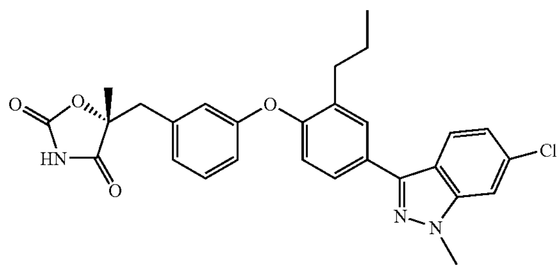 |
| 42 | 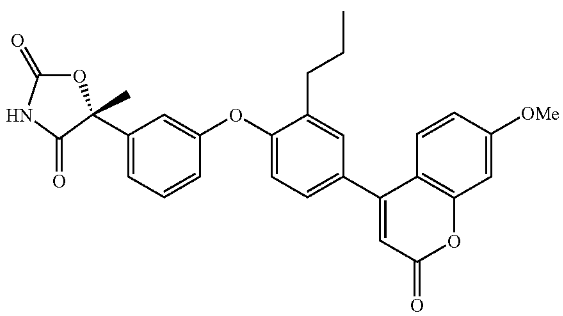 |
| 43 | 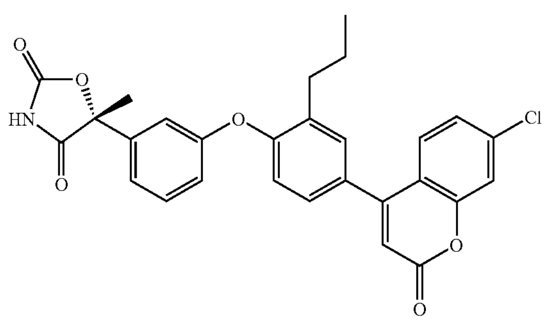 |
| 44 | 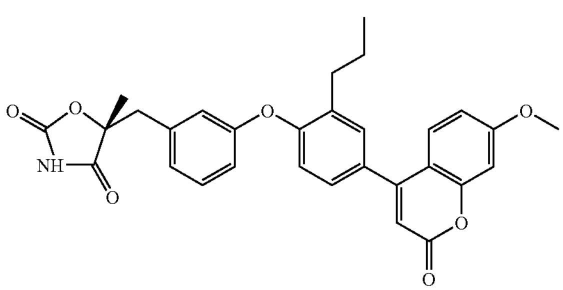 |

TABLE 1-continued

Table of Compounds

| Example | Structure |
|---------|-----------|
| 45 | 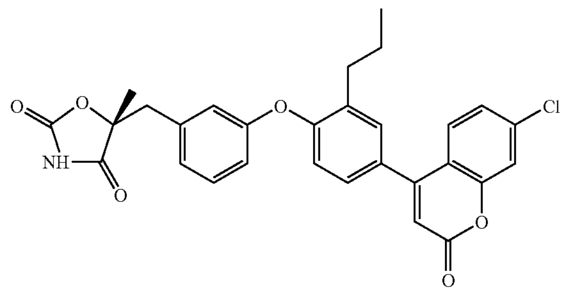 |
| 46 | 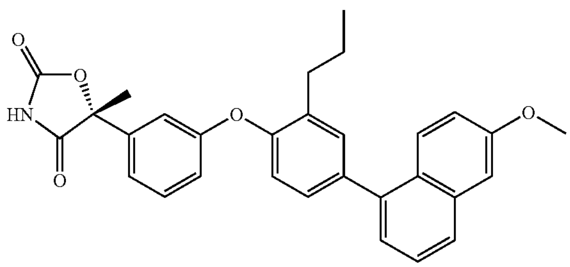 |
| 47 | 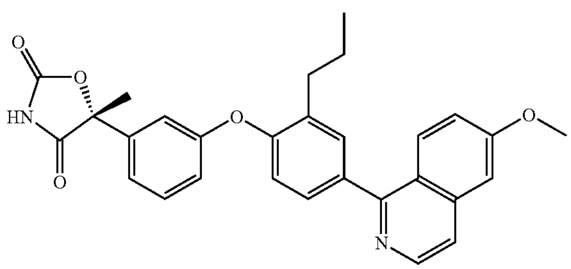 |
| 48 | 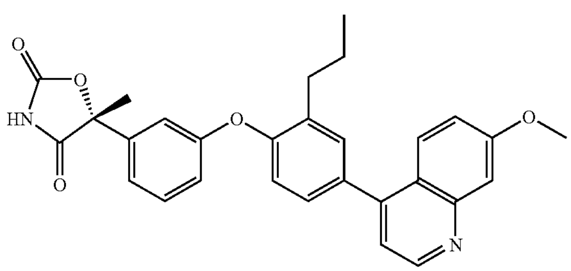 |

The compounds of this invention can be used in pharmaceutical compositions comprising the compound or a pharmaceutically acceptable salt thereof and a pharmaceutically acceptable carrier. The compounds of this invention can be used in pharmaceutical compositions that include one or more other active pharmaceutical ingredients. A compound of this invention can also be used in pharmaceutical compositions in which a compound of Formula I or a pharmaceutically acceptable salt thereof is the only active ingredient.

The compounds of the invention and pharmaceutically acceptable salts thereof can be used in the manufacture of medicaments for the treatment of type 2 diabetes mellitus in a human or other mammalian patient.

The compounds as defined herein may be used to treat diseases according to the following methods, as well as other diseases not listed below:

(1) A method for treating non-insulin dependent diabetes mellitus (type 2 diabetes) in a human or other mammalian patient in need of such treatment which comprises administering to the patient a therapeutically effective amount of a compound of Formula I;

(2) A method for treating or controlling hyperglycemia in a human or other mammalian patient in need of such treatment which comprises administering to the patient a therapeutically effective amount of a compound of Formula I;

(3) A method for treating or controlling the metabolic syndrome in a human or other mammalian patient in need of such treatment which comprises administering to the patient a therapeutically effective amount of a compound of Formula I;

(4) A method for treating or controlling obesity in a human or other mammalian patient in need of such treatment which comprises administering to the patient a therapeutically effective amount of a compound of Formula I;

(5) A method for treating or controlling hypercholesterolemia in a human or other mammalian patient in need of such treatment which comprises administering to the patient a therapeutically effective amount of a compound of Formula I;

(6) A method for treating or controlling hypertriglyceridemia in a human or other mammalian patient in need of such treatment which comprises administering to the patient a therapeutically effective amount of a compound of Formula I;

(7) A method for treating or controlling one or more lipid disorders, including mixed or diabetic dyslipidemia, low HDL cholesterol, high LDL cholesterol, hyperlipidemia, hypercholesterolemia, and hypertriglyceridemia in a human or other mammalian patient in need of such treatment which comprises administering to the patient a therapeutically effective amount of a compound of Formula I;

(8) A method for reducing the risks of adverse sequelae associated with metabolic syndrome in a human or other mammalian patient in need of such treatment which comprises administering to the patient a therapeutically effective amount of a compound of Formula I; and (9) A method for treating atherosclerosis, for reducing the risk of developing atherosclerosis, for delaying the onset of atherosclerosis, and/or reducing the risk of sequelae of atherosclerosis in a human or other mammalian patient in need of such treatment or at risk of developing atherosclerosis or sequelae of atherosclerosis, which comprises administering to the patient a therapeutically effective amount of a compound of Formula I. Sequelae of atherosclerosis include for example angina, claudication, heart attack, stroke, etc.

The compounds are especially useful in the treatment of the following diseases, by administering a therapeutically effective amount to a patient in need of treatment:

(1) Type 2 diabetes, and specifically hyperglycemia;
(2) Metabolic syndrome;
(3) Obesity; and
(4) Hypercholesterolemia.

Definitions

"Ac" is acetyl, which is $CH_3C(=O)—$.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each having from 3 to 10 carbon atoms, unless otherwise stated. The term also includes a monocyclic ring fused to an aryl group. Examples of cycloalkyl include cyclopropyl, cyclopentyl, cyclohexyl, cycloheptyl, and the like.

"Aryl" (and "arylene") when used to describe a substituent or group in a structure means a monocyclic, bicyclic or tricyclic compound in which all the rings are aromatic and which contains only carbon ring atoms. The term "aryl" can also refer to an aryl group that is fused to a cycloalkyl or heterocycle. "Heterocyclyl," "heterocycle," and "heterocyclic" means a fully or partially saturated monocyclic, bicyclic or tricyclic ring system containing at least one heteroatom selected from N, S and O, each of said rings having from 3 to 10 atoms. Examples of aryl substitiuents include phenyl and naphthyl. Aryl rings fused to cycloalkyls are found in indanyl, indenyl, and tetrahydronaphthyl. Examples of aryl fused to heterocyclic groups are found in 2,3-dihydrobenzofuranyl, benzopyranyl, 1,4-benzodioxanyl, and the like. Examples of heterocycles include tetrahydrofuran, piperazine, piperidine, and morpholine. Preferred aryl groups are phenyl or naphthyl. Phenyl is generally the most preferred aryl group.

"Heteroaryl" (and heteroarylene) means a mono-, bi- or tricyclic aromatic ring containing at least one ring heteroatom selected from N, O and S (including SO and $SO_2$), with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to comprehend all such isomeric forms of the compounds of Formula I.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of the Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the present invention are potent ligands having agonist, partial agonist or antagonist activity on one or more of the peroxisome proliferator activated receptor subtypes, particularly PPARγ. Some compounds may also be agonists, partial agonists or antagonists of the PPARα subtype as well as the PPARγ subtype, resulting in mixed PPARα/γ agonism. Some compounds (generally less preferred) may also be PPARδ ligands and have PPARδ activity in addition to their PPARγ activity. The compounds of this invention are useful in treating or controlling diseases, disorders or conditions which are mediated by one or more ligands of the individual PPAR subtypes (e.g. γ) or a combination of PPAR subtypes (e.g. α/γ).

One aspect of the present invention provides a method for the treatment and control of diseases that can be mediated by administration of a PPAR agonist or partial agonist, such as type 2 diabetes. One aspect of the present invention provides a method for the treatment and control of such diseases, disorders, or conditions in a mammalian or human patient in need of treatment which comprises administering to such mammal a therapeutically effective amount of a compound of Formula I. Compounds of the present invention may be useful in treating or controlling many PPAR mediated diseases and conditions, including, but not limited to: (1) type 2 diabetes (also known as non-insulin dependent diabetes mellitus, or NIDDM), (2) hyperglycemia, (3) low glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) irritable bowel syndrome, (16) inflammatory bowel disease, including Crohn's disease and ulcerative colitis, (17) other inflammatory conditions, (18) pancreatitis, (19) abdominal obesity, (20) neurodegenerative disease, (21) retinopathy, (22) psoriasis, (23) metabolic syndrome, (24) ovarian hyperandrogenism (polycystic ovarian syndrome), and other disorders where insulin resistance is a component. They may also have utility in treating high blood pressure, neoplastic conditions, adipose cell tumors, adipose cell carcinomas, such as liposarcoma, prostate cancer and other cancers, including gastric, breast, bladder and colon cancers, angiogenesis, osteoporosis, and Alzheimer's disease.

The compounds may have utility in treating osteoporosis. The compounds of this invention may treat osteoporosis or reduce the risk of developing osteoporosis by slowing or stopping the loss of bone density in a patient who has osteoporosis or is at risk of developing osteoporosis. The compounds of this invention may also reverse the loss of bone mass in patients who have already begun to lose bone mass.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors, niacin, bile acid sequestrants, microsomal triglyceride transport inhibitors, and bile acid reuptake inhibitors. These combination treatments may also be effective for the treatment or control of one or more related conditions selected from the group consisting of hypercholesterolemia, atherosclerosis, hyperlipidemia, hypertriglyceridemia, dyslipidemia, high LDL, and low HDL.

Another aspect of the invention provides a method of treating inflammatory conditions, including inflammatory bowel disease, Crohn's disease, and ulcerative colitis by administering an effective amount of a compound of this invention to a patient in need of treatment. Additional inflammatory diseases that may be treated with the instant invention include gout, rheumatoid arthritis, osteoarthritis, multiple sclerosis, asthma, ARDS, psoriasis, vasculitis, ischemia/reperfusion injury, frostbite, and related diseases.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 1 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.1 mg, 0.2 mg, 0.5 mg, 1 mg, 2 mg, 5 mg, 10 mg, 25 mg, 50 mg, 100 mg, and 250 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, and LY-818;
(b) biguanides such as metformin and phenformin;
(c) protein tyrosine phosphatase-1B (PTP-1B) inhibitors;
(d) dipeptidyl peptidase IV (DP-IV) inhibitors, such as sitagliptin, saxagliptin, and vildagliptin;
(e) insulin or insulin mimetics;
(f) sulfonylureas such as tolbutamide and glipizide, or related materials;
(g) α-glucosidase inhibitors (such as acarbose);
(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, and (viii) phenolic anti-oxidants, such as probucol;
(i) PPARα/γ dual agonists, such as KRP-297, muraglitazar, tesaglitazar, farglitazar, and JT-501;
(j) PPARδ agonists such as GW-501516 and those disclosed in WO97/28149;
(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $β_3$ adrenergic receptor agonists;
(l) ileal bile acid transporter inhibitors;
(m) agents intended for use in inflammatory conditions such as aspirin, non-steroidal anti-inflammatory drugs, glucocorticoids, azulfidine, and cyclo-oxygenase 2 selective inhibitors;
(n) glucagon receptor antagonists;
(o) GLP-1,
(p) GIP-1, and
(q) GLP-1 analogs, such as exendins, for example exenatide (Byetta).

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

BIOLOGICAL ASSAYS

A) PPAR Binding Assays

For preparation of recombinant human PPARγ, PPARδ, and PPARα: Human PPARγ$_2$, human PPARδ and human PPARα were expressed as gst-fusion proteins in E. coli. The full length human cDNA for PPARγ$_2$ was subcloned into the pGEX-2T expression vector (Pharmacia). The full length human cDNAs for PPARδ and PPARα were subcloned into the pGEX-KT expression vector (Pharmacia). E. coli containing the respective plasmids were propagated, induced, and harvested by centrifugation. The resuspended pellet was broken in a French press and debris was removed by centrifugation at 12,000× g. Recombinant human PPAR receptors were purified by affinity chromatography on glutathione sepharose. After application to the column, and one wash, receptor was eluted with glutathione. Glycerol (10%) was added to stabilize the receptor and aliquots were stored at −80° C.

For binding to PPARγ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamidine and 0.5 mM PMSF) containing 0.1% non-fat dry milk and 10 nM [$^3$H$_2$]AD5075, (21 Ci/mmole), ± test compound as described in Berger et al (Novel peroxisome proliferator-activated receptor (PPARγ) and PPARδ ligands produce distinct biological effects. J. Biol. Chem. (1999), 274: 6718-6725. Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARδ, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 2.5 nM [$^3$H$_2$]L-783483, (17 Ci/mmole), ± test compound as described in Berger et al (Novel peroxisome proliferator-activated receptory (PPARγ) and PPARδ ligands produce distinct biological effects.1999 J Biol Chem 274: 6718-6725). (L-783483 is 3-chloro-4-(3-(7-propyl-3-trifluoromethyl-6-benz-[4,5]-isoxazoloxy)propylthio)phenylacetic acid, Ex. 20 in WO 97/28137). Assays were incubated for ~16 hr at 4° C. in a final volume of 150 μL. Unbound ligand was removed by incubation with 100 μL dextran/gelatin-coated charcoal, on ice, for ~10 min. After centrifugation at 3000 rpm for 10 min at 4° C., 50 μL of the supernatant fraction was counted in a Topcount.

For binding to PPARα, an aliquot of receptor was incubated in TEGM (10 mM Tris, pH 7.2, 1 mM EDTA, 10% glycerol, 7 μL/100 mL β-mercaptoethanol, 10 mM Na molybdate, 1 mM dithiothreitol, 5 μg/mL aprotinin, 2 μg/mL leupeptin, 2 μg/mL benzamide and 0.5 mM PMSF) containing 0.1% non-fat dry milk and 5.0 nM [$^3$H$_2$]L-797773, (34

Ci/mmole), ± test compound. (L-797733 is (3-(4-(3-phenyl-7-propyl-6-benz-[4,5]-isoxazoloxy)butyloxy))phenylacetic acid, Ex.62 in WO 97/28137). Assays were incubated for ~16 hr at 4° C. in a final volume of 150 µL. Unbound ligand was removed by incubation with 100 µL dextran/gelatin-coated charcoal, on ice, for ~10 min. After centrifugation at 3000 rpm for 10 min at 4° C., 50 µL of the supernatant fraction was counted in a Topcount.

B) Gal-4 hPPAR Transactivation Assays

The chimeric receptor expression constructs, pcDNA3-hPPARγ/GAL4, pcDNA3-hPPARδ/GAL4, pcDNA3-hPPARα/GAL4 were prepared by inserting the yeast GAL4 transcription factor DBD adjacent to the ligand binding domains (LBDs) of hPPARγ, hPPARδ, hPPARα, respectively. The reporter construct, pUAS(5X)-tk-luc was generated by inserting 5 copies of the GAL4 response element upstream of the herpes virus minimal thymidine kinase promoter and the luciferase reporter gene. pCMV-lacZ contains the galactosidase Z gene under the regulation of the cytomegalovirus promoter. COS-1 cells were seeded at $12\times10^3$ cells/well in 96 well cell culture plates in high glucose Dulbecco's modified Eagle medium (DMEM) containing 10% charcoal stripped fetal calf serum (Gemini Bio-Products, Calabasas, Calif.), nonessential amino acids, 100 units/ml Penicillin G and 100 mg/ml Streptomycin sulfate at 37° C. in a humidified atmosphere of 10% $CO_2$. After 24 h, transfections were performed with Lipofectamine (GIBCO BRL, Gaithersburg, Md.) according to the instructions of the manufacturer. Briefly, transfection mixes for each well contained 0.48 µl of Lipofectamine, 0.00075 µg of pcDNA3-PPAR/GAL4 expression vector, 0.045 µg of pUAS(5X)-tk-luc reporter vector and 0.0002 µg of pCMV-lacZ as an internal control for transactivation efficiency. Cells were incubated in the transfection mixture for 5 h at 37° C. in an atmosphere of 10% $CO_2$. The cells were then incubated for ~48 h in fresh high glucose DMEM containing 5% charcoal stripped fetal calf serum, nonessential amino acids, 100 units/ml Penicillin G and 100 mg/ml Streptomycin sulfate ± increasing concentrations of test compound. Since the compounds were solubilized in DMSO, control cells were incubated with equivalent concentrations of DMSO; final DMSO concentrations were ≦0.1%, a concentration which was shown not to effect transactivation activity. Cell lysates were produced using Reporter Lysis Buffer (Promega, Madison, Wis.) according to the manufacturer's instructions. Luciferase activity in cell extracts was determined using Luciferase Assay Buffer (Promega, Madison, Wis.) in an ML3000 luminometer (Dynatech Laboratories, Chantilly, Va.). β-galactosidase activity was determined using β-D-galactopyranoside (Calbiochem, San Diego, Calif.).

Agonism is determined by comparison of maximal transactivation activity with a full PPAR agonist, such as rosiglitazone. Generally, if the maximal stimulation of transactivation is less than 50% of the effect observed with a full agonist, then the compound is designated as a partial agonist. If the maximal stimulation of transactivation is greater than 50% of the effect observed with a full agonist, then the compound is designated as a full agonist. The compounds of this invention have EC50 values in the range of 1 nM to 3000 nM.

C) In Vivo Studies

Male db/db mice (10-11 week old C57B1/KFJ, Jackson Labs, Bar Harbor, Me.) are housed 5/cage and allowed ad lib. access to ground Purina rodent chow and water. The animals, and their food, are weighed every 2 days and are dosed daily by gavage with vehicle (0.5% carboxymethylcellulose) ± test compound at the indicated dose. Drug suspensions are prepared daily. Plasma glucose, and triglyceride concentrations are determined from blood obtained by tail bleeds at 3-5 day intervals during the study period. Glucose and triglyceride determinations are performed on a Boehringer Mannheim Hitachi 911 automatic analyzer (Boehringer Mannheim, Indianapolis, Ind.) using heparinized plasma diluted 1:6 (v/v) with normal saline. Lean animals are age-matched heterozygous mice maintained in the same manner.

EXAMPLES

The following Examples are provided to illustrate the invention so that it is more fully appreciated and understood. The examples are not to be construed as limiting the invention in any manner. The scope of the invention is defined by the appended claims.

The following scheme further teaches how compounds that are not specifically disclosed or whose syntheses are not fully described can be made by one of ordinary skill in the art. Starting materials are made using known procedures or as illustrated. Some starting materials may also be commercially available.

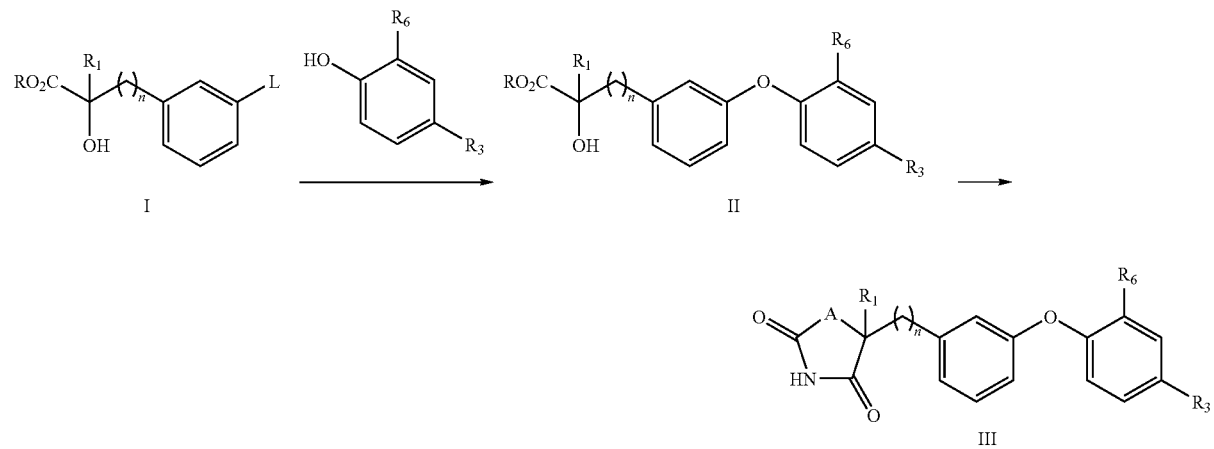

-continued

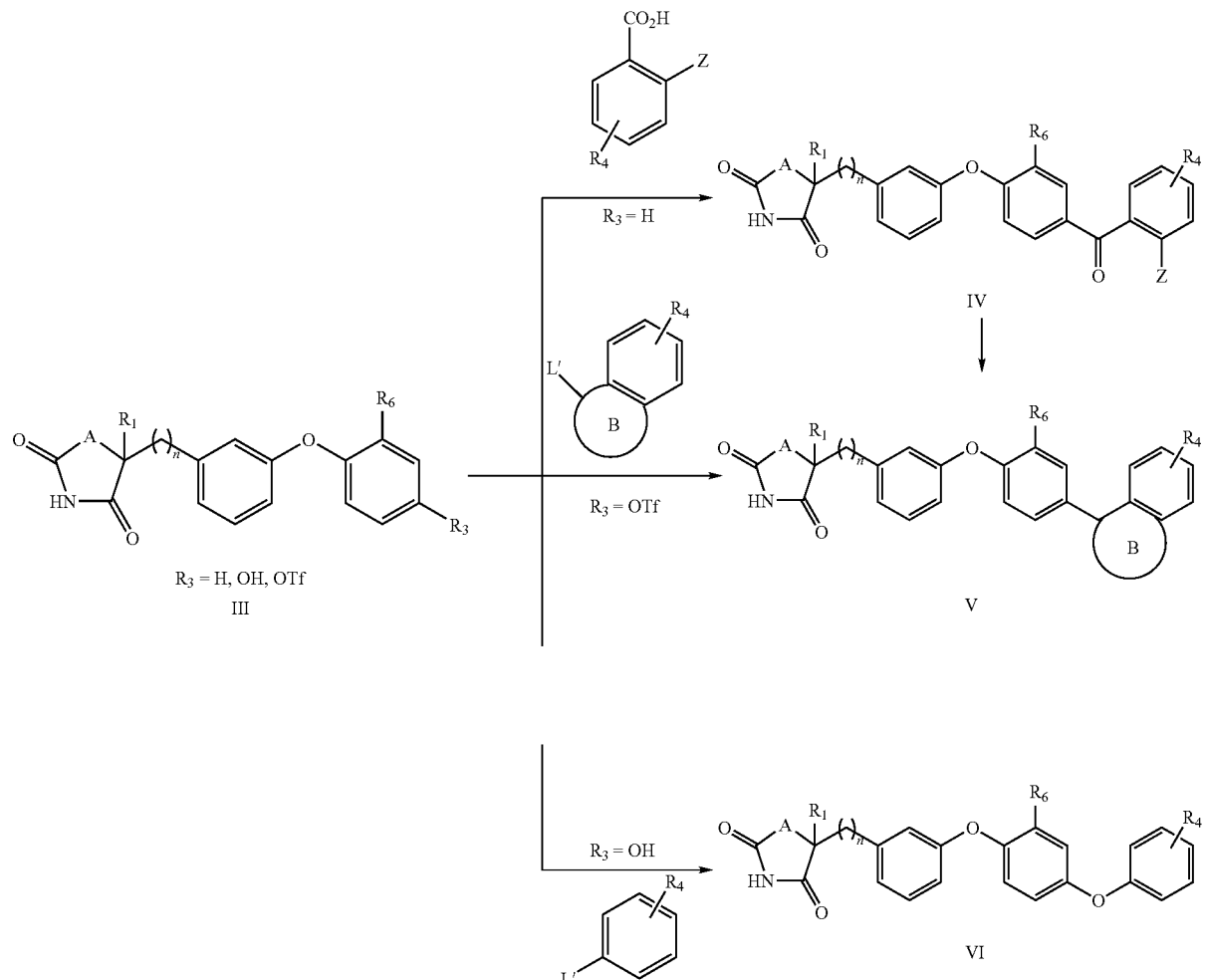

n = 0 or 1
A = O or S
B = 5 or 6-memeber ring

Suitably α-substituted phenylacetates or their homologs I are coupled with 2-substituted phenols to give diaryl ether derivatives II. The α-substituted ester moiety in compound II is then converted to a 1,3-oxazolin-2,4-dione (OZD) or 1,3-thiazolin-2,4-dione (TZD) ring to furnish compound III. Compound III can either be the final product or used as a key intermediate in a variety of synthetic transformations. Thus, Friedel-Crafts reaction of intermediate III with an aromatic acid or its derivative gives a diarylketone compound IV. Furthermore, if an appropriate substituent (e.g., Z=F, OH) is present ortho to the keto group, the aroyl moiety in compound IV can be transformed into a benzo-annulated five- or six-membered heterocycle to give compound V. Alternatively, when a phenolic hydroxy group is part of the structure of intermediate III, the resulting phenol (R3=OH) can be used to couple with appropriate coupling partners, e.g., aryl boronic acids, aryl halides, to afford fused bicyclic compound V or aryl ether compound VI.

Intermediate 1

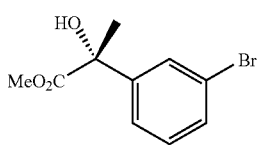

Step 1. Preparation of 1-bromo-3-(2-propenyl)benzene

A solution of NaHMDS in THF (1.0 M, 18.0 mL, 18.0 mmol) was added to a suspension of methyltriphenylphosphonium bromide (6.4 g, 18.0 mmol) in THF (60 mL) cooled with an ice bath. The resulting orange-colored suspension was stirred for 30 min and then cooled to −78° C. 3-Bromoacetophenone (3.0 g, 15.0 mmol) was added dropwise. After 30 min at −78 C, the reaction mixture was warmed to 25° C. and quenched with acetic acid (1.0 mL). After removal of the solvent, the residue was triturated with ethyl acetate/hexane (3:7, 100 mL) and filtered through a short column of silica gel. Concentration of the filtrate gave the title compound.

$^1$H NMR (500 MHz, CDCl$_3$) δ 7.62 (t, J=2.5 Hz, 1H), 7.50 (m 1 H), 7.41 (m, 1H), 7.22 (t, J=8.5 Hz, 1H).

Step 2. Preparation of (2R)-2-(3-bromophenyl)-1,2-propanediol

A mixture of 1-bromo-3-(2-propenyl)benzene from step 1 (2.9 g, 15 mmol) and AD-mix-β (Aldrich, 21.0 g) in t-BuOH-H$_2$O (1:1, 150 mL) was vigorously stirred at 4° C. for 16 h. The reaction was quenched with solid Na$_2$SO$_3$ (5.0 g) and diluted with ethyl acetate (150 mL). The aqueous was separated and extracted with ethyl acetate. The combine organic phase was washed with brine, dried and filtered through a short path of silica gel. Removal of the solvent gave essentially pure title compound.

$^1$H NMR (500 MHz, CDCl$_3$) δ 7.63 (t, J=2.5 Hz, 1H), 7.40 (m, 1H), 7.36 (m, 1H), 7.23 (t, J=8.4 Hz, 1H ), 3.75 (d, J=11.8 Hz, 1H), 3.62 (d, J=11.8 Hz, 1H), 1.50 (s, 3H).

Step 3. Preparation of Methyl (2R)-2-(3-bromophenyl)-2-hydroxypropanoate

The diol from step 2 (3.3 g, 15 mmol) and 10% Pt on carbon (1.5 g) were mixed in 0.1 M K$_2$HPO$_4$ buffer (300 mL). The reaction mixture was heated at 80° C. and a stream of air was bubbled in for 6 h. The hot reaction mixture was filtered through a pad of Celite and the filter cake was washed with ethyl acetate containing 5% of acetic acid (100 mL). The aqueous filtrate was acidified with concentrated hydrochloric acid to pH 2 and extracted with ethyl acetate (3×80 mL). The combined organic phase was washed with brine, dried and concentrated. The residue was dissolved in 7:1 (v/v) benzene-methanol (75 mL) and treated with trimethylsilyldiazomethane (1.0 M in heptane) until gas evolution ceased. The volatiles were removed and the residue was purified by chromatography on silica gel eluting with 7:3 (v/v) hexane-ethyl acetate to give the title compound.

$^1$H NMR (500 MHz, CD$_3$OD) δ 7.71 (t, J=2.0 Hz, 1H), 7.49 (dt, J=8.0 Hz, 1.0 Hz, 1H), 7.44 (ddd, J=8.0 Hz, 2.0 Hz, 1.0 Hz, 1H), 7.26 (t, J=8.0 Hz, 1H), 3.72 (s, 3H), 1.72 (s, 3H).

MS (ESI, m/z): 281.0 (M+Na−1), 241.0 (M−18).

Intermediate 2

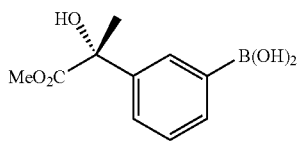

Step 1. Preparation of Methyl (2R)-2-hydroxy-2-[3-(4,4,5,5,-tetramethyl-1,3,2-dioxaborolan-2yl)phenyl]propanoate A mixture of intermediate 1 (2.6 g, 10 mmol), bis(pinacolato)diboron (2.8 g, 11 mmol), potassium acetate (2.9 g, 30 mmol) and Pd(dppf)Cl$_2$ (0.49 g 0. 6 mmol) in DMSO (50 mL) was degassed and heated under nitrogen at 80° C. for 2 h. The reaction mixture was diluted with diethyl ether (100 mL) and filtered through a short path of silica gel. The filtrate was washed with water (2×100 mL) and concentrated. The residue was purified by chromatography on silica gel eluting with 2:8 ethyl acetate:hexane to give the title product.

Step 2. Preparation of (2R)-2-hydroxy-2-[3-(borono)phenyl] propanoate

A mixture of the product from Step 1 (0.61 g, 2.0 mmol), sodium periodate (1.3 g, 6.0 mmol) and ammonium acetate (0.31 g, 4.0 mmol) in acetone-water (1:1, 20 mL) was stirred at 25° C. for 16 h. The precipitate was filtered off and the filtrate was evaporated. The aqueous phase was acidified with 2 N HCl to pH 3 and extracted with ethyl acetate (3×20 mL). The organic phase was washed with brine, dried and concentrated to give essentially pure Intermediate 2.

$^1$H NMR (500 MHz, CDCl$_3$) δ8.45 (s, 1H), 8.22 (d, J=7.5 Hz, 1H), 7.84 (d, J=7.5 Hz, 1H), 7.56 (t, J=7.5 Hz, 1H), 3.88 (s, 3H).

MS (ESI, m/z): 247.1 (M+Na$^+$).

Intermediate 3

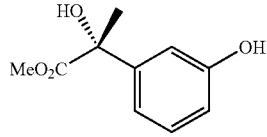

To a solution of intermediate 2 (2.47 g, 10 mmol) in dichloromethane (50 mL) was added dropwise a 30% solution of hydrogen peroxide in water (3.4 mL, 30 mmol). After 30 min, the reaction mixture was quenched with aqueous sodium sulfite and extracted with dichloromethane. After removal of the solvent, the crude product was purified by chromatography on silica gel eluting with a 7:3 mixture of hexane and ethyl acetate to afford Intermediate 3.

$^1$H NMR (500 MHz, CD$_3$OD) δ 7.25 (t, J=8.0 Hz, 1H), 7.00 (dt, J=8.0, 2.0 Hz, 1H), 6.98 (t, J=2 Hz, 1H), 6.81 (dt, J=8.0, 2.0 Hz, 1H), 1.87 (s, 3H).

MS (ESI, m/z): 208.2 (M+1).

Intermediate 4

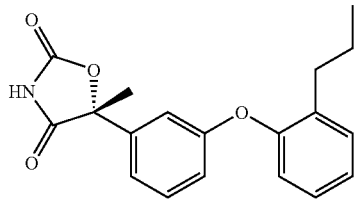

Step 1. Preparation of Methyl (2R)-2-hydroxy-2-[3-(2-propylphenoxy)phenyl]propanoate A mixture of intermediate 1 (2.6 g, 10 mmol), 2-propylphenol(2.0 g, 15 mmol), palladium acetate (90 mg, 0.04 mmol), di(t-butyl)(2-biphenyl)phosphine (179 mg, 0.06 mmol) and potassium phophate (4.2 g, 20 mmol) in toluene (30 mL) was degassed and heated under N$_2$ at 100° C. for 16 h. The reaction mixture was diluted with ether (50 mL) and filtered through a short path of silica gel to give the crude title product, which was used directly for the next step.

Step 2. Preparation of (2R)-2-hydroxy-2-[3-(2-propylphenoxy)phenyl]propamide

A solution of the crude product from Step 1 in methanol (35 mL) was cooled to 0° C. and saturated with ammonia gas. The solution was kept at 25° C. for 2 days and then concentrated. The residue was chromatographed on silica gel eluting first with 3:7 ethyl acetate:hexane and then with 100% ethyl acetate. The ethyl acetate fraction was concentrated to give the title compound.

Step 3. Preparation of (5R)-5-[3-(2-propylphenoxy)phenyl]-5-methyl-1,3-oxazolin-1,4-dione The amide from step 2 (2.1 g, 7.0 mmol) was dissolved in diethylcarbonate (35 mL). 1,1'-carbonyldiimidazole (3.4 g, 21 mmol) and sodium hydride (60% dispersion in mineral oil, 0.84 g, 21 mmol) was successively added. The resulting reaction mixture was stirred at 50° C. for 2 h and poured into ice water. The aqueous mixture was acidified with concentrated hydrochloric acid to pH 2 and extracted with ethyl acetate. The combined organic phase was washed with brine, dried and cencentrated. The residue was purified by chromatography on silica gel eluting with a 3:7 ethyl acetate:hexane containing 1% of acetic acid to afford Intermediate 4 as a white solid.

$^1$H NMR (500 MHz, CD$_3$OD) δ 7.37 (t, J=8.0 Hz, 1H), 7.30 (dd, J=7.5 Hz, 2.0 Hz, 1H), 7.23 (m, 1H), 7.20 (dd, J=8.0 Hz, 2.0 Hz, 1H), 7.13 (td, J=7.5 Hz, 1.5 Hz, 1H), 7.07 (t, J=2.5 Hz, 1H), 6.89 (dd, J=8.0 Hz, 1 Hz, 1H), 6.87 (m, 1H), 2.56 (t, J=7.5 Hz, 2H), 1.84 (s, 3H), 1.60 (m, 2H), 0.90 (t, J=7.5 Hz, 3H).

MS (ESI, m/z): 326.1 (M+1).

Intermediate 5

Step 1. Preparation of Ethyl (E)-2-ethyl-3-(3-benzyloxyphenyl)propenoate

A solution of 3-benzyloxybenzaldehyde (10 g, 50 mmol) and (1-carbethoxyethylene)triphenylphosphorane (20 g, 55 mmol) in THF (200 mL) was heated under reflux for 2 h. The reaction mixture was concentrated and the residue was triturated with 7:3 ethyl acetate:hexane and filtered through a short path of silica gel. Removal of the solvent from the filtrate gave the title product.

Step 2. Preparation of Ethyl (2R, 3R)-3-(3-benzyloxyphenyl)-2,3-dihydroxy-2-methylpropanoate A mixture of the product from step 1 (5.9 g, 20 mmol), AD-mix-α (Aldrich, 28.0 g) were mixed in 1:1 t-BuOH:H$_2$O (200 mL). The resulting mixture was stirred at 4° C. for 2 days and quenched by addition of an aqueous solution of Na$_2$SO$_3$ (2 N, 20 mL). The mixture was diluted with ethyl acetate (200 mL), washed with brine (2×100 mL) and dried. Removal of solvent gave the title compound.

$^1$H NMR (500 MHz, CDCl$_3$) δ 7.46 (m, 2H), 7.41(m, 2H), 7.36 (m, 1H), 7.29(t, J=8.4 Hz, 1H), 7.09(t, J=2.4 Hz, 1H), 7.01(d, J=8.4 Hz, 1H), 6.96 (dd, J=8.4, 2.4 Hz, 1H), 5.1 (s, 2H), 4.8(d, J=7.1 Hz, 1H), 4.3 (m, 2H), 3.50(s, 1H), 2.70 (d, J=7.1 Hz, 1H), 1.35 (t, J=7.5 Hz, 3H), 1.22 (s, 3H).

Step 3. Preparation of Ethyl (2R, 3R)-3-(3-benzyloxyphenyl)-2,3-dihydroxy-2-methylpropanoate 2,3-carbonate A solution of the product from step 2 (6.6 g, 20 mmol) and carbonyldiimidazole (6.5 g, 40 mmol) in toluene (100 mL) was heated at 60° C. for 1 h. After being cooled to room temperature, the reaction mixture was filtered through a short column of silica gel. The filter cake was washed with 3:7 ethyl acetate:hexane to give the title cyclic carbonate.

Step 4. Preparation of Ethyl (2R)-2-hydroxy-3-(3-hydroxyphenyl)-2-methylpropanoate A solution of the product from Step 3 (7.1 g, 20 mmol) in ethanol (100 mL) was stirred with 10% Pd/C (1.4 g) under hydrogen (1 atm) for 16 h. After removal of the catalyst, the solution was concentrated and the residue was chromatographed on silica gel eluting with 3:7 ethyl acetate:hexane to afford Intermediate 5.

$^1$H NMR (500 MHz, CDCl$_3$) δ 7.16 (t, J=8.4 Hz, 1H), 6.76 (m, 3H), 4.80 (br.s, 1H), 4.20 (m, 2H), 3.08 (d, J=15.0 Hz, 1H), 2.91 (d, J=15.0, 1H), 1.54 (s, 3H), 1.31 (t, J=7.2 Hz, 3H).

MS (ESI, m/z): 247.1 (M+Na$^+$).

Intermediate 6

To a solution of intermediate 5 (2.2 g, 10 mmol) and ethyldiisopropylamine (3.5 mL, 20 mmol) in dichloromethane (50 mL) cooled at −75° C. was added triflic anhydride (1.77 mL, 10.5 mmol). After being stirred for 30 min at −75° C., the reaction mixture was poured into water (50 mL) and extracted with dichloromethane (1×20 mL). The organic phase was washed with brine and concentrated. The residue was taken up in ether and filtered through short path of silica gel to give Intermediate 6.

$^1$H NMR (500 MHz, CD$_3$OD) δ 7.05 (t, J=8.5 Hz, 1H), 6.62-6.69 (m, 3H), 4.13 (m, 2H), 2.95 (d, J=13.5, 1H), 2.86 (d, J=13.5 Hz, 1H), 1.38 (s, 3H), 1.23 (t, J=7.5 Hz, 3H).

MS (ESI, m/z): 379.0 (M+Na$^+$)

Intermediate 7

The title intermediate was prepared following the same procedure as described for its enantiomer, intermediate 6, substituting AD-mix-β for AD-mix-α in step 2.

$^1$H NMR (500 MHz, CD$_3$OD) 7.05 (t, J=8.5 Hz, 1H), 6.62-6.69 (m, 3H), 4.13 (m, 2H), 2.95 (d, J=13.5, 1H), 2.86 (d, J=13.5 Hz, 1H), 1.38 (s, 3H), 1.23 (t, J=7.5 Hz, 3H).

MS (ESI, m/z): 379.0 (M+Na$^+$)

Intermediate 8

The title compound was prepared following the procedure as described for intermediate 4, steps 1 through 3, using intermediate 6 instead of intermediate 1 in step 1.

$^1$H NMR (500 MHz, CDCl$_3$) δ8.14 (br.s, 1H), 7.28 (m, 1H), 7.25 (t, J=7.9 Hz, 1H), 7.20 (m, 1H), 7.17 (m, 1H), 6.92 (d, J=7.6 Hz, 1H), 6.86 (m, 2H), 6.80 (d, J=1.6 Hz, 1H), 3.15 (d, J=14.3 Hz, 1H), 3.07 (d, J=14.3 Hz, 1H), 2.60 (t, J=7.6 Hz, 2H), 1.64 (m, 5H), 0.94 (t, J=7.6 Hz, 3H).

MS (ESI, m/z): 340.1 (M$^+$+1).

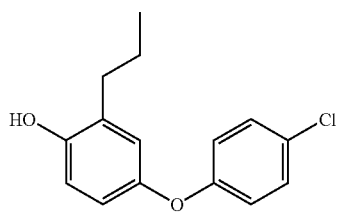

Intermediate 9

Step 1. Preparation of 4-chlorophenoxybenzaldehyde

A heterogeneous mixture of 4-chlorophenol (14.1 g, 0.11 mmol), 4-fluorobenzaldehyde 12.4 g, 0.1 mmol) and Cs$_2$CO$_3$ (65.0 g, 0.20 mmol) in DMF (400 mL) was stirred at 90° C. for 6 h. The reaction mixture was poured into water (1.2 L) and extracted with ethyl acetate (2×200 mL). The organic phase was washed with water (2×100 mL), dried and concentrated to give essentially pure 4-chlorophenoxybenzaldehyde, which was used directly for the next step.

Step 2. Preparation of 4-(4-chlorophenoxy)phenol

The crude aldehyde from step 1 (23.3 g, 0.10 mmol) was dissolved in dichloromethane (500 ml) and m-chloroperbenzoic acid (70%, 50.0 g, 0.20 mmol) and sodium bicarbonate (25.2 g, 0.30 mmol) was added. The resulting heterogeneous mixture was stirred and heated under reflux for 2 h and then quenched with an aqueous solution of sodium sulfite (0.5 M, 500 mL). After stirring at 25° C. for 30 min, the organic phase was separated and the aqueouse phase was extracted with dichloromethane (2×200 mL). The combine organic phase was washed with a saturated solution of sodium bicarbonate (2×200 mL), dried and concentrated. The residue was chromatographed on silica gel eluting with a 8:2 mixture of hexane and ethyl acetate to give the title phenol.

Step 3. Preparation of 3-[4-(4-chlorophenoxy)phenoxy]-1-propene

A mixture of the phenol from step 2 (16.5 g, 75 mmol), allyl bromide (10.8 g, 90 mmol) and cesium carbonate (48.7 g, 150 mmol) in DMF(300 mL) was stirred at 25° C. for 6 h. The mixture was poured into water (1.0 L) and extracted with ethyl acetate (2×200 mL). The combined organic phase was washed with water (3×100 mL), dried and concentrated. The crude product was used directly for the next step.

Step 4. Preparation of 4-(4-chlorophenoxy)-2-(2-propenyl)phenol

The crude allyl ether from step 3 (20.0 g) was dissolved in 2,4,6-trichlorobenzene (60 mL) and the solution was heated at reflux for 4 h. After being cooled to room temperature, the solution was directly loaded onto a column of silica gel and eluted sequentially with hexane and a 8:2 mixture of hexane and ethyl acetate to give 4-(4-chlorophenoxy)-2-(2-propenyl)phenol.

Step 5. Preparation of 4-(4-chlorophenoxy)-2-propylphenol

A mixture of the product from step 4 (15.7 g, 60 mmol) and 10% Pd/C (3.1 g) in ethyl acetate (300 mL) was stirred under hydrogen (1 atm). After the reaction was completed (ca. 30 min), the mixture was filtered through celite and the filtrate was concentrated to give Intermediate 8 as an oil which solidified upon standing.

$^1$H NMR (500 MHz, CDCl$_3$) δ 7.26 (d, J=8.5 Hz, 2H), 6.88 (d, J=8.5 Hz, 2H), 6.84 (m, 1H), 6.77 (m, 2H), 2.58 (t, J=7.5 Hz, 2H), 1.65 (m, 2H), 0.99 (t, J=7.5 Hz, 3H).

MS (ESI, m/z): 263.0 (M$^+$+1).

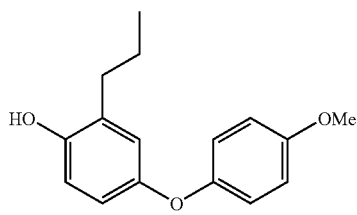

Intermediate 10

Intermediate 10 was prepared following the same procedure as described for Intermediate 9, steps 1 through 5, using 4-methoxyphenol instead of 4-chlorophenol in step 1.

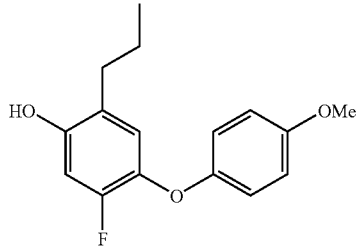

Intermediate 11

Intermediate 11 was prepared following the same procedure as described for intermediate 9, step 1 through 5, substituting 4-methoxyphenol for 4-chlorophenol and 3,4-difluorobenzaldehyde for 4-benzaldehyde in step 1.

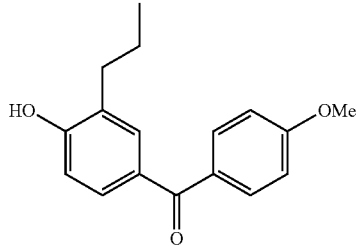

Intermediate 12

2-Propylphenol (13.6 g, 0.10 mol) and p-methoxybenzoic acid (22 g, 0.15 mol) were dissolved in triflic acid (200 mL). The resulting deep orange solution was stirred at 25° C. for 2 h. The reaction mixture was then diluted with ethyl acetate and poured slowly into ice. The organic layer was separated and washed successively with brine and aqueous NaHCO$_3$. After removal of the solvent, the residue was recrystallized from hexane-ether to give the title compound as a white solid.

$^1$H NMR (500 MHz, CDCl$_3$) δ7.82 (d, J=8.5 Hz, 2H), 7.66 (d, J=2.5 Hz, 1H), 7.59 (dd, J=8.5, 2.5 Hz, 1H), 6.99 (d, J=8.5 Hz, 2H), 6.86 (d, J=8.5 Hz, 1H), 3.92 (s, 3H), 2.65 (t, J=7.5 Hz, 2H), 1.70 (m, 2H), 1.00 (t, J=7.5 Hz, 3H).

MS (ESI, m/z): 271.0 (M$^+$+1).

Intermediate 13

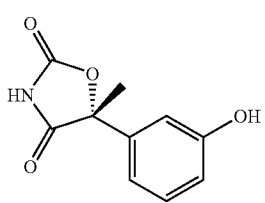

Step 1. (5R)-5-[3-(benzyloxy)phenyl]-5-methyl-1,3-oxazolidine-2,4-dione

A mixture of intermediate 3 (4.2 g, 20 mmol) benzyl bromide (3.7 g, 22 mmol) and Cs$_2$CO$_3$ (13 g, 9.75 g, 30 mmol) in DMF (100 mL) was stirred at room temperature for 6 h. The mixture was poured into water and extracted with diethyl ether. The organic phase was washed with water, dried over MgSO$_4$ and concentrated. The residue was sujected to the same procedure as described in step 2 and 3 for intermediate 4 to give the title product.

Step 2. (5R)-5-(3-hydroxyphenyl)-5-methyl-1,3-oxazolidine-2,4-dione

The product from step 1 ( ) in ethyl acetate ( ) was treated with 10% Pd/C under hydrogen (1 atm) for 1 h. The catalyst was removed by filtration and the fitrated was concentrated to give the title compound.

$^1$H NMR (500 MHz, CDCl$_3$) δ 7.28 (t, J=8.0 Hz, 1H), 7.05 (dt, J=8.0, 2.0 Hz, 1H), 6.98 (t, J=2 Hz, 1H), 6.82 (dt, J=8.0, 2.0 Hz, 1H), 5.25 (br. s, 1H), 1.89 (s, 3H).

MS (ESI, m/z): 208.2 (M+1).

Intermediate 14

Intermediate 14 was prepared following the same procedure as described for intermediate 13, using intermediate 5 as the starting material in stead of intermediate 3 in step 1.

$^1$H NMR (500 MHz, CDCl$_3$) δ 7.18 (t, J=8.0 Hz, 1H), 7.0 (m, 1H), 6.78 (t, J=2 Hz, 1H), 6.72 (m, 1.0 Hz, 1H), 5.50 (br. s, 1H), 3.16 (d, J=14.3 Hz, 1H), 3.17 (d, J=14.3 Hz, 1H), 1.90 (s, 3H).

MS (ESI, m/z): 224.2 (M+1).

Example 1

(5R)-5-{3-[4-(4-Methoxybenzoyl)-2-propylphenoxy]phenyl}-5-methyl-1,3-oxazoline-2,4-dione

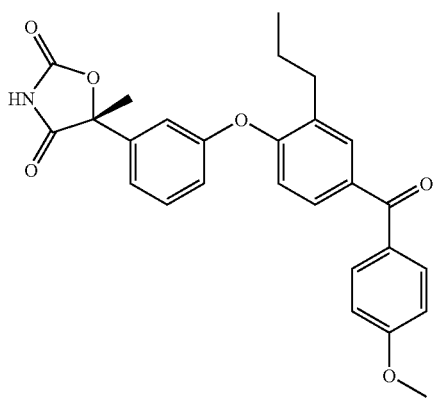

Step 1. Preparation of 3-[4-(4-methoxybenzoyl)-2-propylphenoxy]acetophenone

A mixture of intermediate 12 (2.7 g, 10 mmol), 3-acetylphenylboronic acid (4.9 g, 30 mmol), copper acetate (2.7 g, 1.5 mmol), triethylamine (6.8 mL, 50 mmol) and 4Å molecular sieves (7 g) in dichloromethane (80 mL) was stirred at 25° C. under air. After 16 h, the reaction mixture was diluted with diethyl ether (240 mL) and filtered through a short path of silica gel. The filtrated was concentrated and the residue was purified by chromatography on silica gel eluting with 1:9 ethyl acetate:hexane to afford the title compound.

Step 2. Preparation of (2R/S)-2-hydroxy-2-{3-[4-(4-methoxybenzoyl)-2-propylphenoxy]phenyl}propionamide To a solution of the product from step 1 (1.9 g, 5.0 mmol) and a catalytic amount of zinc iodide (80 mg, 0.25 mmol) in dichloromethane (50 mL) was added trimethylsilyl cyanide (1.3 mL, 10 mmol). After 1 h at 25° C., the reaction mixture was concentrated and the residue was dissolved in 1:1 dioxane:concentrated hydrochloric acid (100 mL). The resulting solution was saturated with gaseous hydrogen chloride and left at 25° C. for 1 h. The reaction was diluted with ethyl acetate and washed successively with brine and saturated aqueous sodium bicarbonate. Removal of the solvent from the organic phase gave a residue which was purified by chromatography on silica gel eluting first with 2:8 ethyl acetate:hexane and then with 100% ethyl acetate. The ethyl acetate fraction was concentrated to afford the title compound.

Step 3. Chiral Separation of the Product from Step 2

Using a preparative Chiracel OJ column, the product from step 2 was separated by chiral HPLC eluting with 1:1 ethanol:heptane. The early and late fractions contained (2S)-and (2R)-enantiomer respectively.

Step 4. Preparation of (5R)-5-{3-[4-(4-Methoxybenzoyl)-2-propylphenyl}-5-methyl-1,3-oxazoline-2,4-dione The (2R)-enantimer from step 3 (0.43 g, 1.0 mmol) was dissolved in diethylcarbonate (5 mL). 1,1'-carbonyldiimidazole (0.49 g, 3 mmol) and sodium hydride (60% dispersion in mineral oil, 0.12 g, 3 mmol) was successively added. The resulting reaction mixture was stirred at 50° C. for 1 h and then poured into ice water. The aqueous mixture was acidified with concentrated hydrochloric acid to pH 2 and extracted with ethyl acetate. The combined organic phase was washed with brine, dried and cencentrated. The residue was purified by preparative reverse-phase HPLC to give the title compound.

$^1$H NMR (500 MHz, CD$_3$OD) δ 7.80 (d, J=8.5 Hz, 2H), 7.71 (d, J=2.5 Hz, 1H), 7.58 (dd, J=8.5 Hz, 2 Hz, 1H), 7.47 (t, J=9.0 Hz, 1H), 7.36 (d, J=9.0 Hz, 1H), 7.20 (t, J=2.0 Hz, 1H), 7.06 (d, J=8.5 Hz, 2H), 7.05 (dd, J=7.0 Hz, 2.0 Hz, 1H), 6.91 (d, J=8.5 Hz, 1H), 3.90 (s, 1H), 2.71 (t, J=8.5 Hz, 2H), 1.88 (s, 3H), 1.71 (m, 2H), 0.97 (t, J=8.5 Hz, 3H).

MS (ESI, m/z): 459.9 (M+1).

Example 2

(5S)-5-{3-[4-(4-Methoxybenzoyl)-2-propylphenoxy]phenyl}-5-methyl-1,3-oxazoline-2,4-dione

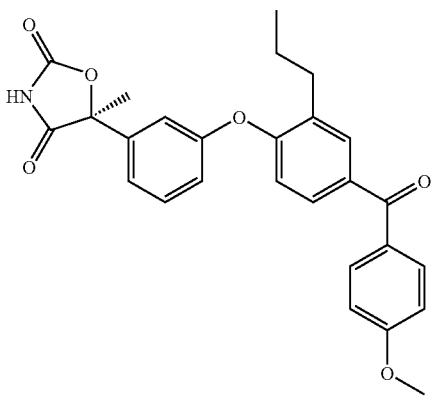

Using the procedure of Example 1, step 4, the title compound was prepared from (5S)-2-hydroxy-2-{3-[4-(4-methoxybenzoyl)-2-propylphenoxy]phenyl}propionamide, which was obtained as the early fraction from the chiral separation described in Example 1, step 3.

$^1$H NMR (500 MHz, CD$_3$OD) δ 7.80 (d, J=8.5 Hz, 2H), 7.71 (d, J=2.5 Hz, 1H), 7.58 (dd, J=8.5 Hz, 2 Hz, 1H), 7.47 (t, J=9.0 Hz, 1H), 7.36 (d, J=9.0 Hz, 1H), 7.20 (t, J=2.0 Hz, 1H), 7.06 (d, J=8.5 Hz, 2H), 7.05 (dd, J=7.0 Hz, 2.0 Hz, 1H), 6.91 (d, J=8.5 Hz, 1H), 3.90 (s, 1H), 2.71 (t, J=8.5 Hz, 2H), 1.88 (s, 3H), 1.71 (m, 2H), 0.97 (t, J=8.5 Hz, 3H).

MS (ESI, m/z): 459.9 (M+1).

Example 3

(5R)-5-{3-[4-(4-Chlorobenzoyl)-2-propylphenoxy]phenyl}-5-methyl-1,3-oxazolidine-2,4-dione

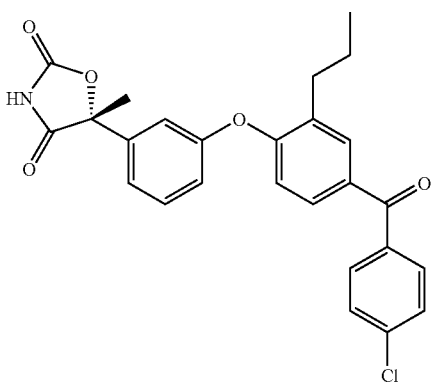

Intermediate 4 (0.33 g, 1.0 mmol) and p-chlorobenzoic acid (0.24 g, 1.5 mmol) were dissolved in triflic acid (3.0 mL). The resulting deep orange solution was stirred at 25° C. for 2 h. The reaction mixture was then diluted with ethyl acetate and poured slowly into ice. The organic layer was separated and washed successively with brine and aqueous NaHCO$_3$. After removal of the solvent, the residue was purified by preparative reverse-phase HPLC to give the title compound.

$^1$H NMR (500 MHz, CD$_3$OD) δ7.74 (d, J=8.4 Hz, 2H), 7.73 (d, J=2.4 Hz, 1H), 7.56 (dd, J=8.4, 2.4 Hz, 1H), 7.53 (t, J=8.4 Hz, 2H), 7.35-7.40 (m, 2H), 7.21 (t, J=1.8 Hz, 1H), 6.95 (ddd, J=8.4, 2.4, 1.8 Hz, 1H), 6.84 (d, J=8.4 Hz, 1H), 2.72 (t, J=7.2 Hz, 2H), 1.71 (s, 3H), 1.69 (m, 2H), 1.96 (t, J=7.2 Hz, 3H).

MS (ESI, m/z): 463.9 (M$^+$+1).

The title compounds of Example 4 through Example 19 were prepared following the procedure from Example 3, replacing 4-chlorobenzoic acid with a corresponding aromatic acid.

Example 4

(5R)-5-{3-[4-(2-hydroxy-4-methoxybenzoyl)-2-propylphenoxy]phenyl}-5-methyl-1,3-oxazolidine-2,4-dione

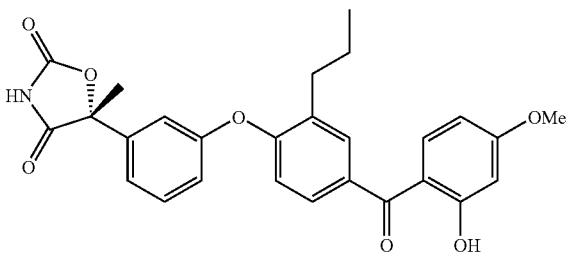

$^1$H NMR (500 MHz, CDCl$_3$) δ 8.40 (br. s, 1H), 7.60 (d, J=2.5 Hz, 1H), 7.57 (d, J=9.0 Hz, 1H), 7.47 (dd, J=8.4, 2.5 Hz, 1H), 7.41 (t, J=8.4 Hz, 1H), 7.35 (m, 1H), 7.30 (t, J=2.5 Hz, 1H), 6.99 (dd, J=8.4, 2.5 Hz, 1H), 6.86 (d, J=8.4 Hz, 1H), 6.54 (d, J=2.5 Hz, 1H), 6.45(dd, J=9.0, 2.5 HZ, 1H), 3.89 (s, 3H), 2,70 (t, J=7.5 Hz, 2H), 1.94 (s, 3H), 1.70 (m, 2H), 0.98 (t, J=7.5 Hz, 3H).

MS (ESI, m/z): 476.0 (M$^+$+1).

Example 5

(5R)-5-{3-[4-(2-hydroxy-4-chlorobenzoyl)-2-propylphenoxy]phenyl}-5-methyl-1,3-oxazolidine-2,4-dione

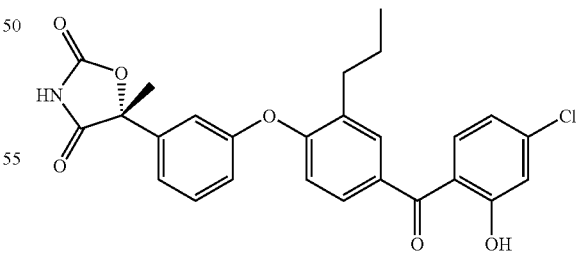

$^1$H NMR (500 MHz, CDCl$_3$) δ 7.56 (d, J=2.5 Hz, 1H), 7.53 (d, J=9.0 Hz, 1H), 7.44 (dd, J=8.4, 2.5 Hz, 1H), 7.29 (t, J=8.4 Hz, 1H), 7.22-7.27 (m, 2H), 7.08 (d, J=2.5 Hz, 1H), 6.89 (m, 1H), 6.86 (dd, J=8.4, 2.5 Hz, 1H), 6.78 (d, J=8.5 Hz, 1H), 2,68 (t, J=7.5 Hz, 2H), 1.70 (s, 3H), 1.66 (m, 2H), 0.95 (t, J=7.5 Hz, 3H).

MS (ESI, m/z): 480.0 (M$^+$+1).

Example 6

(5R)-5-{3-{4-[4-(trifluoromethoxy)benzoyl]-2-propylphenoxy}phenyl}-5-methyl-1,3-oxazolidine-2,4-dione

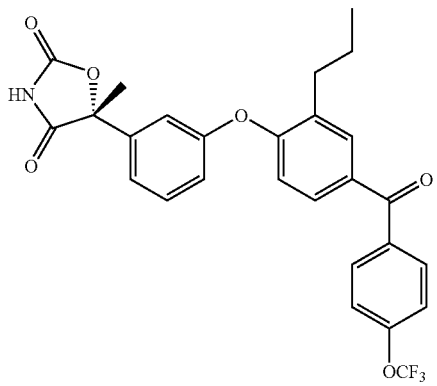

$^1$H NMR (500 MHz, CD$_3$OD) δ 7.89 (d, J=8.5 Hz, 2H), 7.77 (d, J=2.5 Hz, 1H), 7.60 (dd, J=8.5, 2.5 Hz, 1H), 7.47 (t, J=8.5 Hz, 1H), 7.44 (d, J=8.5 Hz, 2H), 7.37 (m, 1H), 7.21 (t, J=2.5 Hz, 1H), 7.05 (dd, J=8.5, 2.5 Hz, 1H), 6.89 (d, J=8.5 Hz, 1H), 2.71 (t, J=7.5 Hz, 2H), 1.87 (s, 3H), 1.69 (m, 2H), 0.96 (s, 3H).

MS (ESI, m/z): 513.9 (M$^+$+1).

Example 7

(5R)-5-{3-[4-(2,4-dimethoxybenzoyl)-2-propylphenoxy]phenyl}-5-methyl-1,3-oxazolidine-2,4-dione

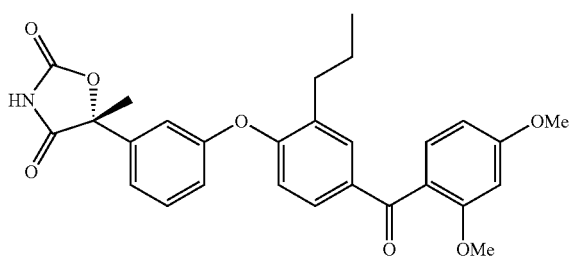

$^1$H NMR (500 MHz, CDCl$_3$) δ 8.2 (br. s, 1H), 7.74 (d, J=2.5 Hz, 1H), 7.58 (dd, J=8.5, 2.5 Hz, 1H), 7.38-7.42 (m, 2H), 7.34 (m, 1H), 7.26 (m, 1H), 6.97 (dd, 8.5, 2.5 Hz, 1H), 6.78 (d, J=8.5 Hz, 1H), 6.56 (dd, J=8.5, 2.5 Hz, 1H), 6.52 (d, J=2.5 Hz, 1H), 3.89 (s, 3H), 3.74 (s, 3H), 2.67 (t, J=7.5 Hz, 2H), 1.94 (s, 3H), 1.66 (m, 2H), 0.96 (t, J=7.5 Hz, 3H).

MS (ESI, m/z): 490.0 (M$^+$+1)

Example 8

(5R)-5-{3-[4-(4-difluoromethoxybenzoyl)-2-propylphenoxy]phenyl}-5-methyl-1,3-oxazolidine-2,4-dione

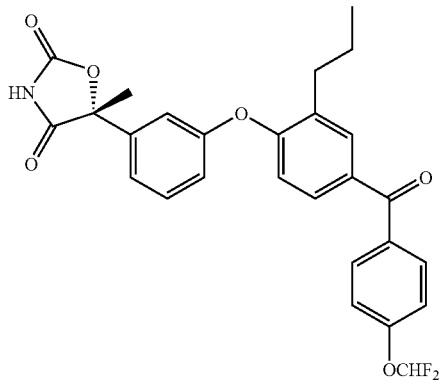

$^1$H NMR (500 MHz, CDCl$_3$) δ 8.5 (br. s, 1H), 7.87 (d, J=8.5 Hz, 2H), 7.76 (d, J=2.5, Hz, 1H), 7.60 (dd, J=8.5, 2.5 Hz, 1H), 7.44 (t, J=8.5 Hz, 1H), 7.39 (m, 1H), 7.31(t, J=2.5 Hz, 1H), 7.25 (d, J=8.5 Hz, 2H), 7.02 (m, 1H), 6.85 (d, J=8.5 Hz, 1H), 6.64 (t, J=70.0 Hz, 1H), 2.72 (t, J=7.5 Hz, 2H), 1.97 (s, 3H), 1.71 (m, 2H), 0.99 (t, J=7.5 Hz, 3H).

MS (ESI, m/z): 495.9 (M$^+$+1)

Example 9

(5R)-5-{3-[4-(4-Chloro-2-fluorobenzoyl)-2-propylphenoxy]phenyl}-5-methyl-1,3-oxazolidine-2,4-dione

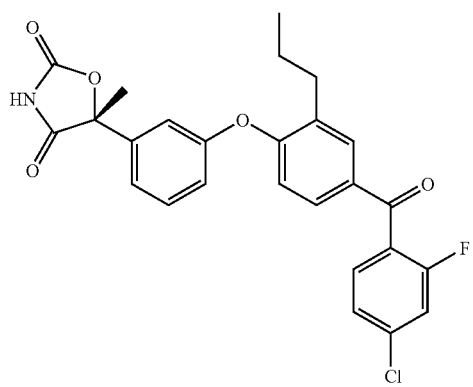

$^1$H NMR (500 MHz, CDCl$_3$) δ 7.89 (br.s, 1H), 7.79 (s, 1H), 7.61 (d, J=8.0 Hz, 1H), 7.53 (t, J=8.0 Hz, 1H), 7.45 (t, J=8.0 Hz, 1H), 7.39 (d, J=8.0 Hz, 1H), 7.31 (s, 1H), 7.29 (s, 1H), 7.23 (dd, J=8.5 Hz, 2.0 Hz, 1H), 7.02 (d, J=7.5 Hz, 1H), 6.80 (d, J=7.5 Hz, 1H), 2.72 (t, J=7.5 Hz, 2H), 1.96 (s, 3H), 1.70 (m, 2H), 0.99 (t, J=7.5 Hz, 3H).

MS (ESI, m/z): 481.9 (M+1).

Example 10

(5R)-5-{3-[4-(2-fluoro-4-methoxybenzoyl)-2-propylphenoxy]phenyl}-5-methyl-1,3-oxazolidine-2,4-dione

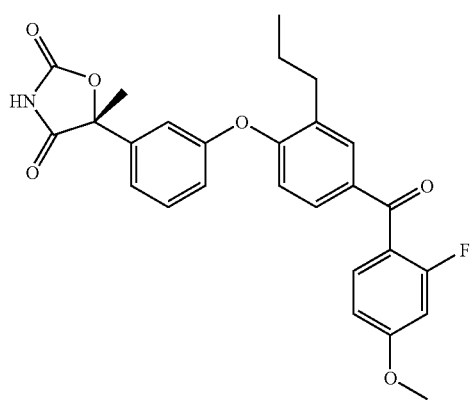

¹H NMR (500 MHz, CDCl₃) δ 7.78 (br.s, 1H, 1H), 7.62 (m, 1H), 7.59 (t, J=8.5 Hz, 1H), 7.43 (t, J=8.0 Hz, 1H), 7.37 (m, 1H), 7.31 (t, J=2.0 Hz, 1H), 7.01 (m, 1H), 6.82 (d, J=8.5 Hz, 1H), 6.70 (dd, J=12.0 Hz, 2.0 Hz, 1H), 3.91 (s, 3H), 2.71 (t, J=7.5 Hz, 2H), 1.96 (s, 3H), 1.70 (m, 2H), 0.99 (t, J=7.5 Hz, 3H).

MS (ESI, m/z): 478.0 (M+1).

Example 11

(5R)-5-{3-[4-(4-methylbenzoyl)-2-propylphenoxy]phenyl}-5-methyl-1,3-oxazolidine-2,4-dione

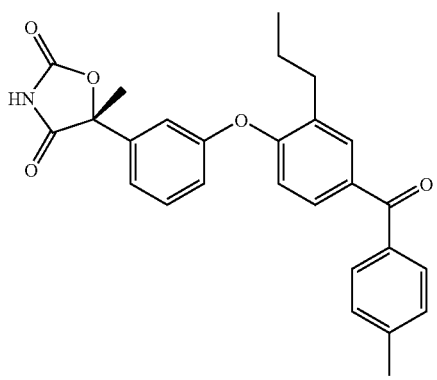

¹H NMR (500 MHz, CDCl₃) δ 7.77 (d, J=2.0 Hz, 1H), 7.74 (d, J=8.0 Hz, 2H), 7.62 (dd, J=8.5 Hz, 2.5 Hz, 1H), 7.43 (t, J=8.0 Hz, 1H), 7.37 (d, J=8.0 Hz, 1H), 7.32 (d, J=2.0 Hz, 1H), 7.32 (d, J=8.0 Hz, 2H), 7.01 (m, 1H), 6.85 (d, J=8.5 Hz, 1H), 2.72 (t, J=7.5 Hz, 2H), 2.47 (s, 3H), 1.97 (s, 3H), 1.70 (m, 2H), 0.99 (t, J=7.5 Hz, 3H).

MS (ESI, m/z): 444.0 (M+1).

Example 12

(5R)-5-{3-[4-(3-methoxybenzoyl)-2-propylphenoxy]phenyl}-5-methyl-1,3-oxazolidine-2,4-dione

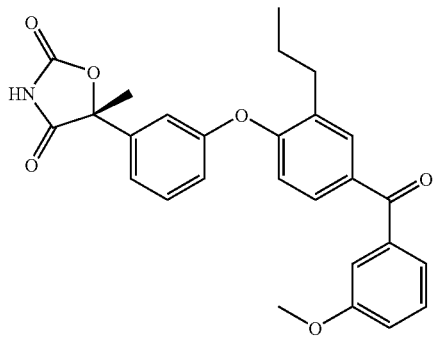

¹H NMR (500 MHz, CDCl₃) δ 8.27 (br.s, 1H), 7.80 (d, J=2.0 Hz, 1H), 7.64 (dd, J=6.5 Hz, 2 Hz, 1H), 7.45-35 (m, 5H), 7.32 (t, J=2.0 Hz, 1H), 7.16 (dt, J=8.0 Hz, 1.0 Hz, 1H), 7.03 (dd, J=6.0 Hz, 2.5 Hz, 1H), 6.71 (t, J=8.5 Hz, 1H), 3.89 (s, 3H), 2.72 (t, J=7.5 Hz, 2H), 1.97 (s, 3H), 1.71 (m, 2H), 0.99 (t, J=7.5 Hz, 3H).

MS (ESI, m/z): 460.0 (M+1).

Example 13

(5R)-5-{3-[4-(2,4-dichlorobenzoyl)-2-propylphenoxy]phenyl}-5-methyl-1,3-oxazolidine-2,4-dione

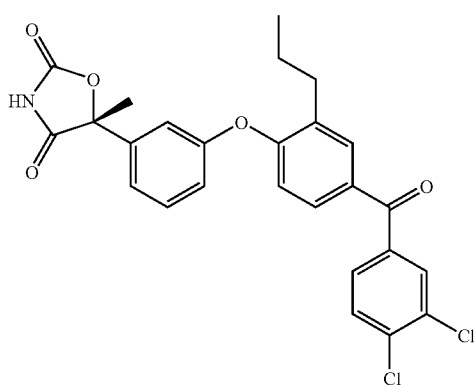

¹H NMR (500 MHz, CDCl₃) δ 7.98 (br.s, 1H), 7.93 (d, J=2.0 Hz, 1H), 7.78 (d, J=2.5 Hz, 1H), 7.67 (dd, J=6.5 Hz, 2.0 Hz, 1H), 7.62 (d, J=8.0 Hz, 1H), 7.61 (dd, J=8.0 Hz, 2.0 Hz, 1H), 7.47 (d, J=8.0 Hz, 1H), 7.42 (d, J=8.0 Hz, 1H), 7.34 (t, J=2.0 Hz, 1H), 7.06 (dd, J=8.0 Hz, 1 Hz, 1H), 6.86 (d, J=8.5 Hz, 1H), 2.76 (t, J=7.5 Hz, 2H), 1.99 (s, 3H), 1.73 (m, 2H), 1.02 (t, J=7.5 Hz, 3H).

MS (ESI, m/z): 497.9 (M+1).

Example 14

(5R)-5-{3-[4-(4-Ethoxybenzoyl)-2-propylphenoxy]phenyl}-5-methyl-1,3-oxazolidine-2,4-dione

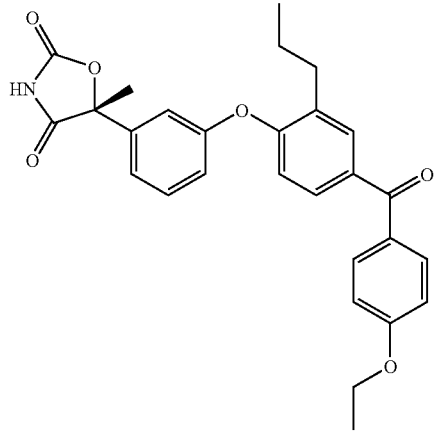

$^1$H NMR (500 MHz, CDCl$_3$) δ 7.99 (br.s, 1H), 7.86 (d, J=8.5 Hz, 2H), 7.76 (d, J=2.5 Hz, 1H), 7.61 (dd, J=6.5 Hz, 2 Hz, 1H), 7.45 (t, J=8.0 Hz, 1H), 7.39 (d, J=8.5 Hz, 1H), 7.33 (t, J=2.0 Hz, 1H), 7.03 (dd, J=9.0 Hz, 1.5 Hz, 1H), 7.00 (d, J=9.0 Hz, 2H), 6.87 (d, J=8.5 Hz, 1H), 4.17 (q, J=7.0 Hz, 2H), 2.73 (t, J=7.5 Hz, 2H), 1.99 (s, 3H), 1.72 (m, 2H), 1.50 (t, J=7.0 Hz, 3H), 1.01 (t, J=7.5 Hz, 3H).

MS (ESI, m/z): 474.0 (M+1).

Example 15

(5R)-5-{3-{4-[4-fluoro-3-(trifluoromethyl)benzoyl]-2-propylphenoxy}phenyl}-5-methyl-1,3-oxazolidine-2,4-dione

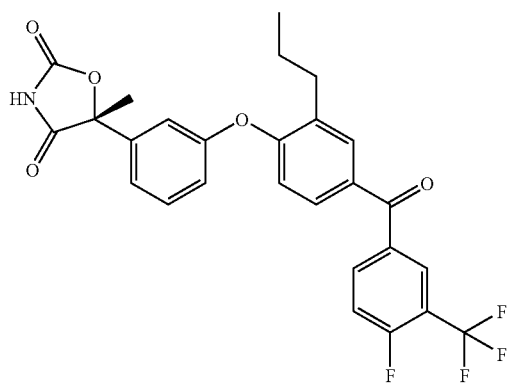

$^1$H NMR (500 MHz, CDCl$_3$) δ 8.12 (dd, J=7.0 Hz, 2Hz, 1H), 8.05 (m, 1H), 7.83 (br.s, 1H), 7.76 (d, J=2.5 Hz, 1H), 7.58 (dd, J=8.5 Hz, 2.5 Hz, 1H), 7.46 (t, J=8.0 Hz, 1H), 7.36 (d, J=9.0 Hz, 1H), 7.05 (m, 1H), 6.85 (d, J=8.5 Hz, 2H), 2.75 (t, J=7.5 Hz, 2H), 1.97 (s, 3H), 1.72 (m, 2H), 1.01 (t, J=7.5 Hz, 3H).

MS (ESI, m/z): 515.9 (M+1).

Example 16

(5R)-5-{3-[4-(3-fluoro-4-methoxybenzoyl)-2-propylphenoxy]phenyl}-5-methyl-1,3-oxazolidine-2,4-dione

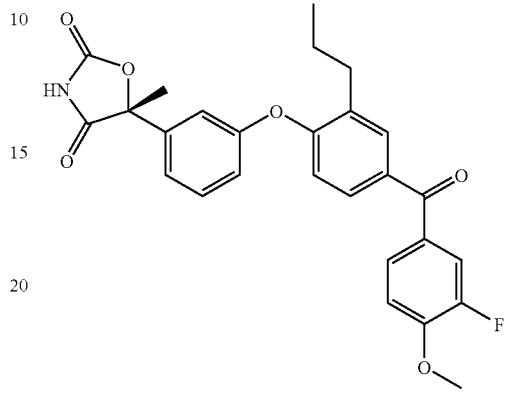

$^1$H NMR (500 MHz, CDCl$_3$) δ 7.82 (br.s, 1H), 7.75 (d, J=2.5 Hz, 1H), 7.64 (d, J=9.0 Hz, 2H), 7.58 (dd, J=8.0 Hz, 2.0 Hz, 1H), 7.44 (t, J=8.0 Hz, 1H), 7.38 (dd, J=8.5 Hz, 1.5 Hz, 1H), 7.32 (t, J=2.0 Hz, 1H), 7.06 (t, J=8.0 Hz, 1H), 7.02 (dd, J=8.0 Hz, 2.5 Hz, 1H), 6.86 (d, J=8.5 Hz, 1H), 4.01 (s, 3H), 2.73 (t, J=7.5 Hz, 2H), 1.97 (s, 3H), 1.71 (m, 2H), 1.00 (t, J=7.5 Hz, 3H).

MS (ESI, m/z): 478.0 (M+1).

Example 17

(5R)-5-{3-[4-(4-methylthiobenzoyl)-2-propylphenoxy]phenyl}-5-methyl-1,3-oxazolidine-2,4-dione

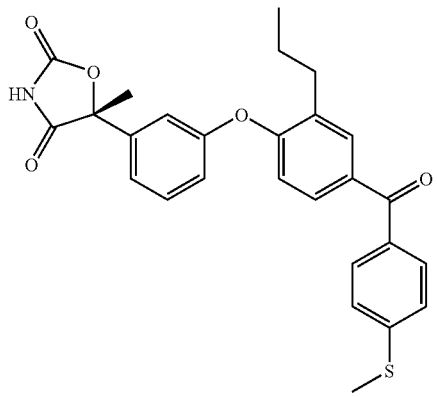

$^1$H NMR (500 MHz, CDCl$_3$) δ 7.91 (br.s, 1H), 7.77 (d, J=7.5 Hz, 2H), 7.76 (d, J=2.0 Hz, 1H), 7.61 (dd, J=7.5 Hz, 2 Hz, 1H), 7.44 (t, J=8.0 Hz, 1H), 7.39 (dd, J=8.0 Hz, 1.5 Hz, 1H), 7.33 (d, J=8.5 Hz, 2H), 7.31 (t, J=2.0 Hz, 1H), 7.02 (m, 1H), 6.85 (d, J=8.5 Hz, 1H), 2.72 (t, J=8.0 Hz, 2H), 2.57 (s, 3H), 1.97 (s, 3H), 1.71 (m, 2H), 0.99 (t, J=8.0 Hz, 3H).

MS (ESI, m/z): 475.9 (M+1).

Example 18

(5R)-5-{3-[4-(4-methanesulfonylbenzoyl)-2-propylphenoxy]phenyl}-5-methyl-1,3-oxazolidine-2,4-dione

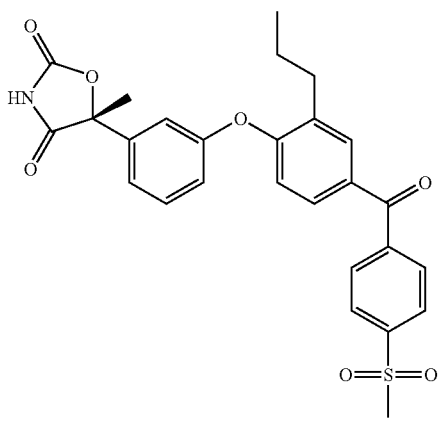

$^1$H NMR (500 MHz, CDCl$_3$) δ 8.11 (d, J=8.5 Hz, 2H), 8.02 (br.s, 1H), 7.96 (d, J=8.5 Hz, 2H), 7.79 (d, J=2.0 Hz, 1H), 7.61 (dd, J=8.5 Hz, 2.5 Hz, 1H), 7.46 (d, J=8.0 Hz, 1H), 7.41 (m, 1H), 7.32 (t, J=2.0 Hz, 1H), 7.05 (m, 1H), 6.84 (d, J=8.5 Hz, 1H), 3.15 (s, 3H), 2.75 (t, J=8.0 Hz, 2H), 1.97 (s, 3H), 1.71 (m, 2H), 1.01 (t, J=8.0 Hz, 3H).

MS (ESI, m/z): 507.9 (M+1).

Example 19

(5R)-5-{3-[4-(2-methoxy-5-pyridyl)-2-propylphenoxy]phenyl}-5-methyl-1,3-oxazolidine-2,4-dione

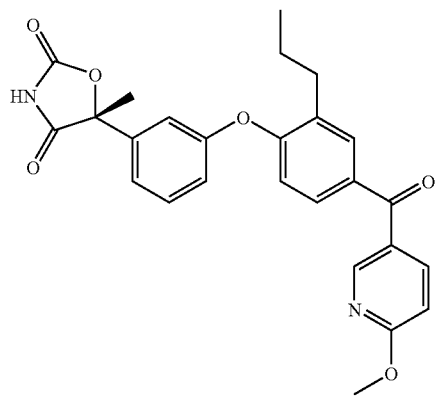

$^1$H NMR (500 MHz, CDCl$_3$) δ 8.60 (s, 1H), 8.26 (d, J=8.5 Hz, 1H), 7.78 (s, 1H), 7.61 (d, J=8.0 Hz, 1H), 7.45 (t, J=8.0 Hz, 1H), 7.39 (d, J=7.0 Hz, 1H), 7.30 (s, 2H), 7.04 (d, J=7.5 Hz, 1H), 6.87 (d, J=8.5 Hz, 1H), 4.10 (s, 3H), 2.74 (t, J=7.5 Hz, 2H), 1.97 (s, 3H), 1.72 (m, 2H), 1.00 (t, J=7.5 Hz, 3H).

MS (ESI, m/z): 460.9 (M+1).

Example 20

(5R)-5-{3-[2-(Cyclopropylmethyl)-4-(4-methoxybenzoyl)phenoxy]phenyl}-5-methyl-1,3-oxazolidine-2,4-dione

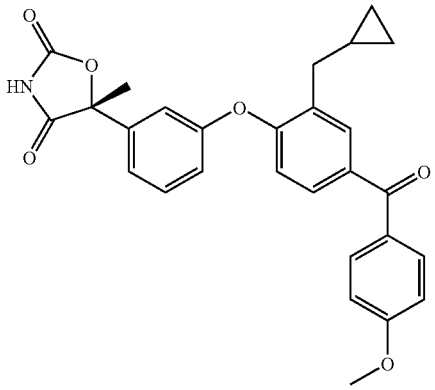

Step 1. Preparation 4-fluoro-4'-methoxybenzophenone Dimethyl Ketal

4-Fluoro-4'-methoxybenzophenone (2.3 g, 10 mmol), trimethyl orthoformate (10.6 g, 100 mmol), anhydrous methanol (3.2 g, 100 mmol) and triflic acid (0.17 mL, 2.0 mmol) were mixed in dry acetonitrile (16 mL). After being kept at 25° C. for 6 h, the reaction was quenched with ethyldiisopropylamine (1.7 mL) and concentrated. The residue was taken up in 2:8 ethyl acetate and filtered through a short path of silica gel to give the title compound.

Step 2. Preparation of 4-fluoro-3-formyl-4'-methoxybenzophenone Dimethyl Ketal

To a solution of 2,2,6,6-tetramethylpiperidine (2.6 g, 20 mmol) in THF (100 mL) cooled at 0° C. was added n-butyllithium (1.6 M in hexane, 12.5 mL, 20 mmol). The resulting solution was cooled to −75 C and the product from step 1(2.8 g, 10 mmol) in THF (10 mL) was added. After being kept at −75 C for 1.5 h, the reaction mixture was quenchhed with dimethylformamide (2.2 g, 30 mmol) and warmed to to 0° C. The mixture was poured into hydrochloric acid (2 N, 100 mL) and extracted with ethyl acetate. After removal of the solvent, the residue was purified by chromatography on silica gel eluting with 1:9 ethyl acetate:hexane afforded the title compound.

Step 3. Preparation of (2R)-2-{3-[2-formyl-4-(4-methoxybenzoyl)phenoxy]phenyl}-2-hydroxypropanoate A mixture of the product from step 2 (2.2 g, 10 mmol), intermediate 3 (2.4 g, 10 mmol) and Cs$_2$CO$_3$ (5.9 g, 18 mmol) in DMF (80 mL) was heated at 80° C. for 2 h. The reaction mixture was poured into water (200 mL) and extracted with ethyl acetate (2×100 mL). Removal of the solvent and chromatography of the residue on silica gel eluting with 3:7 ethyl acetate:hexane gave the title product.

Step 4. Preparation of (2R)-2-{3-[2-(cyclopropylmethyl)-4-(4-methoxybenzoyl)phenoxy]phenyl}-2-hydroxypropanoate To a solution of the product from step 3 (0.43g, 1.0 mmol) in THF (10 mL) cooled at −75° C. was added cyclopropylmethylmagnesium bromide (1.0 M in Et$_2$O, 2.5 mL, 2.5 mmol). The reaction mixture was ketp at −75° C. for 1 h and quenched with saturated aqueous ammonium chloride (20 mL). The organic phase was separated and the aqueous phase was extracted with ethyl acetate (2×10 mL). The combined organic phase was washed with brine, dried and concentrated. The residue was dissolved in dichloromethane (5.0 mL), cooled to 0° and treated with triethylsilane (1.6 g, 10 mmol) and trifluoroacetic acid (0.23 mL, 3.0 mmol). After 30 min at 0° C., the mixture was poured slowly into a saturated solution aqueous sodium bicarbonate (10 mL) and extracted with dichloromethane. The crude product was purified by chromatography on silica gel eluting with 3:7 ethyl acetate:hexane to afford the title compound.

Step 5. Preparation of (5R)-5-{3-[2-(cyclopropylmethyl)-4-(4-methoxybenzoyl)phenoxy]phenyl}-5-methyl-1,3-oxazolidine-2,4-dione The product of step 4 was converted to the title compound following the same procedure as described for intermediate 4, steps 2 and 3.

$^1$H NMR (500 MHz, CDCl$_3$) δ 8.41 (br.s, 1H), 7.89 (d, J=2.5 Hz, 1H), 7.87 (d, J=7.5 Hz, 2H), 7.62 (dd, J=7.5 Hz, 2.5 Hz, 1H), 7.42 (t, J=8.0 Hz, 1H), 7.37 (d, J=8.5 Hz, 1H), 7.31 (t, J=2.0 Hz, 1H), 7.01 (m, 1H), 7.00 (d, J=8.5 Hz, 2H), 6.86 (d, J=8.5 Hz, 1H), 3.92 (s, 3H), 2.66 (d, J=7.5 Hz, 2H), 1.96 (s, 3H), 1.08 (m, 1H), 0.54 (m, 2H), 0.24 (m, 2H).

MS (ESI, m/z): 472.0 (M+1).

Example 21

(5R)-5-{3-[4-(2-fluoro-4-methoxybenzoyl)-2-propylphenoxy]benzyl}-5-methyl-1,3-oxazolidine-2,4-dione

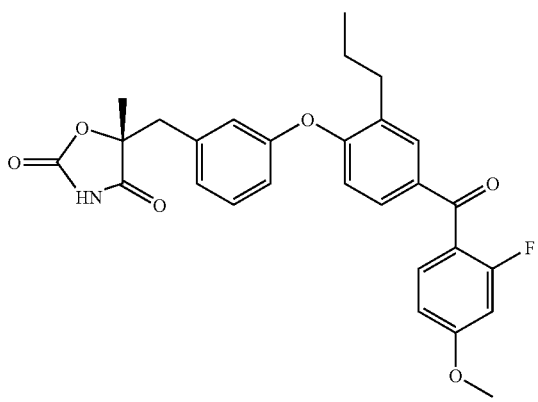

Intermediate 8 (0.35 g, 1.0 mmol) and 2-fluoro-4-methoxybenzoic acid (0.26 g, 1.5 mmol) were dissolved in triflic acid (3.0 mL). The resulting deep orange solution was stirred at 25° C. for 2 h. The reaction mixture was then diluted with ethyl acetate and poured slowly into ice. The organic layer was separated and washed successively with brine and aqueous NaHCO$_3$. After removal of the solvent, the residue was purified by preparative reverse-phase HPLC to give the title compound.

$^1$H NMR (500 MHz, CDCl$_3$) δ 7.76 (br.s, 1H, 1H), 7.61 (m, 1H), 7.58 (t, J=8.5 Hz, 1H), 7.32 (t, J=8.0 Hz, 1H), 7.04 (m, 1H), 6.97 (m, 1H), 6.91 (m, 1H), 6.81 (dd, J=8.5, 2.5 Hz, 1H), 6.75 (d, J=8.5 Hz, 1H), 6.69 (dd, J=12.0, 2.5 Hz, 1H), 3.20 (d, J=14.5, 1H), 3.11 (d, J=14.5 Hz, 1H), 2.7 (t, J=7.5 2H), 1.71 (m, 2H), 1.70 (s, 3H), 0.99 (t, J=7.5 Hz, 3H).

MS (ESI, m/z): 492.0 (M+1).

The title compounds of Examples 22-24 were prepared following the procedure of Example 21, replacing 2-fluoro-4-methoxybenzoic acid with the appropriate aromatic acid.

Example 22

(5R)-5-{3-[4-(4-Chloro-2-fluorobenzoyl)-2-propylphenoxy]benzyl}-5-methyl-1,3-oxazolidine-2,4-dione

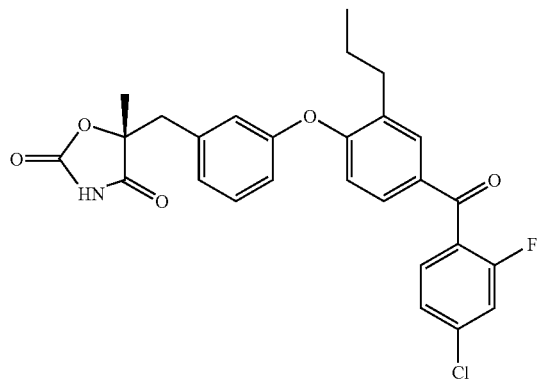

$^1$H NMR (500 MHz, CDCl$_3$) δ 7.76 (br. s, 1H, 1H), 7.61 (m, 1H), 7.58 (t, J=8.5 Hz, 1H), 7.32 (t, J=8.0 Hz, 1H), 7.04 (m, 1H), 6.97 (m, 1H), 6.91 (m, 1H), 6.81 (dd, J=8.5, 2.5 Hz, 1H), 6.75 (d, J=8.5 Hz, 1H), 6.69 (dd, J=12.0, 2.5 Hz, 1H), 3.20 (d, J=14.5, 1H), 3.11 (d, J=14.5 Hz, 1H), 2.7 (t, J=7.5 2H), 1.71 (m, 2H), 1.70 (s, 3H), 0.99 (t, J=7.5 Hz, 3H).

MS (ESI, m/z): 496.1 (M$^+$+1)

Example 23

(5R)-5-{3-[4-(4-Chloro-2-hydroxybenzoyl)-2-propylphenoxy]benzyl}-5-methyl-1,3-oxazolidine-2,4-dione

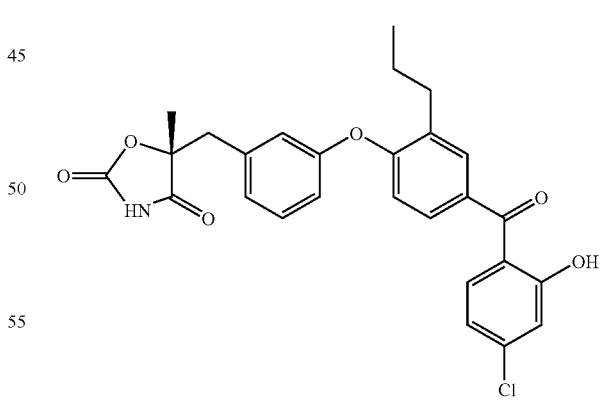

$^1$H NMR (500 MHz, CDCl$_3$) δ 12.2 (s, 1H), 7.64-7.66 (m, 2H), 7.5 (br. s. 1H), 7.51 (dd, J=8.5, 2.5 Hz, 1H), 7.37 (t, J=8.5 Hz, 1H), 7.13 (d, J=2.5 Hz, 1H), 7.07 (m, 1H), 7.02 (m, 1H), 6.93 (m, 1H), 6.92 (dd, J=8.5, 2.5 Hz, 1H), 6.83 (d, J=8.5 Hz, 1H), 3.23 (d, J=14.5 Hz, 1H), 3.14 (d, J=14.5 Hz, 1H), 2.76 (t, J=7.5 Hz, 1H), 1.73 (m, 2H), 1.71 (s, 3H), 1.02 (t, J=7.5 Hz, 1H).

MS (ESI, m/z): 494.1 (M$^+$+1).

Example 24

(5R)-5-{3-[4-(2-hydroxy-4-methoxybenzoyl)-2-propylphenoxy]benzyl}-5-methyl-1,3-oxazolidine-2,4-dione

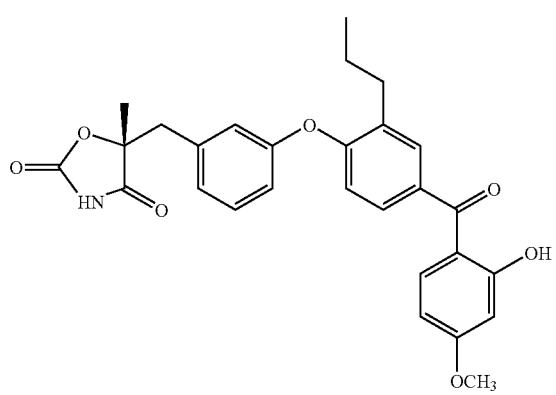

¹H NMR (500 MHz, CDCl₃) δ 7.74 (br.s, 1H), 7.57-7.64 (m, 2H), 7.48 (dd, J=8.5, 2.5 Hz, 1H), 7.33 (t, J=8.5 Hz, 1H), 7.03 (m, 1H), 6.78 (m, 1H), 6.9 (m, 1H), 6.82 (d, J=8.5 Hz, 1H), 6.55 (d, J=2.5 Hz, 1H), 6.46 (dd, J=8.5, 2.5 Hz, 1H), 3.89 (s, 3H), 3.20 (d, J=14.5 Hz, 1H), 3.12 (d, J=14.5 Hz, 1H), 2.72 (t, J=7.5 Hz, 2H), 1.71 (m, 2H), 1.68 (s, 3H), 0.99 (t, J=7.5 Hz, 1H).

MS (ESI, m/z): 490.2 (M⁺+1).

Example 25

(5R)-5-{3-[4-(4-Chloro-2-fluorobenzoyl)-2-propylphenoxy]phenylmethyl}-5-methyl-1,3-oxazolidine-2,4-dione, oxime

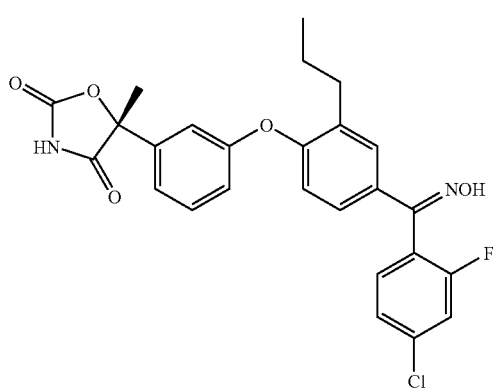

A mixture of the title compound of Example 9 (0.48 g, 1.0 mmol), hydroxyamine hydrochloride (0.35 g, 10 mmol) and sodium acetate (0.41 g, 10 mmol) in methanol (10 mL) was stirred at 50° C. for 16 h. The precipitate was removed by filtration and the filtrate was concentrated. The residue was taken up in diethyl ether and the resulting solution was filtered through a short path of silica gel to afford the title compound as a mixture of geometric isomers.

¹H NMR (500 MHz, CDCl₃) δ 8.48 (br. s, 1H), 7.17-7.45 (m, 8H), 6.98 (m, 1×0.3H), 6.94 (m, 1×0.7H), 6.83 (d, 1×0.3H), 6.79 (1×0.7H, 1H), 2.62 (m, 2H), 1.95 (s, 0.3×3H), 1.94(s, 0.7×3H), 1.63 (m, 2H), 0.94 (t, J=7.5, 0.3×3H), 0.93 (t, J=7.5 Hz, 0.7×3H).

MS (ESI, m/z): 479.0 (M⁺+H₂O).

Example 26

(5R)-5-{3-[4-(4-methoxybenzoyl)-2-propylphenoxy]phenylmethyl}-5-methyl-1,3-oxazolidine-2,4-dione, oxime

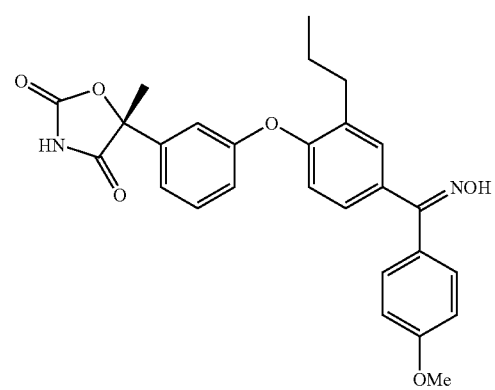

Using the procedure from Example 24, the title compound was prepared from (5R)-5-{3-[4-(4-Methoxybenzoyl)-2-propylphenoxy]phenyl}-5-methyl-1,3-oxazoline -2,4-dione (Example 1).

¹H NMR (500 MHz, CDCl₃) δ 8.28 (br. s, 1H), 7.87 (m, 1H), 6.80-7.76 (m, 10H), 3.94 (s, 3H), 2.72(m, 2H), 2.00 (s, 3H), 1.73 (m, 2H), 1.00 (t, J=7.5, 0.7×3H), 0.98 (t, J=7.5 Hz, 0.3×3H).

MS (ESI, m/z): 475.1 (M⁺+1).

Example 27

(5R)-5-{3-[4-(6-chlorobenzisoxazol-3-yl)-2-propylphenoxy]phenyl}-5-methyl-1,3-oxazolidine-2,4-dione

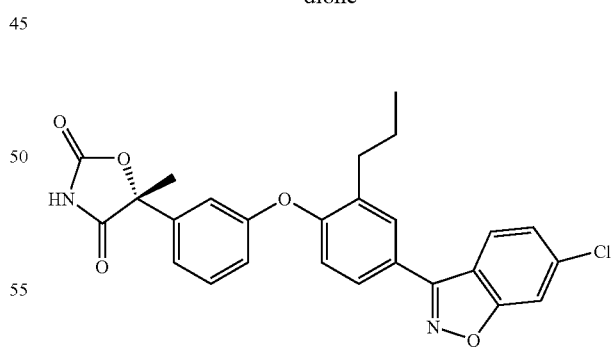

Step 1. Preparation of (5R)-5-{3-[4-(4-chloro-2-fluorobenzoyl)-2-propylphenoxy]phenylmethyl}-5-methyl-1,3-oxazolidine-2,4-dione, oxime A mixture of the title compound of Example 9 (0.48 g, 1.0 mmol), hydroxylamine hydrochloride (0.35 g, 10 mmol), and sodium acetate (0.41 g, 10 mmol) in methanol (10 mL) was stirred at 50° C. for 16 h. The precipitate was removed by filtration, and the filtrate was concentrated. The residue was taken up in diethyl ether and the resulting solution was filtered through a short path of silica gel to afford the title compound as a mixture of geometric isomers.

Step 2. (5R)-5-{3-[4-(6-chlorobenzisoxazol-3-yl)-2-propylphenoxy]phenyl}-5-methyl-1,3-oxazolidine-2,4-dione A mixture of the product from step 1 (0.49 g, 1.0 mmol) and Cs$_2$CO$_3$ (0.65 g, 2.0 mmol) in DMF (10 mL) was heated at 80° C. for 4 h. The reaction was diluted with ethyl acetate (20 mL) and washed with water (2×20 mL). After removal of the solvent, the residue was purified by reverse-phase preparative HPLC to afford the title compound.

$^1$H NMR (500 MHz, CD$_3$OD) δ 8.05 (d, J=8.5 Hz, 1H), 7.94 (d, J=2.5 Hz, 1H), 7.82-7.86 (m, 2H), 7.51 (dd, J=8.5, 2.5 Hz, 1H), 7.49 (d, J=8.5 Hz, 1H), 7.36 (m, 1H), 7.23 (t, J=2.5 Hz, 1H), 7.07 (d, J=8.5 Hz, 1H), 7.04 (m, 1H), 2.78 (t, J=7.5 Hz, 2H), 1.89 (s, 3H), 1.75 (m, 2H), 1.01 (s, 3H).

MS (ESI, m/z): 476.9 (M$^+$+1).

Example 28

(5R)-5-{3-[4-(6-methoxybenzoisoxazol-3-yl)-2-propylphenoxy]phenyl}-5-methyl-1,3-oxazolidine-2,4-dione

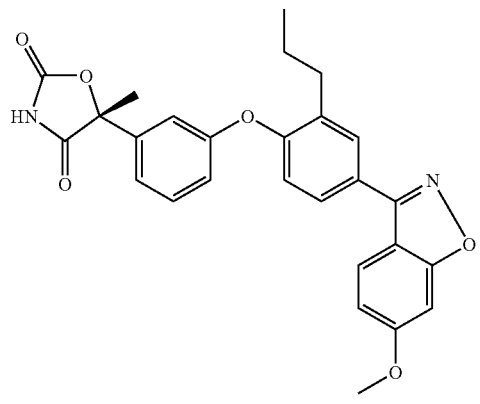

Using the procedure of Example 27, steps 1 and 2, the title compound was prepared from (5R)-5-{3-[4-(2-fluoro-4-methoxybenzoyl)-2-propylphenoxy]phenyl}-5-methyl-1,3-oxazolidine-2,4-dione (Example 10).

$^1$H NMR (500 MHz, CDCl$_3$) δ 8.09 (br. s, 1H), 7.88 (d, J=2 Hz, 1H), 7.78 (d, J=9.0 Hz, 1H), 7.75 (dd, J=8.5 Hz, 2.0 Hz, 1H), 7.42 (t, J=8.0 Hz, 1H), 7.34 (dd, J=8.0 Hz, 1.0 Hz, 1H), 7.32 (t, J=2.0 Hz, 1H), 7.10 (d, J=2.0 Hz, 1H), 7.01 (d, J=7.0 Hz, 1H), 7.00 (d, J=3.5 Hz, 1H), 6.99 (dd, J=2.5 Hz, 1.0 Hz, 1H), 3.95 (s, 3H), 2.75 (t, J=7.5 Hz, 2H), 1.97 (s, 3H), 1.74 (m, 2H), 1.01 (t, J=7.5 Hz, 3H).

MS (ESI, m/z): 473.0 (M+1).

Example 29

(5R)-5-{3-[4-(6-chlorobenzisoxazol-3-yl)-2-propylphenoxy]benzyl}-5-methyl-1,3-oxazolidine-2,4-dione

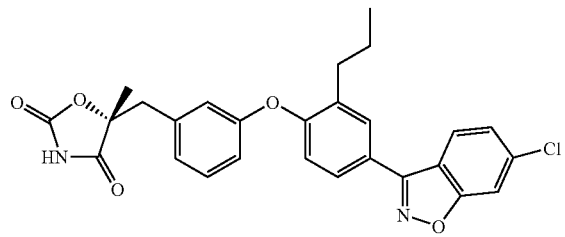

Using the procedure of Example 27, steps 1 and 2, the title compound was prepared from (5R)-5-{3-[4-(4-chloro-2-fluorobenzoyl)-2-propylphenoxy]benzyl}-5-methyl-1,3-oxazolidine-2,4-dione of Example 22.

$^1$H NMR (500 MHz, CD$_3$OD) δ 7.71(d, J=8.5 Hz, 1), 7.68 (d, J=2.5 Hz, 1H), 7.58 (dd, J=8.5, 2.5 Hz, 1H), 7.53 (d, J=2.5 Hz, 1H), 7.26 (dd, J=8.5, 2.5 Hz, 1H), 7.10 (t, J=8.5 Hz, 1H), 6.90 (d, J=8.5 Hz, 1H), 6.80-6.85 (m, 2H), 6.75 (dd, J=8.5, 2.5 Hz, 1H), 2.85 (m, 2H), 2.62 (t, J=7.5 Hz, 2H), 2.10 (s, 3H), 1.64 (m, 2H), 0.91 (t, J=7.5H, 3H).

MS (ESI, m/z): 491.0 (M$^+$+1).

Example 30

(5R)-5-{3-{[4-(6-methoxybenzisoxazol-3-yl)-2-propylphenoxy]phenyl}methyl}-5-methyl-1,3-oxazolidine-2,4-dione

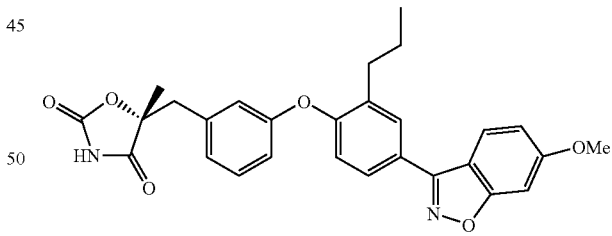

Using the procedure of Example 27, steps 1 and 2, the title compound was prepared from (5R)-5-{3-[4-(2-fluoro-4-methoxybenzoyl)-2-propylphenoxy]benzyl}-5-methyl-1,3-oxazolidine-2,4-dione (Example 21).

$^1$H NMR (500 MHz, CD$_3$OD) δ 7.86 (d, J=2.5 Hz, 1H), 7.78 (d, J=8.5 Hz, 1H), 7.75 (dd, J=8.5, 2.5 Hz, 1H), 7.31 (t, J=8.5 Hz, 1H), 7.08 (d, J=2.5Hz, 1H), 7.01 (m, 2H), 6.96 (m, 2H), 6.90 (m, 1H), 3.21 (d, J=14.5 Hz, 1H), 3.10 (d, J=14.5 Hz, 1H), 2.73 (t, J=7.5 Hz, 2H), 1.73 (m, 2H), 1.68 (s, 3H), 1.01 (t, J=7.5H, 3H).

MS (ESI, m/z): 487.1 (M$^+$+1).

Example 31

(5R)-5-{3-[4-(6-chlorobenzisothiazol-3-yl)-2-propylphenoxy]benzyl}-5-methyl-1,3-oxazolidine-2,4-dione

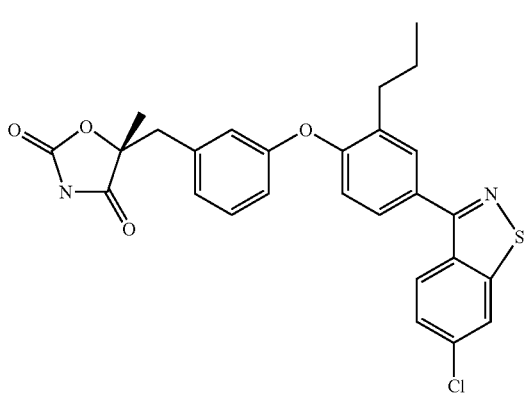

Step 1. Preparation of (5R)-5-{3-{4-[4-chloro-2-(benzylthio)benzoyl]-2-propylphenoxy}benzyl}-5-methyl-1,3-oxazolidine-2,4-dione A solution of potassium t-butoxide in THF (1 M, 1.3 mL, 1.3 mmol) was added to benzyl mercaptan (0.16 g, 1.3 mmol) in THF (5 mL). The resulting suspension was stirred at ambient temperature for 5 min., and then the title compound of Example 22 (0.59 g, 1.3 mmol) was added. After 30 min. at 25° C., the reaction mixture was poured into water and extracted with ethyl acetate. The organic phase was washed with brine, dried and concentrated. The residue was purified by chromatography on silica gel eluting with 3:7 ethyl acetate:hexane containing 1% acetic acid to afford the title compound.

Step 2. Preparation of (5R)-5-{3-[4-(6-chlorobenzisothiazol-3-yl)-2-propylphenoxy]benzyl}-5-methyl-1,3-oxazolidine-2,4-dione To a solution of the product from step 1 (0.57 g, 0.96 mmol) in dichloroethane (5 mL) was added dropwise sulfuryl chloride (0.08 mL, 1.0 mmol). After 1 h at 25° C., all the volatiles were removed in vacuo and the residue was suspended in THF (3 mL) and treated with a saturated solution of ammonia in ethanol (3 mL). The reaction was kept at 25° C. for 30 min and then concentrated in vacuo. The residue was purified by preparative reverse HPLC to afford the title compound.

$^1$H NMR (500 MHz, CDCl$_3$) δ 7.92 (d, J=8.7 Hz, 1H), 7.83 (d, J=1.3 Hz, 1H), 7.59 (d, J=1.3 Hz, 1H), 7.29 (m, 1H), 7.05 (t, J=8.0 Hz, 1H), 6.88 (d, J=8.4 Hz, 1H) 6.82 (m, 2H), 6.71 (d, J=8.0 Hz, 1H), 2.86 (m, 2H), 2.57 (t, J=7.6 Hz, 2H), 1.58 (m, 2H), 1.21 (s, 3H), 0.85 (t, J=7.2 Hz, 3H).

MS (ESI, m/z): 507.0 (M$^+$+1).

Example 32

(5R)-5-{3-[4-(4-chloro-2-pyridyloxy)-2-propylphenoxy]phenyl}-5-methyl-1,3-oxazolidine-2,4-dione

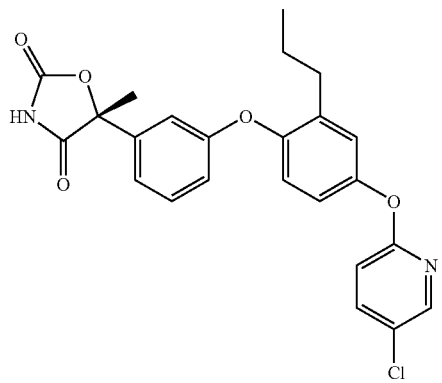

Step 1. Preparation of (2R)-5-[3-(4-acetyl-2-propylphenoxy)phenyl]-5-methyl-1,3-oxazolin-2,4-dione Intermediate 4 (3.3 g, 10 mmol) and sodium acetate (2.5 g, 30 mmol) were dissolved in triflic acid (30 mL). The resulting deep orange solution was stirred at 55° C. for 1 h. The reaction mixture was then diluted with ethyl acetate and poured slowly into ice. The organic layer was separated and washed successively with brine and aqueous NaHCO$_3$. Removal of the solvent gave the crude title compound.

Step 2. Preparation of (2R)-5-[3-(4-hydroxy-2-propylphenoxy)phenyl]-5-methyl-1,3-oxazolin-2,4-dione A mixture of the crude product from step 1 (3.7 g, 10 mol), m-chloroperbenzoic acid (70%, 4.9 g, 20 mmol) and sodium bicarbonate (2.5 g, 30 mmol) in dichloromethane 100 mL) was heated under reflux for 2 h. The reaction mixture was poured into aqueous sodium sulfite (2 N, 100 mL) and extracted with dichloromethane. The organic phase was washed with saturated aqueous sodium bicarbonate and concentrated. The residue was dissolved in methanol (50 ml) and treated with potassium hydroxide (5 N, 10 mL). After 30 min, the methanol solution was acidified with acetic acid to pH 4 and concentrated. The residue was purified by chromatography on silica gel eluting with 4:6 ethyl acetate:hexane to furnish the title compound.

Step 3. Preparation of (5R)-5-{3-[4-(4-chloro-2-pyridyloxy)-2-propylphenoxy]phenyl}-5-methyl-1,3-oxazolidine-2,4-dione A mixture of the title compound of step 2 (68 mg, 0.2 mmol) and CsF (61 mg, 0.4 mmol) in 2,5-dichloropyridine (0.5 mL) was heated at 125° C. for 16 h. Excess dichloropyridine was evaporated in vacuo and the residue was purified by preparative reverse-phase HPLC to furnish the title compound.

$^1$H NMR (500 MHz, CD$_3$OD) δ 8.13 (d, J=2.5 Hz, 1H), 7.83 (dd, J=8.5 Hz, 2.5 Hz, 1H), 7.40 (t, J=8.5 Hz, 2.5 Hz, 1H), 7.25 (d, J=8 Hz, 1H), 7.11 (t, J=2.5 Hz, 1H), 7.08 (d, J=2.5 Hz, 1H), 6.98 (d, J=5.5 Hz, 2H), 6.97 (d, J=6.0 Hz, 1H), 6.94 (dd, J=8.5 Hz, 2.5 Hz, 1H), 2.56 (t, J=7.5 Hz, 2H), 1.86 (s, 3H), 1.61 (m, 2H), 0.90 (t, J=7.5 Hz, 3H).

MS (ESI, m/z): 453.0 (M+1).

Example 33

(5R)-5-{3-[4-(3-chloro-4-pyridyloxy)-2-propylphenoxy]benzyl}-5-methyl-1,3-oxazolidine-2,4-dione

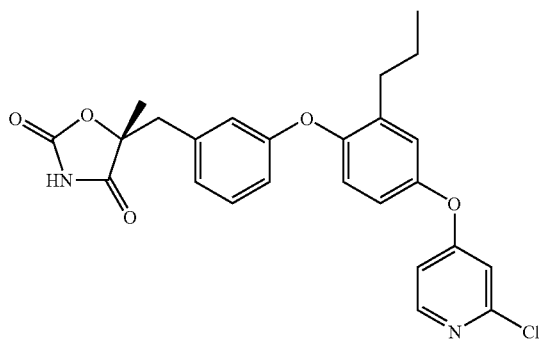

Step 1. Preparation of 5(R)-5-[3-(4-hydroxy-2-propylphenoxy)benzyl]-5-methyl-1,3-oxazolidine-2,4-dione The title compound was prepared following the same procedure as described in Example 32, steps 1 and 2, substituting Intermediate 8 for Intermediate 4 in step 1.

Step 2. Preparation of (5R)-5-{3-[4-(3-chloro-4-pyridyloxy)-2-propylphenoxy]benzyl}-5-methyl-1,3-oxazolidine-2,4-dione A mixture of the title compound from step 1 (70 mg, 0.2 mmol) and $Cs_2CO_3$ (130 mg, 0.4 mmol) in 2,4-dichloropyridine (0.5 mL) was heated at 125° C. for 16 h. Excess dichloropyridine was evaporated in vacuo. The residue was taken up in ethyl acetate and filtered through a short path of silica gel to to give a 2:3 mixture of the title compound and its regioisomer, which was separated by preparative reverse-phase HPLC to furnish the title compound.

$^1$H NMR (500 MHz, $CDCl_3$) δ 8.43 (d, J=5.5 Hz, 1H), 7.80 (s (br), 1H), 7.33 (m, 1H), 7.04 (d, J=2.0 Hz, 1H), 6.95 (m, 6H), 6.85 (s, 1H), 3.20 (d, J=14.1 Hz, 1H), 3.13 (d, J=14.1 Hz, 1H), 2.65 (t, J=7.6 Hz, 2H), 1.70 (s, 3H), 1.68 (m, 2H), 0.98 (t, J=7.5 Hz, 3H).

MS (ESI, m/z): 467.0 ($M^++1$).

Example 34

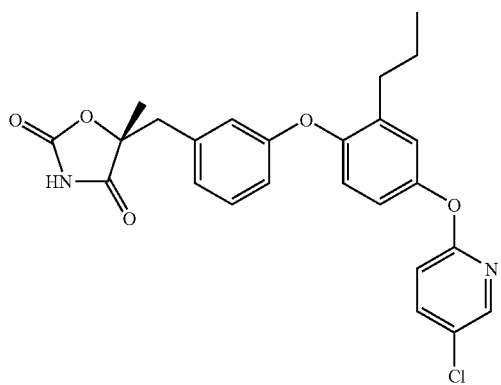

A mixture of the title compound from step 1 of Example 33 (70 mg, 0.2 mmol) and $Cs_2CO_3$ (130 mg, 0.4 mmol) in 2,5-dichloropyridine (0.5 mL) was heated at 125° C. for 16 h. Excess dichloropyridine was evaporated in vacuo and the residue was purified by preparative reverse-phase HPLC to furnish the title compound.

$^1$H NMR (500 MHz, $CDCl_3$) δ 8.80 (s, 1H), 8.11 (d, J=2.3 Hz, 1H), 7.71 (dd, J=8.7, 2.3 Hz, 1H), 7.27 (m, 1H), 7.05 (d, J=2.8 Hz, 1H), 6.92 (m, 4H), 6.69 (s, 1H), 3.24 (d, J=14.6 Hz, 1H), 3.05 (d, J=14.6 Hz, 1H), 2.57 (t, J=7.7 Hz, 2H), 1.64 (m, 5H), 0.94 (t, J=7.3 Hz, 3H).

MS (ESI, m/z): 467.0 ($M^++1$).

Example 35

(5R)-5-{3-[4-(6-chloroindazol-3-yl)-2-propylphenoxy]phenyl}-5-methyl-1,3-oxazolidine-2,4-dione

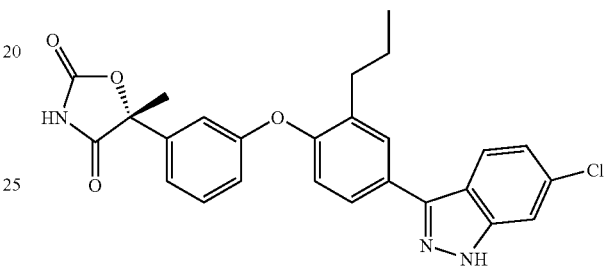

A solution of the title compound of Example 9 (0.48 g, 1.0 mmol) and anhydrous hydrazine (0.1 mL, 3.0 mmol) in DMSO (5.0 mL) was heated at 80° C. for 2 h. The reaction mixture was then concentrated in vacuo and the residue was purified by reverse phase preparative HPLC to afford the title compound.

$^1$H NMR (500 MHz, $CDCl_3$) δ 8.60 (br.s, 1H), 7.99 (d, J=8.5 Hz, 1H), 7.80 (d, J=2.5 Hz, 1H), 7.66-7.69 (m, 2H), 7.44 (t, J=8.5 Hz, 1H), 7.36(m, 1H), 7.31-7.34 (m, 2H), 7.03 (m, 2H), 6.30 (br.s, 1H), 2.78 (t, J=7.5 Hz, 2H), 1.99 (s, 3H), 1.76 (m, 2H), 1.04 (t, J=7.5 Hz, 3H).

MS (ESI, m/z): 476.0 ($M^++1$)

Example 36

(5R)-5-{3-{[4-(6-methoxyindazol-3-yl)-2-propylphenoxy]phenyl}-5-methyl-1,3-oxazolidine-2,4-dione

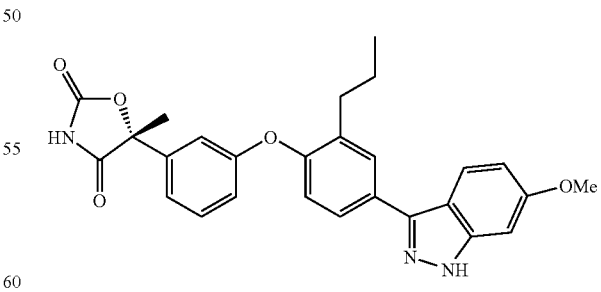

Using the procedure of example 35, the title compound was prepared from (5R)-5-{3-[4-(2-fluoro-4-methoxybenzoyl)-2-propylphenoxy]phenyl}-5-methyl-1,3-oxazolidine-2,4-dione of Example 10.

$^1$H NMR (500 MHz, $CDCl_3$) δ 7.89 (d, J=8.5 Hz, 1H), 7.83 (d, J=2.5 Hz, 1H), 7.71 (dd, J=8.5, 2.5 Hz, 1H), 7.42(t, J=8.5

Hz, 1H), 7.35 (m, 1H), 7.31 (t, J=2.5, 1H), 6.98-7.05 (m, 3H), 6.94 (d, J=2.5 Hz, 1H), 3.95 (s, 3H), 2.70 (t, J=7.5 Hz, 2H), 1.97 (s, 3H), 1.75 (m, 2H), 1.01 (t, J=7.5 Hz, 3H).

MS (ESI, m/z): 472.1 (M$^+$+1)

Example 37

(5R)-5-{3-{[4-(6-methoxy-1-methylindazol-3-yl)-2-propylphenoxy]phenyl}-5-methyl-1,3-oxazolidine-2,4-dione

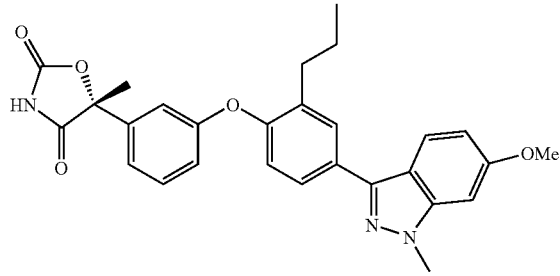

Using the procedure of Example 36 the title compound was prepared from (5R)-5-{3-[4-(2-fluoro-4-methoxybenzoyl)-2-propylphenoxy]phenyl}-5-methyl-1,3-oxazolidine-2,4-dione of Example 10, substituting methylhydrazine for hydrazine.

$^1$H NMR (500 MHz, CDCl$_3$) δ 8.06 (br.s, 1H), 7.85)d, J=8.5 Hz, 1H), 7.83 (d, J=2.5 Hz, 1H), 7.71 (dd, J=8.5, 2.5 Hz, 1H), 7.38(dd, J=8.5 Hz, 1H), 7.29 (m, 1H), 7.00 (d, J=8.5, 1H), 6.96 (m, 1H), 6.92 (dd, J=8.5, 2.5 Hz, 1H), 6.75 (d, J=2.5 Hz, 1H), 4.15 (s, 3H), 3.96 (s, 3H), 2.70 (t, J=7.5 Hz, 2H), 1.96 (s, 3H), 1.73 (m, 2H), 0.99 (t, J=7.5 Hz, 3H).

MS (ESI, m/z): 486.1 (M$^+$+1).

Example 38

(5R)-5-{3-[4-(6-methoxyindazol-3-yl)-2-propylphenoxy]benzyl}-5-methyl-1,3-oxazolidine-2,4-dione

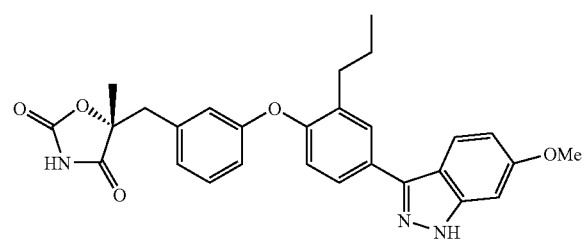

Using the procedure of Example 36, the title compound was prepared from (5R)-5-{3-[4-(2-fluoro-4-methoxybenzoyl)-2-propylphenoxy]benzyl}-5-methyl-1,3-oxazolidine-2,4-dione of Example 21.

$^1$H NMR (500 MHz, CD$_3$OD) δ 7.88 (d, J=9.5 Hz, 1H), 7.71 (d, J=2.5 Hz, 1H), 7.60 (dd, J=8.5, 2.5 Hz, 1H), 7.37 (t, J=8.5 Hz, 1H), 7.08 (d, J=8.5 Hz, 1H), 7.04 (dd, J=9.5, 2.5 Hz, 1H), 6.96 (d, J=2.5 Hz, 1H), 6.90 (m, 1H), 6.80 (d, J=8.5 Hz, 1H), 3.25 (d, J=14.5 Hz, 1H), 3.15 (d, J=14.5 Hz, 1H), 2.75 (t, J=7.5 Hz, 2H), 1.75 (m, 2H), 1.71 (s, 3H), 1.04 (s, 3H).

MS (ESI, m/z): 486.1 (M$^+$+1)

Example 39

(5R)-5-{3-[4-(6-methoxy-1-methylindazol-3-yl)-2-propylphenoxy]benzyl}-5-methyl-1,3-oxazolidine-2,4-dione

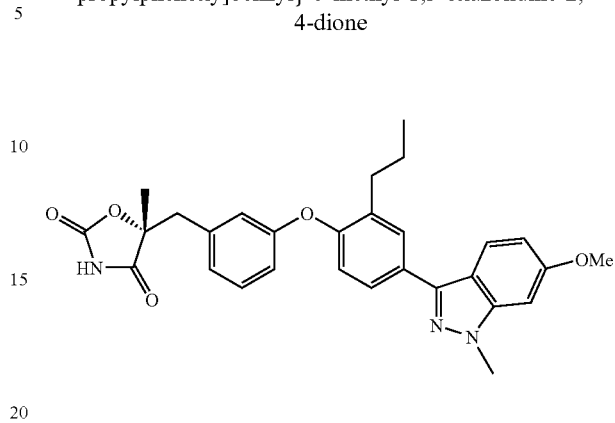

Using the procedure of Example 36, the title compound was prepared from (5R)-5-{3-[4-(2-fluoro-4-methoxybenzoyl)-2-propylphenoxy]benzyl}-5-methyl-1,3-oxazolidine-2,4-dione of Example 21, substituting methylhydrazine for hydrazine.

$^1$H NMR (500 MHz, CDCl$_3$) δ 7.88 (d, J=9.0 Hz, 1H), 7.83 (d, J=2.5 Hz, 1H), 7.74 (dd, J=8.5, 2.5 Hz, 1H), 7.30 (t, J=8.5 Hz, 1H), 6.95-7.00 (m, 2H), 76.92 (dd, J=9.0, 2.5 Hz, 1H), 6.88 (t, J=2.5 Hz, 1H), 6.77 (d, J=2.5 Hz, 1H), 4.11 (s, 3H), 3.97 (s, 3H), 3.21 (d, J=14.0 Hz, 1H), 3.12 (d, J=14.0 Hz, 1H), 2.71 (t, J=7.5 Hz, 2H), 1.75 (m, 2H), 1.70 (s, 3H), 1.01 (s, 3H).

MS (ESI, m/z): 500.1 (M$^+$+1)

Example 40

(5R)-5-{3-[4-(6-chloroindazol-3-yl)-2-propylphenoxy]benzyl}-5-methyl-1,3-oxazolidine-2,4-dione

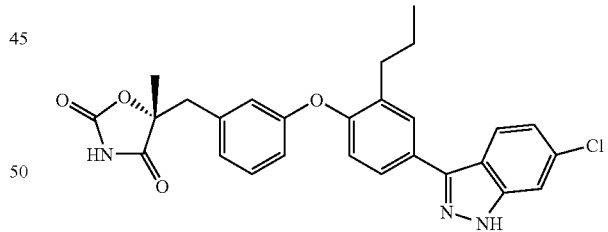

Using the procedure of Example 36, the title compound was prepared from (5R)-5-{3-[4-(4-chloro-2-fluorobenzoyl)-2-propylphenoxy]benzyl}-5-methyl-1,3-oxazolidine-2,4-dione of Example 22.

$^1$H NMR (500 MHz, CD$_3$OD) δ 8.90 (br.s, 1H), 7.90 (d, J=8.5 Hz, 1H), 7.70 (d, J=2.5 Hz, 1H), 7.56-7.62 (m, 1H), 7.35 (t, J=8.5 Hz, 1H), 7.27 (dd, J=8.5, 2.5 Hz, 1H), 7.05 (d, J=8.5Hz, 1H), 7.02 (dd, J=8.5, 2.5 Hz, 1H), 6.91 (t, J=2.5 Hz, 1H), 6.85 (d, J=8.5 Hz, 1H), 3.25 (d, J=14.5 Hz, 1H), 3.15 (d, J=14.5 Hz, 1H), 2.74 (t, J=7.5 Hz, 2H), 1.75 (m, 2H), 1.72 (s, 3H), 1.03 (s, 3H).

MS (ESI, m/z): 490.0 (M$^+$+1).

Example 41

(5R)-5-{3-[4-(6-chloro-1-methylindazol-3-yl)-2-propylphenoxy]benzyl}-5-methyl-1,3-oxazolidine-2,4-dione

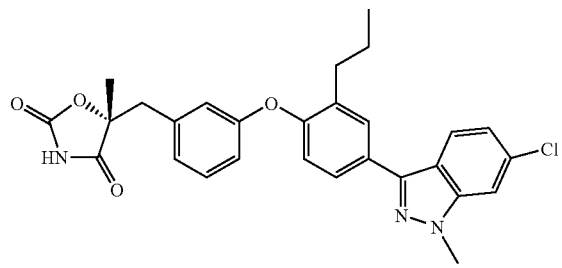

Using the procedure of Example 36 and substituting methylhydrazine for hydrazine, the title compound was prepared from (5R)-5-{3-[4-(4-chloro-2-fluorobenzoyl)-2-propylphenoxy]benzyl}-5-methyl-1,3-oxazolidine-2,4-dione of Example 22.

$^1$H NMR (500 MHz, CDCl$_3$) δ 7.93 (d, J=8.5 Hz, 1H), 7.82 (d, J=2.5 Hz, 1H), 7.72 (m, 2H), 7.46 (m, 1H), 7.30 (t, J=8.5 Hz, 1H), 7.22 (dd, J=8.5, 2.5 Hz, 1H), 6.95-7.00 (m, 3H), 6.88 (m, 1H), 3.21 (d, J=14.5 Hz, 1H), 3.12 (d, J=14.5 Hz, 1H), 2.72 (t, J=7.5 Hz, 2H), 1.75 (m, 2H), 1.69 (s, 3H), 1.01 (s, 3H).

MS (ESI, m/z): 504.1.0 (M$^+$+1).

Example 42

(5R)-5-{3-[4-(7-methoxy-2-oxo-2H-chromen-4-yl)-2-propylphenoxy]phenyl}-5-methyl-1,3-oxazolidine-2,4-dione

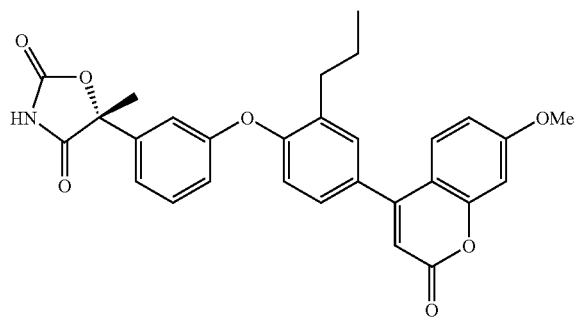

Step 1. 2-fluoro-5-(7-methoxy-2-oxo-2H-chromen-4-yl) benzaldehyde

A mixture of 4-fluoro-3-formylphenylboronic acid (0.34 g, 2.0 mmol), 7-methoxy-2-oxo-2H-chromen-4-yl trifluoromethanesulfonate (0.62 g, 2.0 mmol), K$_3$PO$_4$ (1.3 g, 6.0 mmol) and Pd(PPh$_3$)$_4$ (0.2 mmol) in dioxane (10 mL) was stirred at 80° C. for 8 h. The mixture was diluted with diethyl ether (50 mL) and filtered through a pad of silica gel. The filtrate was concentrated and the residue was purified by chromatography on silica gel to give the title compound.

Step 2. (5R)-5-{3-[2-formyl-4-(7-methoxy-2-oxo-2H-chromen-4-yl)phenoxy]phenyl}-5-methyl-1,3-oxazolidine-2,4-dione A mixture of the product from step 1 (0.30, 1.0 mmol) and intermediate 13 (0.20, 1.0 mmol) and Cs$_2$CO$_3$ (0.65 g, 2.0 mmol) in DMF (5.0 mL) was stirred at 80° C. for 4 h. The reaction mixture was poured into water and extracted with ethyl acetate. The organic phase was washed with water, dried over MgSO$_4$ and concentrated. The residue was purified by chromatography on silica gel to to give the title compound as a solid.

Step 3. (5R)-5-{3-[4(7-methoxy-2-oxo-2H-chromen-4-yl)-2-propylphenoxy]phenyl}-5-methyl-1,3-oxazolidine-2,4-dione To a suspension of ethyltriphenylphophonium bromide (0.56 g, 1.5 mmol) in THF (8 mL) cooled at −75° C. was added n-BuLi (1.6 M in hexane, 1.0 mL). To the resulting orange solution was added the product from step 2 (0.24 g, 0.50 mol) in THF (1.0 mL). The reaction mixture was gradually warmed to 25° C. and quenched with acetic acid (0.1 mL). The solvent was removed and the residue was taken up in diethyl ether and filtered through a short column of silica gel. The filtrated was concentrated and the residue was dissolved in THF-t-BuOH (1:1, v/v) (10 mL). The solution was stirred in the presence of Rh(PPh$_3$)$_3$Cl (40 mg) under hydrogen (45 psi) for 18 h. The reaction mixture was concentrated and the residue was purified by preparative HPLC on a RP-18 column using 10-100% acetonitrile in water gradient solvent system modified with 0.1% trifluoroacetic acid to give the title compound.

$^1$H NMR (500 MHz, CDCl$_3$) δ 8.40 (br. s, 1H), 7.51 (d, J=8.5 Hz, 1H), 7.45 (t, J=8.0 Hz, 1H), 7.37-7.41 (m, 2H), 7.34 (t, J=2.5 Hz, 1H), 7.28 (dd, J=8.5, 2.5 Hz, 1H), 7.03 (m, 1H), 6.97 (d, J=8.5 Hz, 1H), 6.95 (d, J=2.5 Hz, 1H), 6.88 (dd, J=8.5, 2.5 Hz, 1H), 6.29 (s, 1H), 3.95 (s, 3H), 2.74 (t, J=7.5 H, 2H), 1.99 (s, 3H), 1.74 (m, 2H), 1.02 (s, 3H).

MS (ESI, m/z): 500.2 (M$^+$+1).

Example 43

(5R)-5-{3-[4-(7-chloro-2-oxo-2H-chromen-4-yl)-2-propylphenoxy]phenyl}-5-methyl-1,3-oxazolidine-2,4-dione

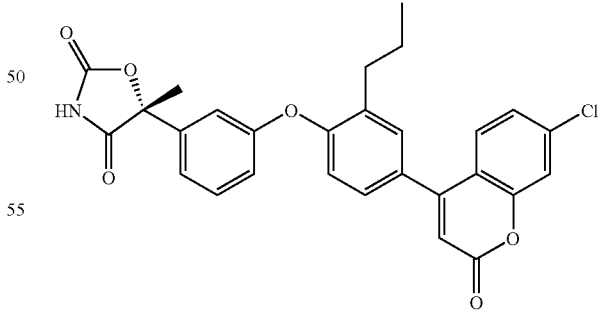

The title compound was prepared following the same procedure as described for Example 42, using 7-chloro-2-oxo-2H-chromen-4-yl trifluoromethanesulfonate instead of 7-methoxy-2-oxo-2H-chromen-4-yl trifluoromethanesulfonate in step 1.

$^1$H NMR (500 MHz, CD$_3$OD) δ 7.58 (d, J=8.5 Hz, 1H), 7.52 (d, J=2.5 Hz, 1H), 7.48 (d, J=2.5 Hz, 1H), 7.44 (t, J=8.5

Hz, 1H), 7.37 (d, J=2.5 Hz, 1H), 7.36 (d, J=2.5 Hz, 1H), 7.32 (m, 1H), 7.16 (t, J=2.5 Hz,1H), 7.02-7.07 (m, 2H), 6.42 (s, 1H), 2.71 (t, J=7.5 Hz, 2H), 1.72 (s, 3H), 1.68 (m, 2H), 0.96 (t, J=7.5 Hz, 3H).

MS (ESI, m/z): 504.1 (M$^+$+1)

Example 44

(5R)-5-{3-[4-(7-methoxy-2-oxo-2H-chromen-4-yl)-2-propylphenoxy]benzyl}-5-methyl-1,3-oxazolidine-2,4-dione, Sodium Salt

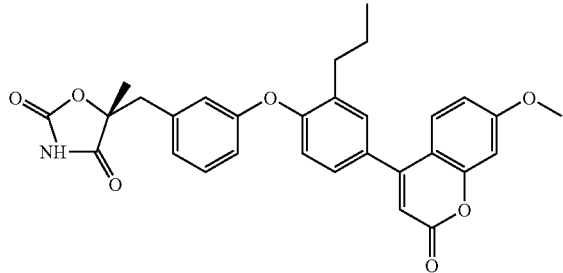

The title compound was prepared following the same procedure as described for Example 42, using intermediate 14 instead of intermediate 13 in step 2.

$^1$H NMR (500 MHz, CDCl$_3$) δ 7.69 (s, 1H), 7.51 (m, 2H), 7.34 (m, 2H), 7.25 (dd, J=8.2, 2.3 Hz, 1H), 6.99 (m, 2H), 6.90 (m, 2H), 6.86 (m, 1H), 6.25 (m, 1H), 3.17 (m, 2H), 2.71 (t, J=7.6 Hz, 2H), 1.72 (m, 2H), 1.69 (s, 3H), 1.62 (s, 3H), 1.00 (t, J=7.2 Hz, 3H).

MS (ESI, m/z): 514.2 (M$^+$+1).

Example 45

(5R)-5-{3-[4-(7-chloro-2-oxo-2H-chromen-4-yl)-2-propylphenoxy]benzyl}-5-methyl-1,3-oxazolidine-2,4-dione

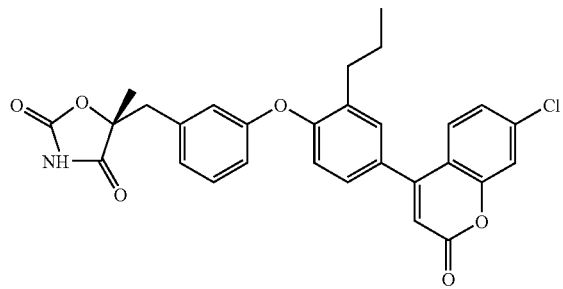

The title compound was preapared following the same procedure as described for Example 42, using 7-chloro-2-oxo-2H-chromen-4-yl trifluoromethanesulfonate instead of 7-methoxy-2-oxo-2H-chromen-4-yl trifluoromethanesulfonate in step 1 and intermediate 14 instead of intermediate 13 in step 2.

$^1$H NMR (500 MHz, CDCl$_3$) δ 7.50 (d, J=8.3 Hz, 1H), 7.37 (s, 1H), 7.26 (s, 1H), 7.22 (m, 2H), 6.96 (d, J=8.3 Hz, 1H), 6.85 (m, 3H), 6.41 (s, 1H), 2.96 (m, 2H), 2.63 (m, 2H), 1.63 (m, 2H), 1.39 (s, 3H), 0.93 (m, 3H).

MS (ESI, m/z): 518.2 (M$^+$+1).

Example 46

(5R)-5-{3-[4-(6-methoxy-1-naphthyl)-2-propylphenoxy]phenyl}-5-methyl-1,3-oxazolidine-2,4-dione

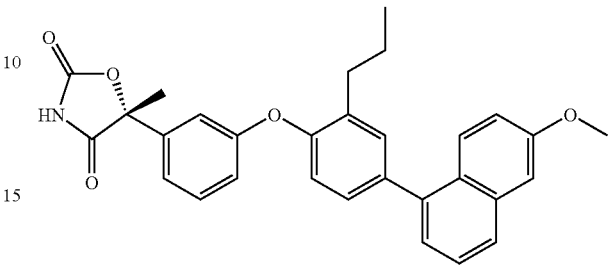

The title compound was prepared following the same procedure as described for Example 42, using 6-methoxy-1-naphthyl trifluoromethanesulfonate instead of 7-methoxy-2-oxo-2H-chromen-4-yl trifluoromethanesulfonate in step 1.

$^1$H NMR (500 MHz, CD$_3$OD) δ8.27 (d, J=8.5 Hz,1H), 8.02 (s, 1H), 7.74 (dd, J=8.5 Hz, 1.5 Hz, 1H), 7.66 (d, J=2.0 Hz, 1H), 7.57 (dd, J=8.0 Hz, 2.0 Hz, 1H), 7.49 (d, J=8.5 Hz, 1H), 7.41 (t, J=8.0 Hz, 1H), 7.34 (t, J=8.0 Hz, 1H), 7.28 (d, J=7.5 Hz, 1H), 7.20 (s, 1H), 6.96 (d, J=8.0 Hz, 1H), 6.89 (t, J=8.0 Hz, 2H), 4.03 (s, 3H), 2.69 (t, J=7.5 Hz, 2H), 1.75 (s, 3H), 1.70 (m, 2H), 0.97 (t, J=7.5 Hz, 3H).

MS (ESI, m/z) 482.2 (MH$^+$)

Example 47

(5R)-5-{3-[4-(6-methoxyisoquinolin-1-yl)-2-propylphenoxy]phenyl}-5-methyl-1,3-oxazolidine-2,4-dione

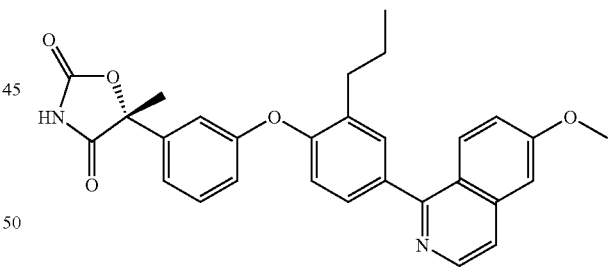

The title compound was prepared following the same procedure as described for Example 42, using (6-methoxyisoquinolin-1-yl)trifluoromethanesulfonate instead of 7-methoxy-2-oxo-2H-chromen-4-yl trifluoromethanesulfonate in step 1.

$^1$H NMR (500 MHz, CD$_3$OD) δ8.36 (d, J=5.5 Hz,1H), 7.97 (d, J=9.5 Hz, 1H), 7.72 (d, J=6.0 Hz, 1H), 7.53 (d, J=1.5 Hz, 1H), 7.42 (dd, J=7.5 Hz, 2.0 Hz, 1H), 7.37 (t, J=8.0 Hz, 1H), 7.35 (s, 1H), 7.31 (d, J=8.0 Hz, 1H), 7.27 (d, J=2.5 Hz, 1H), 7.26 (t, J=2.5 Hz, 1H), 7.00 (d, J=8.5 Hz, 1H), 6.92 (dd, J=8.0 Hz, 1.5 Hz, 1H), 3.99 (s, 3H), 2.73 (t, J=7.5 Hz, 2H), 1.75 (s, 3H), 1.71 (m, 2H), 0.98 (t, J=7.5 Hz, 3H).

MS (ESI, m/z) 483.1 (MH$^+$)

Example 48

(5R)-5-{3-[4-(7-methoxyquinolin-4-yl)-2-propylphenoxy]phenyl}-5-methyl-1,3-oxazolidine-2,4-dione

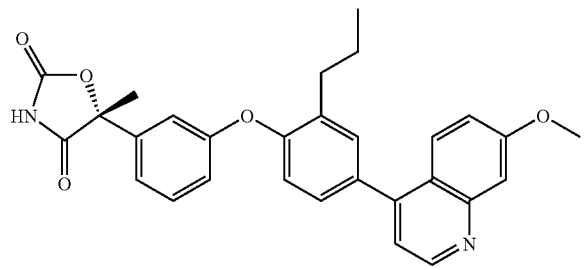

The title compound was prepared following the same procedure as described for Example 42, using (7-methoxyquinolin-4-yl)trifluoromethanesulfonate instead of 7-methoxy-2-oxo-2H-chromen-4-yl trifluoromethanesulfonate in step 1.

$^1$H NMR (500 MHz, CD$_3$OD) δ 8.99 (d, J=5.5 Hz,1H), 8.19 (d, J=9.0 Hz, 1H), 7.79 (d, J=5.5 Hz, 1H), 7.62 (d, J=2.0 Hz, 1H), 7.55 (dd, J=9.0 Hz, 2.5 Hz, 1H), 7.54 (t, J=2.5 Hz, 1H), 7.50 (d, J=8.0 Hz, 1H), 7.50 (t, J=8.0 Hz, 1H), 7.37 (d, J=8.0 Hz, 1H), 7.26 (t, J=2.0 Hz, 1H), 7.10 (d, J=8.5 Hz, 1H), 6.92 (dd, J=8.0 Hz, 2.0 Hz, 1H), 4.10 (s, 3H), 2.78 (t, J=7.5 Hz, 2H), 1.89 (s, 3H), 1.73 (m, 2H), 0.99 (t, J=7.5 Hz, 3H).

MS (ESI, m/z) 483.1 (MH$^+$)

Example of a Pharmaceutical Formulation

Exemplary 480 mg fill formulations that provide 25 mg and 150 mg doses of the compound of Example 1 for use in a standard gelatin capsule (576 mg) are shown below. Amounts of the components are in mg. These are made by combining and mixing the dry components and then transferring 480 mg to each capsule.

| Components | 25 mg Dose | 150 mg Dose |
|---|---|---|
| Compound of Ex. 1 | 25.0 mg | 150.0 mg |
| Lactose monohydrate (Diluent) | 417.6 | 282.0 |
| Croscarmellose sodium (Disintegrant) | 24.0 | 24.0 |
| Colloidal Silicon Dioxide (Glidant) | 1.4 | 9.6 |
| Talc (Glidant) | 9.6 | 9.6 |
| Sodium Lauryl Sulfate (Surfactant) | 2.4 | 4.8 |

What is claimed is:

1. A compound of formula I:

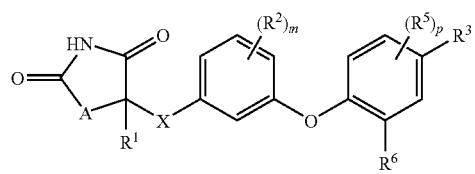

or a pharmaceutically acceptable salt thereof, wherein:

A is O or S;
X is a bond or —C(R$_7$)$_2$—;
R$^1$ is selected from the group consisting of H and C$_1$-C$_3$ alkyl, wherein C$_1$-C$_3$ alkyl is optionally substituted with 1-3 halogens;
each R$^2$ is independently selected from the group consisting of halogen, C$_1$-C$_3$ alkyl, and —OC$_1$-C$_3$ alkyl, wherein C$_1$-C$_3$ alkyl and —OC$_1$-C$_3$ alkyl are optionally substituted with 1-3 halogens;
R$^3$ is selected from the group consisting of

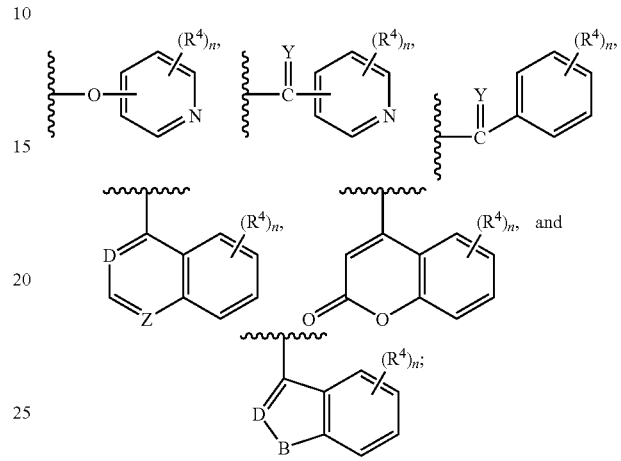

Y is selected from the group consisting of =O and =N—OH;
D and Z are each independently selected from the group consisting of =C(R$^7$)— and =N—;
B is selected from the group consisting of —N(R$^7$)—, —O— and —S—;
each R$^4$ is independently selected from the group consisting of halogen, —OH, C$_1$-C$_3$ alkyl, —OC$_1$-C$_3$ alkyl, —OC(=O)C$_1$-C$_3$ alkyl, and —S(O)$_q$C$_1$-C$_3$ alkyl, wherein C$_1$-C$_3$ alkyl, —OC$_1$-C$_3$ alkyl, —OC(=O)C$_1$-C$_3$ alkyl, and —S(O)$_q$C$_1$-C$_3$ alkyl are optionally substituted with 1-5 halogens;
each R$_5$ is independently selected from the group consisting of halogen, C$_1$-C$_3$ alkyl, and —OC$_1$-C$_3$ alkyl, wherein C$_1$-C$_3$ alkyl and —OC$_1$-C$_3$ alkyl are optionally substituted with 1-3 halogens;
R$_6$ is selected from the group consisting of C$_2$-C$_5$ alkyl, —CH$_2$Cyclopropyl, C$_3$-C$_6$ cycloalkyl, —OC$_2$-C$_5$ alkyl and —C(=O)C$_1$-C$_3$ alkyl, wherein the alkyl, cyclopropyl, and cycloalkyl groups of said R$_6$ substituent are optionally substituted with 1-3 halogens;
each R$^7$ is independently selected from the group consisting of H and C$_1$-C$_3$ alkyl, wherein C$_1$-C$_3$ alkyl is optionally substituted with 1-3 F;
m is an integer from 0-4;
n is an integer from 0-5;
p is an integer from 0-3; and
q is an integer from 0-2.

2. The compound of claim 1, or a pharmaceutically acceptable salt thereof, wherein:

X is a bond or CH$_2$;
R$^1$ is selected from the group consisting of H and C$_1$-C$_3$ alkyl, wherein C$_1$-C$_3$ alkyl is optionally substituted with 1-3 F;
each R$^2$ is independently selected from the group consisting of F, Cl, CH$_3$, CF$_3$, —OCH$_3$, and —OCF$_3$;
each R$^4$ is independently selected from the group consisting of halogen, —OH, C$_1$-C$_3$ alkyl, —OC$_1$-C$_3$ alkyl, —OC(=O)C$_1$-C$_3$ alkyl, and —S(O)$_q$C$_1$-C$_3$ alkyl, wherein $C_1$-$C_3$ alkyl, —$OC_1$-$C_3$ alkyl, —OC(=O)$C_1$-$C_3$ alkyl, and —S(O)$_q C_1$-$C_3$ alkyl are optionally substituted with 1-3 F;

each $R_5$ is independently selected from the group consisting of F, Cl, $CH_3$, —$OCH_3$, $CF_3$, and —$OCF_3$;

$R_6$ is selected from the group consisting of $C_2$-$C_5$ alkyl, —$CH_2$Cyclopropyl, and —C(=O)$C_1$-$C_3$ alkyl, wherein any alkyl or cycloalkyl groups of said $R_6$ substituent is optionally substituted with 1-3 F;

$R^7$ is selected from the group consisting of H and $C_1$-$C_3$ alkyl;

m is an integer selected from 0 and 1;

n is an integer from 0-3; and p is an integer from 0-2.

3. The compound of claim 1, or a pharmaceutically acceptable salt thereof, wherein $R^1$ is H or $CH_3$.

4. The compound of claim 1, or a pharmaceutically acceptable salt thereof, wherein $R^1$ is $CH_3$.

5. The compound of claim 1, or a pharmaceutically acceptable salt thereof, wherein A is O.

6. The compound of claim 1, or a pharmaceutically acceptable salt thereof, wherein each $R^4$ is independently selected from the group consisting of F, Cl, —OH, $CH_3$, $CF_3$, —$OCH_3$, —$OCHF_2$, —$OC_2H_5$, —OC(=O)$CH_3$, and —S(O)$_q CH_3$, wherein q is 0, 1 or 2, and n is 1 or 2.

7. The compound of claim 1, or a pharmaceutically acceptable salt thereof, wherein X is a bond.

8. The compound of claim 1, or a pharmaceutically acceptable salt thereof, wherein X is $CH_2$.

9. The compound of claim 1, or a pharmaceutically acceptable salt thereof, wherein $R^6$ is selected from the group consisting of n-$C_3H_7$, —$CH_2$Cyclopropyl, and —C(=O)$C_2H_5$.

10. The compound of claim 1, or a pharmaceutically acceptable salt thereof, wherein $R^6$ is n-$C_3H_7$.

11. The compound of claim 1, or a pharmaceutically acceptable salt thereof, wherein p is an integer from 0 to 2.

12. The compound of claim 1, or a pharmaceutically acceptable salt thereof,
wherein
A is O;
X is a bond or $CH_2$;
$R^1$ is $CH_3$;
each $R^4$ is independently selected from the group consisting of F, Cl, —OH, $CH_3$, $CF_3$, —$OCH_3$, —$OCF_3$, —$OCH_2CH_3$, —OC(=O)$CH_3$, —$OCHF_2$, and —S(O)$_q CH_3$;
$R^5$ is Cl or F;
$R^6$ is selected from the group consisting of n-$C_3H_7$, —$CH_2$Cyclopropyl, and —C(=O)$C_2H_5$;
$R^7$ is selected from H and $CH_3$;
m is 0;
n is an integer from 1-2;
p is 0 or 1; and
q is an integer from 0-2.

13. The compound of claim 12, or a pharmaceutically acceptable salt thereof, wherein $R^3$ is

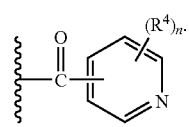

14. The compound of claim 12, or a pharmaceutically acceptable salt thereof, wherein $R^3$ is

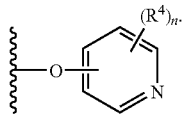

15. The compound of claim 12, or a pharmaceutically acceptable salt thereof, wherein $R^3$ is

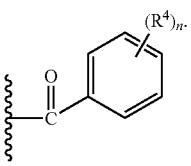

16. The compound of claim 12, or a pharmaceutically acceptable salt thereof, wherein $R^3$ is

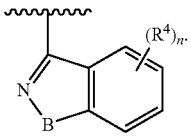

17. The compound of claim 12, or a pharmaceutically acceptable salt thereof, wherein $R^3$ is

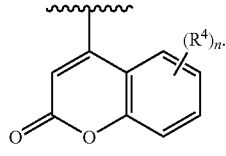

18. The compound of claim 12, or a pharmaceutically acceptable salt thereof, wherein $R^3$ is

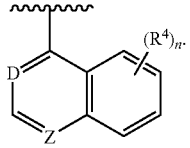

19. A pharmaceutical composition comprising the compound of claim 1, or a pharmaceutically acceptable salt thereof, and a pharmaceutically acceptable carrier.

20. A method for treating type 2 diabetes in a patient in need of treatment comprising the administration of a therapeutically effective amount of the compound of claim 1, or a pharmaceutically acceptable salt thereof.

21. The compound of claim 12, selected from the compounds listed below, or a pharmaceutically acceptable salt thereof:

-continued
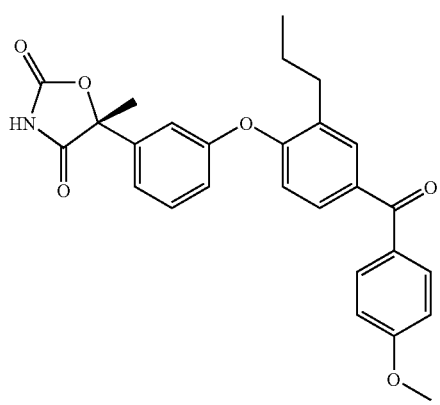
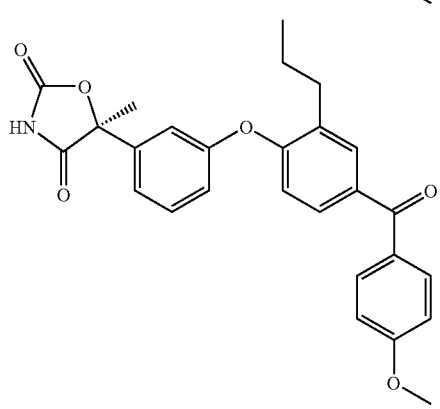
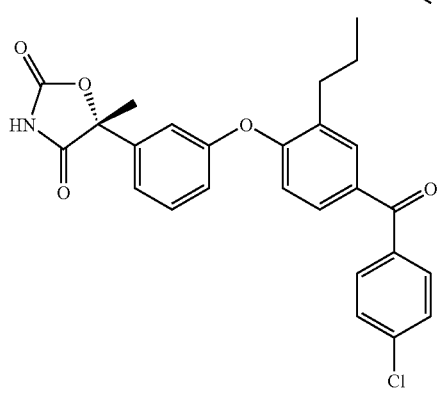
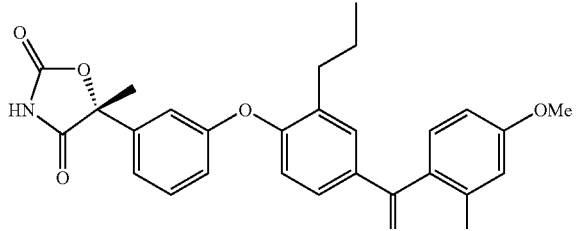
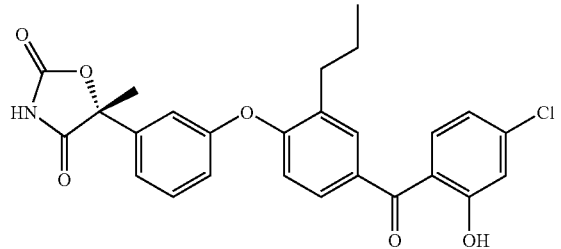
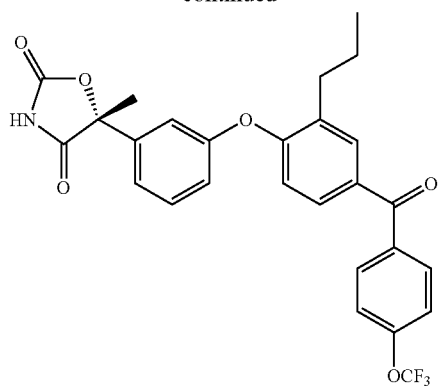
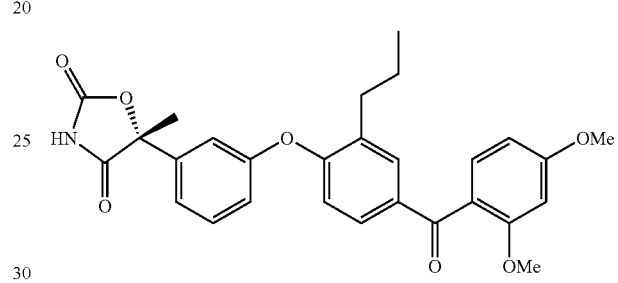
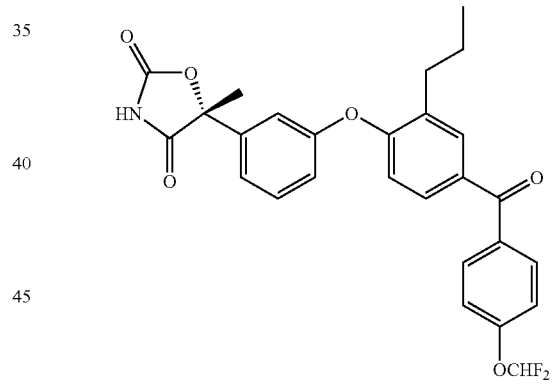
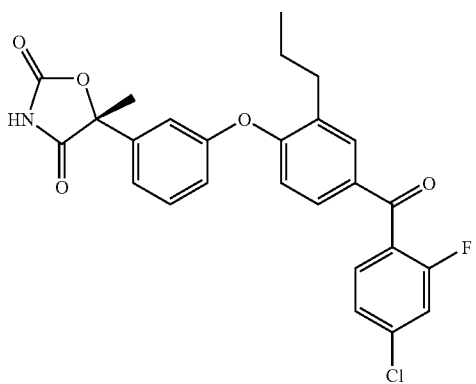

-continued
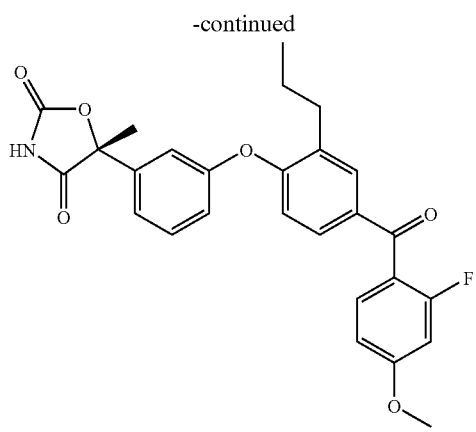
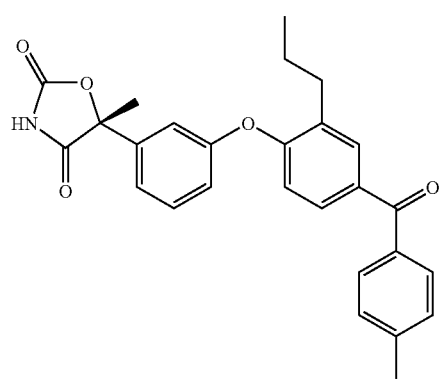
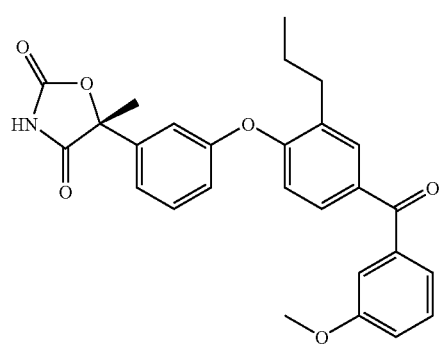
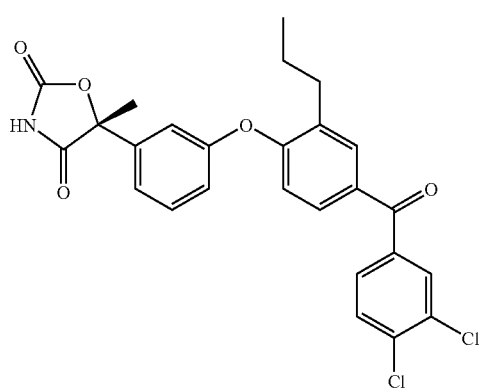
-continued
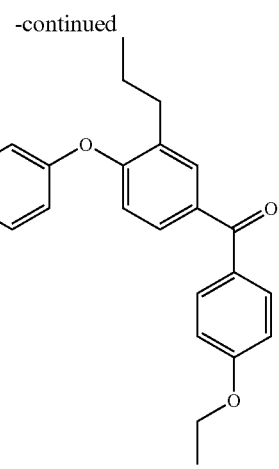
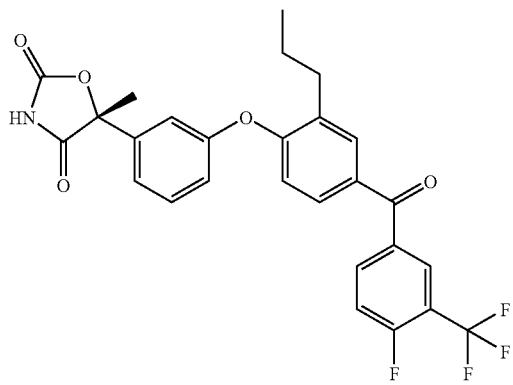
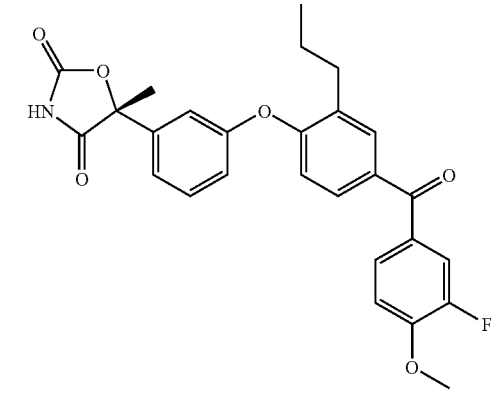
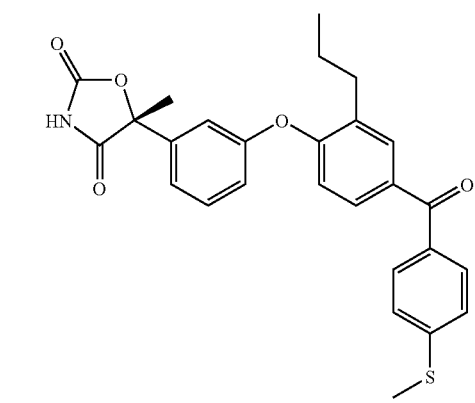

85
-continued
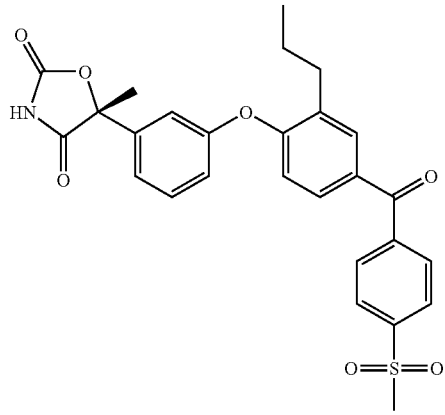
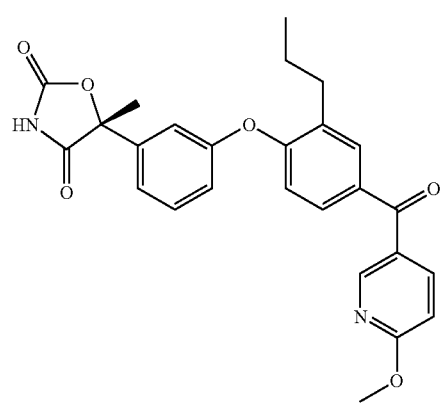
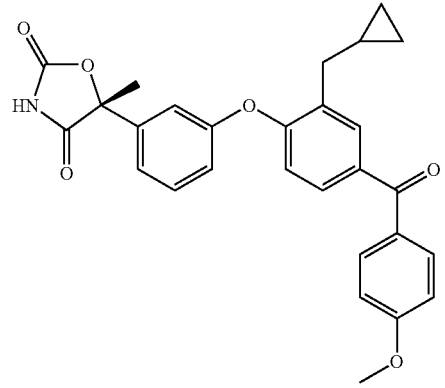
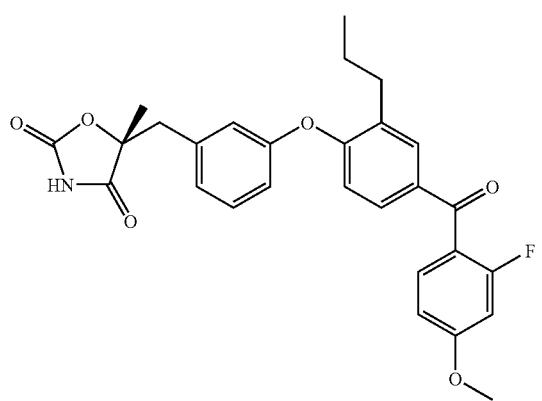
86
-continued
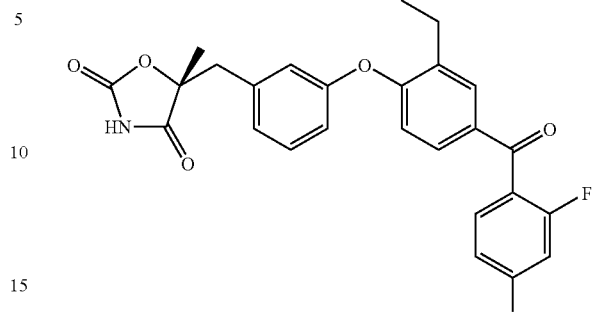
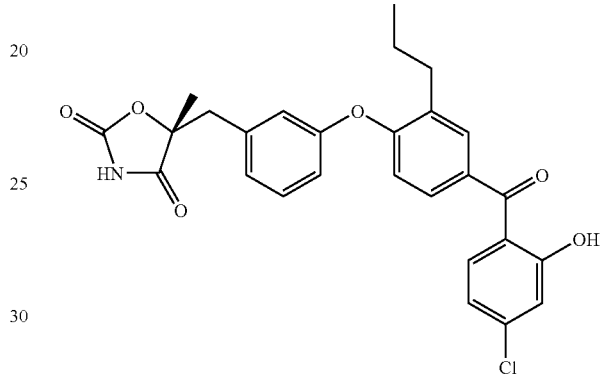
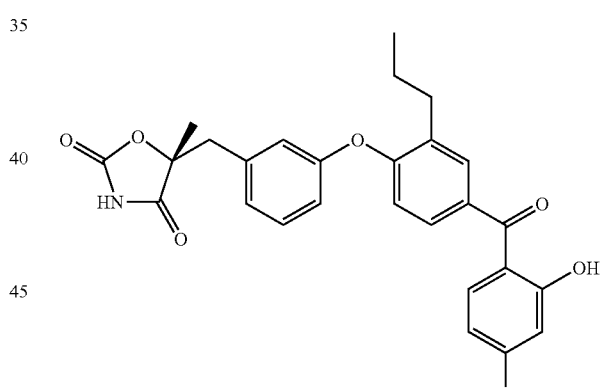
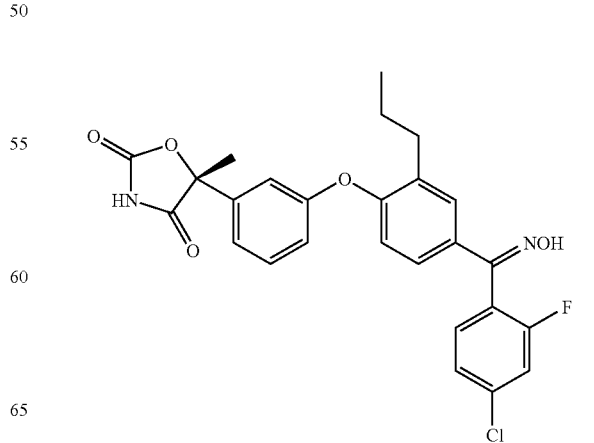

87
-continued
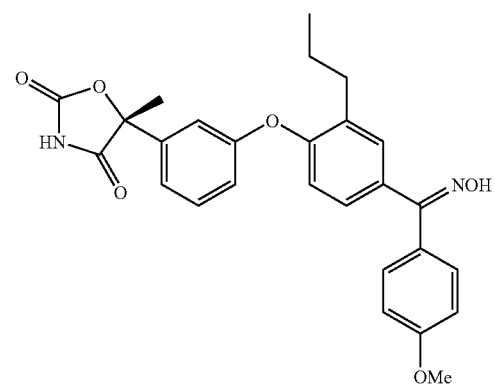
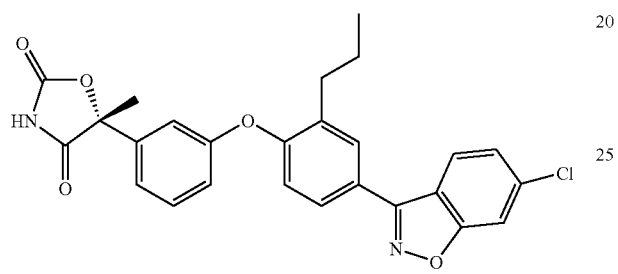
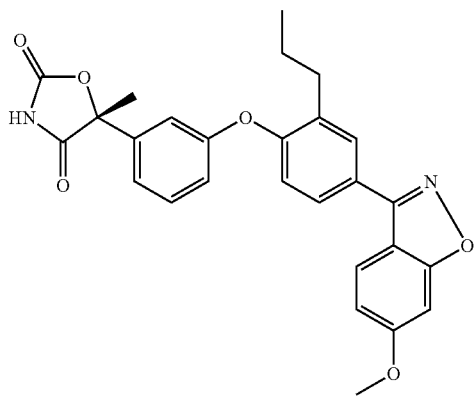
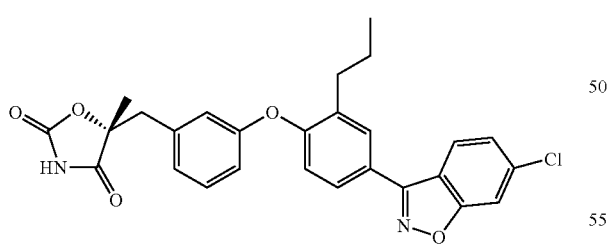
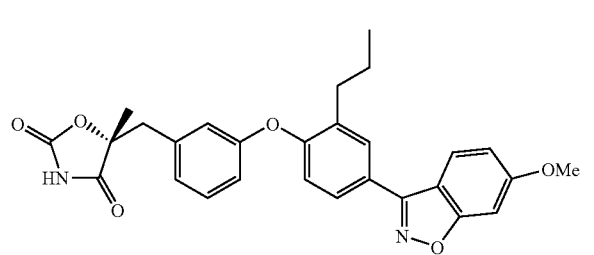
88
-continued
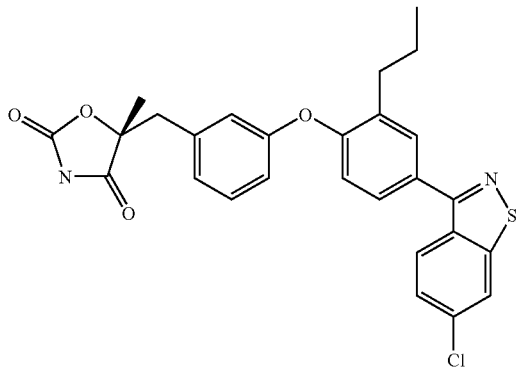
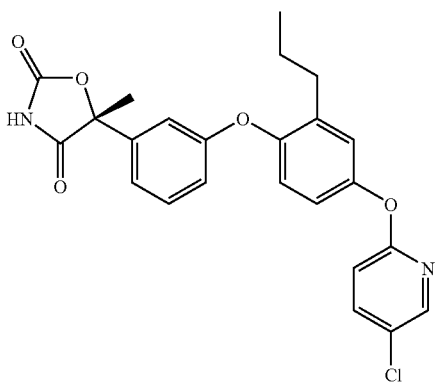
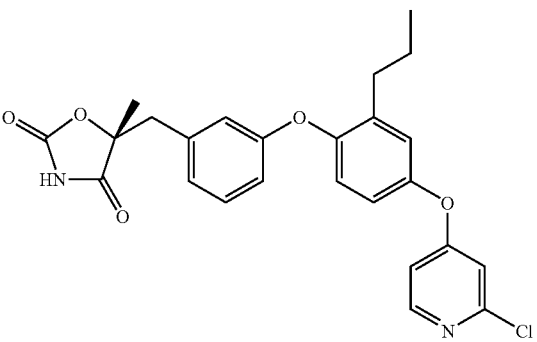
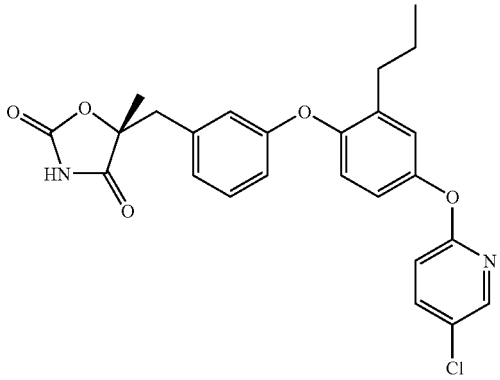

89
-continued
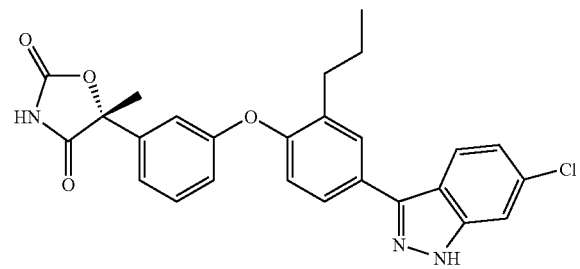
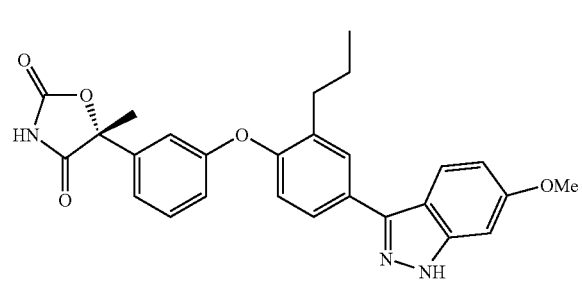
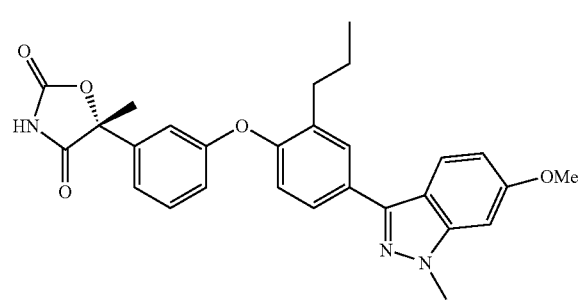
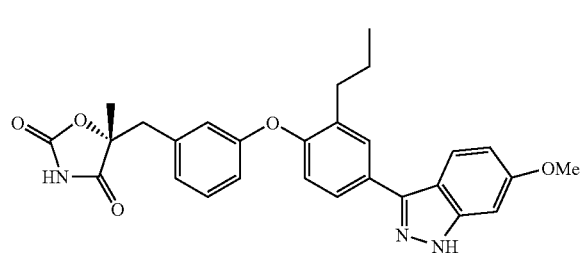
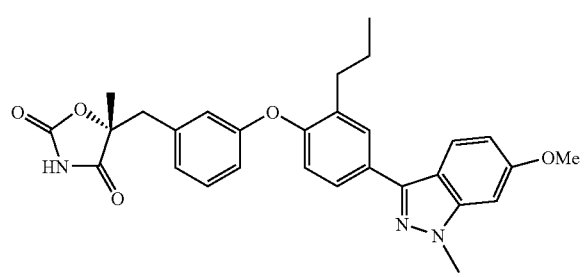
90
-continued
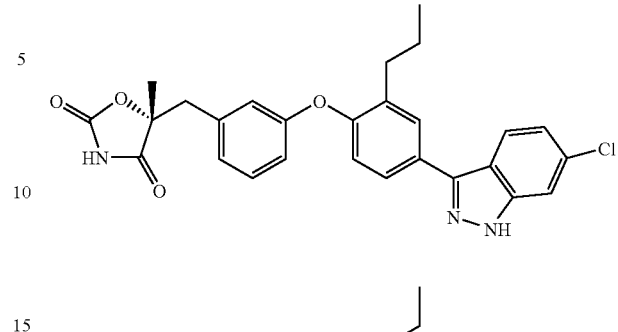
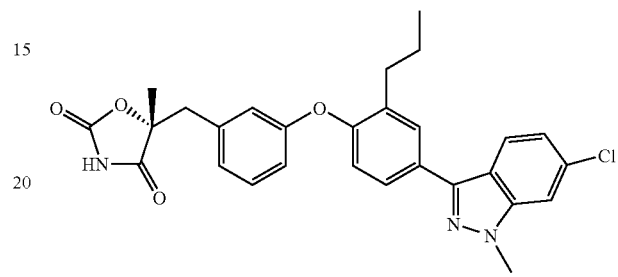
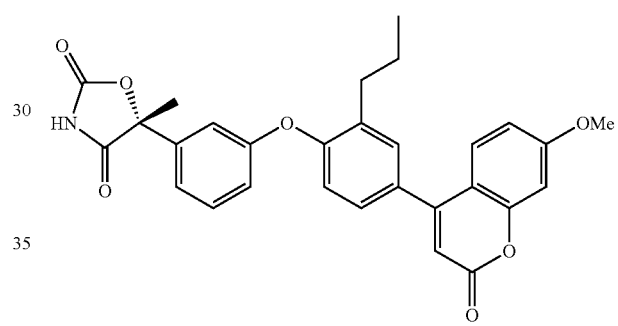
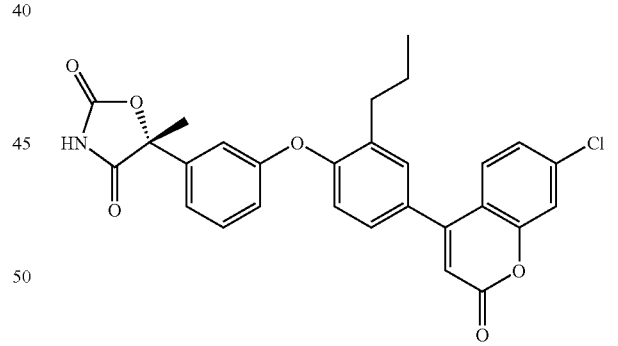
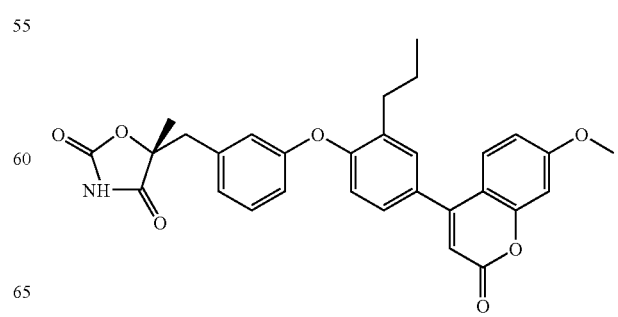

91
-continued
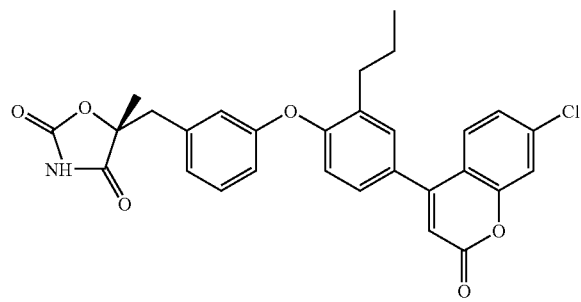
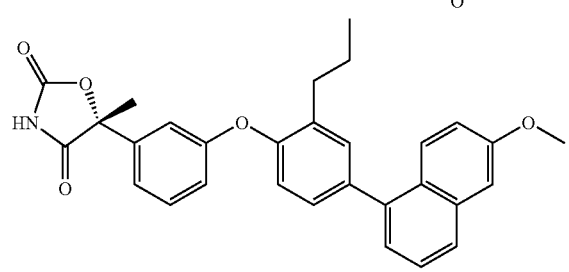
92
-continued
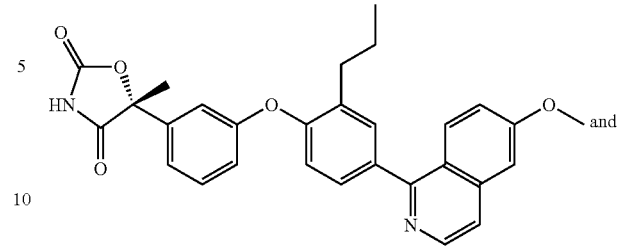
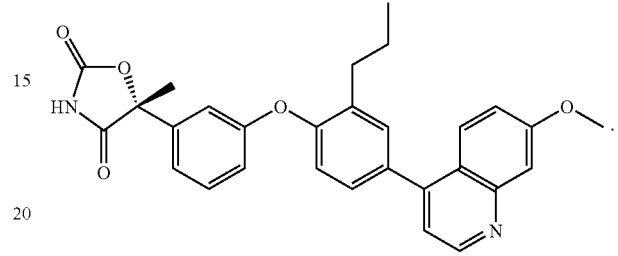
* * * * *